(12) United States Patent
Kim et al.

(10) Patent No.: US 11,370,796 B2
(45) Date of Patent: Jun. 28, 2022

(54) SUBSTITUTED PYRAZOLES AS LRRK2 INHIBITORS

(71) Applicant: OSCOTEC INC., Seongnam-si (KR)

(72) Inventors: Jung-Ho Kim, Seongnam-si (KR);
Jang-Sik Choi, Cheonan-si (KR);
Song-Eun Park, Seongnam-si (KR);
Hwa Sil Kim, Seongnam-si (KR);
Dong-Sik Jung, Cheonan-si (KR);
Jong-Sung Koh, Bucheon-si (KR);
Se-Won Kim, Seongnam-si (KR);
Jaekyoo Lee, North Andover, MA (US)

(73) Assignee: OSCOTEC INC., Seongnam-si (KR)

( * ) Notice: Subject to any disclaimer, the term of this patent is extended or adjusted under 35 U.S.C. 154(b) by 0 days.

(21) Appl. No.: 16/769,667

(22) PCT Filed: Dec. 3, 2018

(86) PCT No.: PCT/KR2018/015184
§ 371 (c)(1),
(2) Date: Jun. 4, 2020

(87) PCT Pub. No.: WO2019/112269
PCT Pub. Date: Jun. 13, 2019

(65) Prior Publication Data
US 2021/0363144 A1   Nov. 25, 2021

Related U.S. Application Data

(60) Provisional application No. 62/594,773, filed on Dec. 5, 2017.

(51) Int. Cl.
*A61K 31/4155* (2006.01)
*C07D 231/38* (2006.01)
*C07D 487/04* (2006.01)

(52) U.S. Cl.
CPC ................... *C07D 487/04* (2013.01)

(58) Field of Classification Search
CPC .......................... A61K 31/4155; C07D 231/38
USPC ........................................ 514/407; 548/373.1
See application file for complete search history.

(56) References Cited

FOREIGN PATENT DOCUMENTS

| KR | 10-2012-0102601 A | 9/2012 | |
|---|---|---|---|
| KR | 10-2013-0094693 A | 8/2013 | |
| KR | 10-2014-0059246 A | 5/2014 | |
| KR | 10-2015-0119210 A | 10/2015 | |
| WO | 2011/156698 A2 | 12/2011 | |
| WO | 2015113452 A1 | 8/2015 | |
| WO | 2017106771 A1 | 6/2017 | |
| WO | WO-2019112269 A1 * | 6/2019 | ............ A61P 25/28 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
International Search Report for PCT/KR2018/015184 dated Mar. 18, 2019 [PCT/ISA/210].

* cited by examiner

*Primary Examiner* — Douglas M Willis
(74) *Attorney, Agent, or Firm* — Sughrue Mion, PLLC

(57) ABSTRACT

A pyrrolo(pyrazolo)pyrimidine compound of Formula 1, a pharmaceutically acceptable salt, a hydrate, a solvate, a prodrug, and an isomer, and pharmaceutical compositions containing the compound are disclosed. The compound of Formula 1 shows excellent LRRK2 inhibitory activity. Method for manufacturing the compound and uses thereof as an LRRK2 inhibitor and methods for treating or preventing degenerative brain diseases employing the compound are disclosed:

[Formula 1]

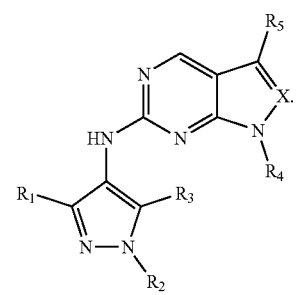

18 Claims, No Drawings

SUBSTITUTED PYRAZOLES AS LRRK2 INHIBITORS

CROSS REFERENCE TO RELATED APPLICATIONS

This application is a National Stage of International Application No. PCT/KR2018/015184 filed Dec. 3, 2018, claiming priority based on U.S. Provisional Patent Application No. 62/594,773 filed Dec. 5, 2017.

TECHNICAL FIELD

The present invention relates to a pyrrolo(pyrazolo)pyrimidine derivative having efficacy as an LRRK2 (leucine-rich repeat kinase 2) inhibitor and a pharmaceutical composition comprising the same for preventing or treating a degenerative brain disease.

BACKGROUND ART

LRRK2 (leucine-rich repeat kinase 2) is a member of the leucine-rich repeat kinase family. It consists of a sequence of 2,527 amino acids with highly conserved among interspecies. LRRK2 has dual functions with GTP hydrolase (GTPase) and serine-threonine kinase activities simultaneously.

LRRK2 is reported to be highly expressed in dopamine neurons of the cerebral cortex, substantia nigra, striatum, hippocampus, cerebellum associated with the pathogenesis of Parkinson's disease. In a postmortem study, expression of LRRK2 has been observed in abnormal protein aggregates called Lewy bodies, which result in specific dopamine neurons in Parkinson's disease patients.

In addition, it has been confirmed that a LRRK2 mutation with increased kinase activity (gain-of-functions' mutant) is closely associated with the occurrence of late-onset autosomal dominant Parkinson's disease. Thus, it is known that hyperactivity of LRRK2 has an important role on the initiation and progression of Parkinson's disease.

In particular, when normal LRRK2 is overexpressed in neurons, this leads to apoptosis induction. These physiological changes in LRRK2-derived cells are confirmed to be very similar to that of the cells from the neuronal cell death process in Parkinson's disease patients. The aberrantly activity of LRRK2 has a high clinical relationship with the initiation and progression of Parkinson's disease. It is expected that the modulation of LRRK2 activity would be beneficial to control both neuronal apoptosis and neurocytic inflammatory responses, which are the most important pathological evidence in Parkinson's disease.

Meanwhile, 40% of the patients who are currently treated with the drugs for Parkinson's disease have experienced motor fluctuation. Furthermore, the rate of patients experiencing motor fluctuation increases by 10% per one year due to the occurrence of drug-resistance after a certain period of time (e.g., 4 to 6 years from onset).

Accordingly, there is a need for developing a novel small molecule drug which capable of oral administration and offer acceptable safety profile.

Technical Problem

Thus, as the results of the studies, the present inventors have developed and synthesized a novel pyrrolo(pyrazolo) pyrimidine derivative to selectively inhibit LRRK2. It has been confirmed that the derivatives had an excellent inhibitory activity to LRRK2, whereby the present invention has been completed.

Accordingly, an object of the present invention is to provide a novel compound excellent in the inhibitory effect on the activity of LRRK2.

Another object of the present invention is to provide a pharmaceutical composition for preventing or treating a degenerative brain disease, which comprises the compound as an active ingredient.

Solution to Problem

One aspect of the present invention provides a compound selected from the group consisting of a compound represented by the following Formula 1, and a pharmaceutically acceptable salt, hydrate, solvate, prodrug, and isomer thereof.

[Formula 1]

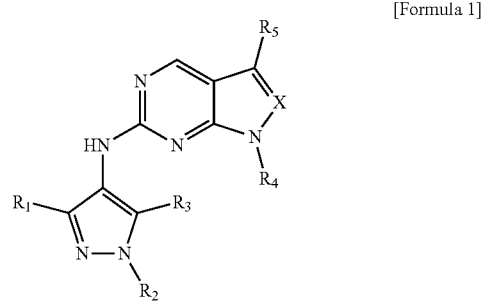

In the above formula,

X is CH or N;

$R_1$ is hydrogen, halogen, or $C_{1-4}$ alkyl or $C_{1-4}$ alkoxy unsubstituted or substituted with one or more halogens;

$R_2$ is $C_{1-6}$ alkyl, $C_{1-3}$ alkoxy $C_{1-6}$ alkyl, $C_{3-6}$ cycloalkyl $C_{1-6}$ alkyl, $C_{1-6}$ alkoxy, $C_{3-6}$ cycloalkyl, 4- to 7-membered heterocycloalkyl, or $C_{6-10}$ aryl unsubstituted or substituted with one or more halogens;

wherein the 4- to 7-membered heterocycloalkyl may be substituted with $C_{1-4}$ alkyl, $C_{1-4}$ alkylcarbonyl unsubstituted or substituted with one or more halogens, $C_{3-6}$ cycloalkylcarbonyl, 4- to 7-membered heterocycloalkylcarbonyl unsubstituted or substituted with $C_{1-4}$ alkyl, $C_{1-4}$ alkylsulfonyl, $C_{3-6}$ cycloalkylsulfonyl, or oxetanyl, and the heterocycloalkyl contains at least one atom selected from N, O, and S, $R_3$ is hydrogen, halogen, or $C_{1-4}$ alkyl;

$R_4$ is $C_{1-6}$ alkyl or $C_{3-6}$ cycloalkyl unsubstituted or substituted with one or more halogens; and $R_5$ is halogen or $C_{1-4}$ alkyl unsubstituted or substituted with one or more halogens.

Another aspect of the present invention provides a pharmaceutical composition for preventing or treating a degenerative brain disease, which comprises the compound as an active ingredient.

Advantageous Effects

The pyrrolo(pyrazolo)pyrimidine derivative according to the present invention is excellent in the selective inhibitory activity to LRRK2 and is useful as a drug for preventing or treating a degenerative brain disease including Parkinson's disease.

BEST MODE FOR CARRYING OUT EMBODIMENTS

Hereinafter, the invention will be described in detail with reference to embodiments. The embodiments are not limited to what is disclosed below. Rather, they may be modified in various forms as long as the gist of the invention is not altered.

In this specification, when a part is referred to as "comprising" a component, it means that the component can be further included rather than excluding other components, unless otherwise indicated.

In this specification, examples of halogen include fluorine, chlorine, bromine, and iodine.

One embodiment provides a compound selected from the group consisting of a compound represented by the following Formula 1, and a pharmaceutically acceptable salt, hydrate, solvate, prodrug, and isomer thereof.

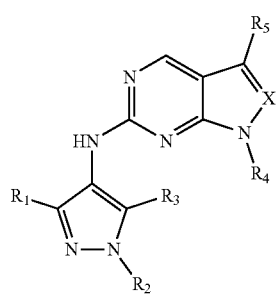

[Formula 1]

In the above formula,

X is CH or N;

$R_1$ is hydrogen, halogen, or $C_{1-4}$ alkyl or $C_{1-4}$ alkoxy unsubstituted or substituted with one or more halogens;

$R_2$ is $C_{1-6}$ alkyl, $C_{1-3}$ alkoxy $C_{1-6}$ alkyl, $C_{3-6}$ cycloalkyl $C_{1-6}$ alkyl, $C_{1-6}$ alkoxy, $C_{3-6}$ cycloalkyl, 4- to 7-membered heterocycloalkyl, or $C_{6-10}$ aryl unsubstituted or substituted with one or more halogens;

wherein the 4- to 7-membered heterocycloalkyl may be substituted with $C_{1-4}$ alkyl, $C_{1-4}$ alkylcarbonyl unsubstituted or substituted with one or more halogens, $C_{3-6}$ cycloalkylcarbonyl, 4- to 7-membered heterocycloalkylcarbonyl unsubstituted or substituted with $C_{1-4}$ alkyl, $C_{1-4}$ alkylsulfonyl, $C_{3-6}$ cycloalkylsulfonyl, or oxetanyl, and the heterocycloalkyl contains at least one atom selected from N, O, and S, $R_3$ is hydrogen, halogen, or $C_{1-4}$ alkyl;

$R_4$ is $C_{1-6}$ alkyl or $C_{3-6}$ cycloalkyl unsubstituted or substituted with one or more halogens; and $R_5$ is halogen or $C_{1-4}$ alkyl unsubstituted or substituted with one or more halogens.

According to an embodiment, $R_1$ is hydrogen, halogen, trifluoro $C_{1-4}$ alkyl, $C_{1-4}$ alkyl, or $C_{1-4}$ alkoxy.

According to an embodiment, $R_4$ is trifluoro $C_{1-4}$ alkyl, $C_{1-4}$ alkyl, or $C_{3-6}$ cycloalkyl.

According to an embodiment, $R_5$ is halogen, trifluoro $C_{1-4}$ alkyl, or $C_{1-4}$ alkyl.

According to an embodiment, $R_2$ is $C_{1-4}$ alkyl, $C_{1-3}$ alkoxy $C_{1-4}$ alkyl, $C_{3-6}$ cycloalkyl $C_{1-4}$ alkyl, $C_{1-4}$ alkoxy, $C_{3-6}$ cycloalkyl, 4- to 7-membered heterocycloalkyl, or $C_{6-10}$ aryl substituted with F or Cl, wherein the 4- to 7-membered heterocycloalkyl is substituted with $C_{1-4}$ alkyl, trifluoro $C_{1-4}$ alkylcarbonyl, $C_{1-4}$ alkylcarbonyl, $C_{3-6}$ cycloalkylcarbonyl, 4- to 7-membered heterocycloalkylcarbonyl unsubstituted or substituted with $C_{1-4}$ alkyl, $C_{1-4}$ alkylsulfonyl, $C_{3-6}$ cycloalkylsulfonyl, or oxetanyl, and the heterocycloalkyl contains at least one atom selected from N and O.

According to an embodiment, $R_2$ may be selected from the group consisting of

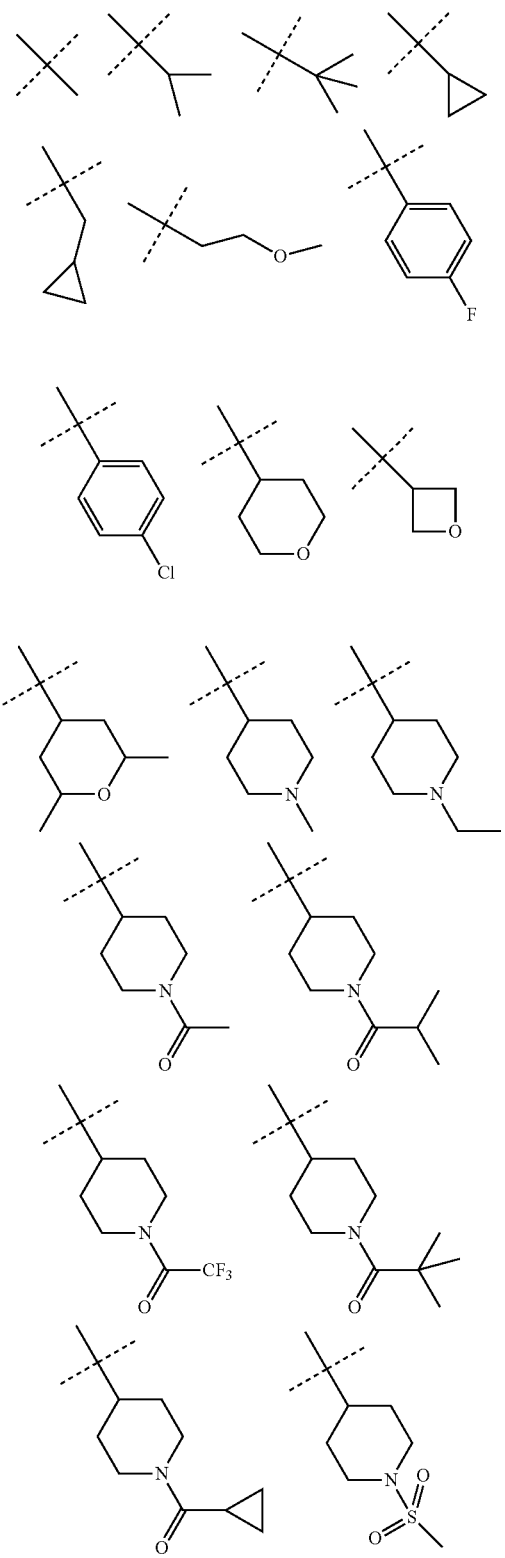

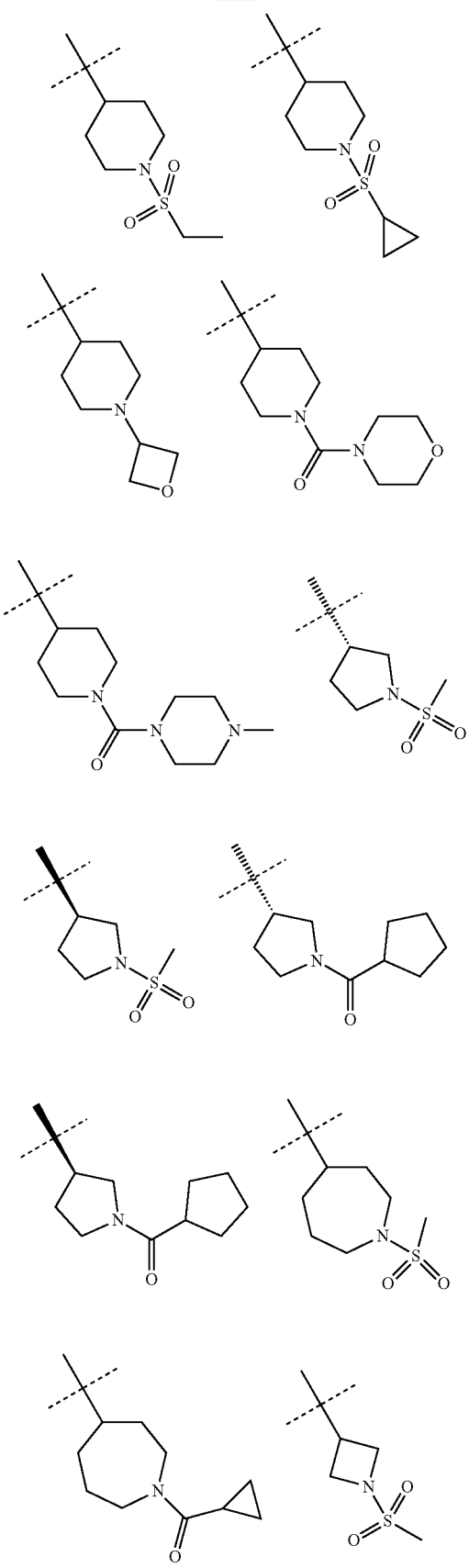
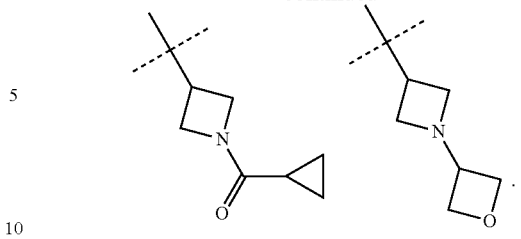

In the above substituents,
---- is the point of attachment to the nitrogen atom of the pyrazolyl ring.

According to an embodiment, the compound represented by Formula 1 may be selected from the group consisting of the following compounds.

1) N-(5-chloro-1-methyl-1H-pyrazol-4-yl)-7-methyl-5-(trifluoromethyl)-7H-pyrrolo[2,3-d]pyrimidin-2-amine,
2) 5-chloro-N-(1-isopropyl-3-methoxy-1H-pyrazol-4-yl)-7-methyl-7H-pyrrolo[2,3-d]pyrimidin-2-amine,
3) 5-chloro-N-(3-chloro-1-isopropyl-1H-pyrazol-4-yl)-7-methyl-7H-pyrrolo[2,3-d]pyrimidin-2-amine,
4) 5-chloro-7-methyl-N-(1-(tetrahydro-2H-pyran-4-yl)-3-(trifluoromethyl)-1H-pyrazol-4-yl)-7H-pyrrolo[2,3-d]pyrimidin-2-amine,
5) 5-chloro-N-(5-chloro-1-methyl-1H-pyrazol-4-yl)-7-methyl-7H-pyrrolo[2,3-d]pyrimidin-2-amine,
6) 5-chloro-N-(5-chloro-1-methyl-1H-pyrazol-4-yl)-7-ethyl-7H-pyrrolo[2,3-d]pyrimidin-2-amine,
7) 5-chloro-N-(3-chloro-1-isopropyl-1H-pyrazol-4-yl)-7-isopropyl-7H-pyrrolo[2,3-d]pyrimidin-2-amine,
8) 5-chloro-N-(3-chloro-1-isopropyl-1H-pyrazol-4-yl)-7-ethyl-7H-pyrrolo[2,3-d]pyrimidin-2-amine,
9) 5-chloro-N-(1-isopropyl-3-(trifluoromethyl)-1H-pyrazol-4-yl)-7-methyl-7H-pyrrolo[2,3-d]pyrimidin-2-amine,
10) 5-chloro-N-(1-(2-methoxyethyl)-3-(trifluoromethyl)-1H-pyrazol-4-yl)-7-methyl-7H-pyrrolo[2,3-d]pyrimidin-2-amine,
11) N-(1-butyl-3-(trifluoromethyl)-1H-pyrazol-4-yl)-5-chloro-7-methyl-7H-pyrrolo[2,3-d]pyrimidin-2-amine,
12) 5-chloro-N-(3-chloro-1-(2-methoxyethyl)-1H-pyrazol-4-yl)-7-ethyl-7H-pyrrolo[2,3-d]pyrimidin-2-amine,
13) 5-chloro-N-(3-chloro-1-(cyclopropylmethyl)-1H-pyrazol-4-yl)-7-ethyl-7H-pyrrolo[2,3-d]pyrimidin-2-amine,
14) 5-chloro-N-(3-chloro-1-cyclopropyl-1H-pyrazol-4-yl)-7-ethyl-7H-pyrrolo[2,3-d]pyrimidin-2-amine,
15) 5-chloro-N-(3-chloro-1-cyclopropyl-1H-pyrazol-4-yl)-7-cyclopropyl-7H-pyrrolo[2,3-d]pyrimidin-2-amine,
16) 5-chloro-N-(5-chloro-1-(oxetan-3-yl)-1H-pyrazol-4-yl)-7-ethyl-7H-pyrrolo[2,3-d]pyrimidin-2-amine,
17) 5-chloro-N-(3-chloro-1-(1-methylpiperidin-4-yl)-1H-pyrazol-4-yl)-7-ethyl-7H-pyrrolo[2,3-d]pyrimidin-2-amine,
18) 5-chloro-N-(3-chloro-1-(tetrahydro-2H-pyran-4-yl)-1H-pyrazol-4-yl)-7-ethyl-7H-pyrrolo[2,3-d]pyrimidin-2-amine,
19) 5-chloro-N-(3-chloro-1-(2,6-dimethyltetrahydro-2H-pyran-4-yl)-1H-pyrazol-4-yl)-7-ethyl-7H-pyrrolo[2,3-d]pyrimidin-2-amine,
20) 5-chloro-N-(3-chloro-1-(1-ethylpiperidin-4-yl)-1H-pyrazol-4-yl)-7-ethyl-7H-pyrrolo[2,3-d]pyrimidin-2-amine,
21) 5-chloro-N-(3-chloro-1-(4-fluorophenyl)-1H-pyrazol-4-yl)-7-ethyl-7H-pyrrolo[2,3-d]pyrimidin-2-amine, 22) 5-chloro-N-(5-chloro-1-(4-chlorophenyl)-1H-pyrazol-4-yl)-7-ethyl-7H-pyrrolo[2,3-d]pyrimidin-2-amine,
23) 1-(4-(5-chloro-4-(5-chloro-7-methyl-7H-pyrrolo[2,3-d]pyrimidin-2-ylamino)-1H-pyrazol-1-yl)piperidin-1-yl)ethanone,
24) (4-(3-chloro-4-(5-chloro-7-ethyl-7H-pyrrolo[2,3-d]pyrimidin-2-ylamino)-1H-pyrazol-1-yl)piperidin-1-yl)(cyclopropyl)methanone,
25) 5-chloro-N-(3-chloro-1-(1-(methylsulfonyl)piperidin-4-yl)-1H-pyrazol-4-yl)-7-ethyl-7H-pyrrolo[2,3-d]pyrimidin-2-amine,
26) 1-(4-(3-chloro-4-(5-chloro-7-ethyl-7H-pyrrolo[2,3-d]pyrimidin-2-ylamino)-1H-pyrazol-1-yl)piperidin-1-yl)-2-methylpropane-1-one,
27) 5-chloro-N-(5-chloro-1-(1-(oxetan-3-yl)piperidin-4-yl)-1H-pyrazol-4-yl)-7-methyl-7H-pyrrolo[2,3-d]pyrimidin-2-amine,
28) 5-chloro-N-(5-chloro-1-(1-(oxetan-3-yl)piperidin-4-yl)-1H-pyrazol-4-yl)-7-ethyl-7H-pyrrolo[2,3-d]pyrimidin-2-amine,
29) 5-chloro-N-(5-chloro-1-(1-(oxetan-3-yl)piperidin-4-yl)-1H-pyrazol-4-yl)-7-cyclopropyl-7H-pyrrolo[2,3-d]pyrimidin-2-amine,
30) 5-chloro-N-(3-chloro-1-(1-(methylsulfonyl)piperidin-4-yl)-1H-pyrazol-4-yl)-7-cyclopropyl-7H-pyrrolo[2,3-d]pyrimidin-2-amine,
31) (4-(3-chloro-4-(5-chloro-7-ethyl-7H-pyrrolo[2,3-d]pyrimidin-2-ylamino)-1H-pyrazol-1-yl)piperidin-1-yl)(morpholino)methanone,
32) (4-(3-chloro-4-(5-chloro-7-ethyl-7H-pyrrolo[2,3-d]pyrimidin-2-ylamino)-1H-pyrazol-1-yl)piperidin-1-yl)(4-methylpiperazin-1-yl)methanone,
33) 1-(4-(3-chloro-4-(5-chloro-7-ethyl-7H-pyrrolo[2,3-d]pyrimidin-2-ylamino)-1H-pyrazol-1-yl)piperidin-1-yl)-2,2-dimethylpropane-1-one,
34) 5-chloro-N-(3,5-dimethyl-1-(1-(methylsulfonyl)piperidin-4-yl)-1H-pyrazol-4-yl)-7-ethyl-7H-pyrrolo[2,3-d]pyrimidin-2-amine,
35) 5-chloro-N-(3-chloro-1-(1-(cyclopropylsulfonyl)piperidin-4-yl)-1H-pyrazol-4-yl)-7-ethyl-7H-pyrrolo[2,3-d]pyrimidin-2-amine,
36) (R)-5-chloro-N-(3-chloro-1-(1-(methylsulfonyl)pyrrolidin-3-yl)-1H-pyrazol-4-yl)-7-ethyl-7H-pyrrolo[2,3-d]pyrimidin-2-amine,
37) (S)-5-chloro-N-(3-chloro-1-(1-(methylsulfonyl)pyrrolidin-3-yl)-1H-pyrazol-4-yl)-7-ethyl-7H-pyrrolo[2,3-d]pyrimidin-2-amine,
38) (R)-(3-(3-chloro-4-(5-chloro-7-ethyl-7H-pyrrolo[2,3-d]pyrimidin-2-ylamino)-1H-pyrazol-1-yl)pyrrolidin-1-yl)(cyclopentyl)methanone,
39) (S)-(3-(3-chloro-4-(5-chloro-7-ethyl-7H-pyrrolo[2,3-d]pyrimidin-2-ylamino)-1H-pyrazol-1-yl)pyrrolidin-1-yl)(cyclopentyl)methanone,
40) 5-chloro-N-(3-chloro-1-(1-(methylsulfonyl)azetidin-3-yl)-1H-pyrazol-4-yl)-7-ethyl-7H-pyrrolo[2,3-d]pyrimidin-2-amine,
41) (3-(3-chloro-4-(5-chloro-7-ethyl-7H-pyrrolo[2,3-d]pyrimidin-2-ylamino)-1H-pyrazol-1-yl)azetidin-1-yl)(cyclopropyl)methanone,
42) 5-chloro-N-(3-chloro-1-(1-(methylsulfonyl)azepan-4-yl)-1H-pyrazol-4-yl)-7-ethyl-7H-pyrrolo[2,3-d]pyrimidin-2-amine,
43) (4-(3-chloro-4-(5-chloro-7-ethyl-7H-pyrrolo[2,3-d]pyrimidin-2-ylamino)-1H-pyrazol-1-yl)azepan-1-yl)(cyclopropyl)methanone,
44) 3-chloro-N-(3-chloro-1-(4-fluorophenyl)-1H-pyrazol-4-yl)-1-ethyl-1H-pyrazolo[3,4-d]pyrimidin-6-amine,
45) 3-chloro-N-(5-chloro-1-(1-(oxetan-3-yl)piperidin-4-yl)-1H-pyrazol-4-yl)-1-ethyl-1H-pyrazolo[3,4-d]pyrimidin-6-amine,
46) 3-chloro-N-(3-chloro-1-(1-(methylsulfonyl)piperidin-4-yl)-1H-pyrazol-4-yl)-1-cyclopropyl-1H-pyrazolo[3,4-d]pyrimidin-6-amine,
47) 3-chloro-N-(3-chloro-1-(1-(cyclopropylsulfonyl)piperidin-4-yl)-1H-pyrazol-4-yl)-1-ethyl-1H-pyrazolo[3,4-d]pyrimidin-6-amine,
48) 1-(4-(3-chloro-4-(3-chloro-1-ethyl-1H-pyrazolo[3,4-d]pyrimidin-6-ylamino)-1H-pyrazol-1-yl)piperidin-1-yl)-2,2,2-trifluoroethanone,
49) 3-chloro-N-(3-chloro-1-(1-(methylsulfonyl)piperidin-4-yl)-1H-pyrazol-4-yl)-1-(2,2,2-trifluoroethyl)-1H-pyrazolo[3,4-d]pyrimidin-6-amine,
50) 3-chloro-N-(5-chloro-1-(1-(oxetan-3-yl)piperidin-4-yl)-1H-pyrazol-4-yl)-1-(2,2,2-trifluoroethyl)-1H-pyrazolo[3,4-d]pyrimidin-6-amine,
51) 3-chloro-N-(3-chloro-1-(1-(methylsulfonyl)azepan-4-yl)-1H-pyrazol-4-yl)-1-ethyl-1H-pyrazolo[3,4-d]pyrimidin-6-amine,
52) (4-(3-chloro-4-(3-chloro-1-ethyl-1H-pyrazolo[3,4-d]pyrimidin-6-ylamino)-1H-pyrazol-1-yl)azepan-1-yl)(cyclopropyl)methanone,
53) 1-(4-(3-chloro-4-(3-chloro-1-ethyl-1H-pyrazolo[3,4-d]pyrimidin-6-ylamino)-1H-pyrazol-1-yl)piperidin-1-yl)-2,2-dimethylpropane-1-one,
54) (4-(3-chloro-4-(3-chloro-1-ethyl-1H-pyrazolo[3,4-d]pyrimidin-6-ylamino)-1H-pyrazol-1-yl)piperidin-1-yl)(morpholino)methanone,
55) 3-chloro-N-(3-chloro-1-(1-(methylsulfonyl)piperidin-4-yl)-1H-pyrazol-4-yl)-1-ethyl-1H-pyrazolo[3,4-d]pyrimidin-6-amine,
56) (4-(3-chloro-4-(3-chloro-1-ethyl-1H-pyrazolo[3,4-d]pyrimidin-6-ylamino)-5-methyl-1H-pyrazol-1-yl)piperidin-1-yl)(cyclopropyl)methanone,
57) (4-(3-chloro-4-(3-chloro-1-ethyl-1H-pyrazolo[3,4-d]pyrimidin-6-ylamino)-1H-pyrazol-1-yl)piperidin-1-yl)(cyclopropyl)methanone,
58) 1-(4-(3-chloro-4-(3-chloro-1-ethyl-1H-pyrazolo[3,4-d]pyrimidin-6-ylamino)-1H-pyrazol-1-yl)piperidin-1-yl)ethanone,
59) 3-chloro-N-(3-chloro-1-(1-(ethylsulfonyl)piperidin-4-yl)-1H-pyrazol-4-yl)-1-ethyl-1H-pyrazolo[3,4-d]pyrimidin-6-amine,
60) (3-(3-chloro-4-(3-chloro-1-ethyl-1H-pyrazolo[3,4-d]pyrimidin-6-ylamino)-1H-pyrazol-1-yl)azetidin-1-yl)(cyclopropyl)methanone,
61) 3-chloro-N-(5-chloro-1-(1-(oxetan-3-yl)azetidin-3-yl)-1H-pyrazol-4-yl)-1-ethyl-1H-pyrazolo[3,4-d]pyrimidin-6-amine,
62) 3-chloro-N-(5-chloro-1-(1-(methylsulfonyl)piperidin-4-yl)-1H-pyrazol-4-yl)-1-ethyl-1H-pyrazolo[3,4-d]pyrimidin-6-amine.

According to an embodiment, the LRRK2 inhibition rate ($IC_{50}$) according to the substituent of the compound represented by Formula 1 is as shown in Table 1 below. (++++: greater than 0 to 10 nM, +++: greater than 10 nM to 100 nM, ++: greater than 100 nM to 1,000 nM, +: greater than 1,000 nM to 10,000 nM).

TABLE 1

| No. | R₁ | R₂ | R₃ | R₄ | R₅ | X | IC$_{50}$ |
|---|---|---|---|---|---|---|---|
| 1 | H | Me | Cl | Me | CF₃ | CH | ++ |
| 2 | OMe | isopropyl | H | Me | Cl | CH | +++ |
| 3 | Cl | isopropyl | H | Me | Cl | CH | +++ |
| 4 | CF₃ | tetrahydropyran-4-yl | H | Me | Cl | CH | ++ |
| 5 | H | Me | Cl | Me | Cl | CH | +++ |
| 6 | H | Me | Cl | Et | Cl | CH | +++ |
| 7 | Cl | isopropyl | H | isopropyl | Cl | CH | +++ |
| 8 | Cl | isopropyl | H | Et | Cl | CH | +++ |
| 9 | CF₃ | isopropyl | H | Me | Cl | CH | ++ |
| 10 | CF₃ | 2-methoxyethyl-methyl | H | Me | Cl | CH | ++ |
| 11 | CF₃ | n-pentyl | H | Me | Cl | CH | + |
| 12 | Cl | 3-methoxypropyl | H | Et | Cl | CH | +++ |
| 13 | Cl | cyclopropylmethyl-methyl | H | Et | Cl | CH | +++ |
| 14 | Cl | cyclopropyl-methyl | H | Et | Cl | CH | +++ |

TABLE 1-continued

| No. | R₁ | R₂ | R₃ | R₄ | R₅ | X | IC₅₀ |
|---|---|---|---|---|---|---|---|
| 15 | Cl | cyclopropyl (gem-dimethyl) | H | cyclopropyl (gem-dimethyl) | Cl | CH | +++ |
| 16 | H | oxetan-3-yl (gem-dimethyl) | Cl | Et | Cl | CH | +++ |
| 17 | Cl | 1-methylpiperidin-4-yl (gem-dimethyl) | H | Et | Cl | CH | +++ |
| 18 | Cl | tetrahydropyran-4-yl (gem-dimethyl) | H | Et | Cl | CH | +++ |
| 19 | Cl | 2,6-dimethyltetrahydropyran-4-yl (gem-dimethyl) | H | Et | Cl | CH | +++ |
| 20 | Cl | 1-ethylpiperidin-4-yl (gem-dimethyl) | H | Et | Cl | CH | +++ |
| 21 | Cl | 4-fluorophenyl (gem-dimethyl) | H | Et | Cl | CH | ++ |
| 22 | H | 4-chlorophenyl (gem-dimethyl) | Cl | Et | Cl | CH | ++ |

TABLE 1-continued
| No. | R₁ | R₂ | R₃ | R₄ | R₅ | X | IC₅₀ |
|---|---|---|---|---|---|---|---|
| 23 | H | 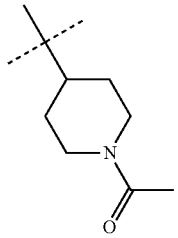 | Cl | Me | Cl | CH | +++ |
| 24 | Cl | 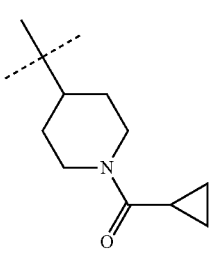 | H | Et | Cl | CH | +++ |
| 25 | Cl | 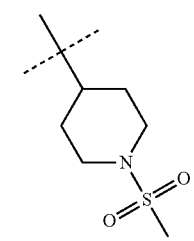 | H | Et | Cl | CH | ++++ |
| 26 | Cl | 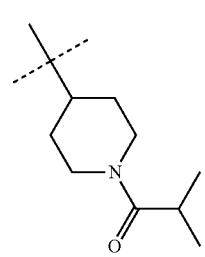 | H | Et | Cl | CH | +++ |
| 27 | H | 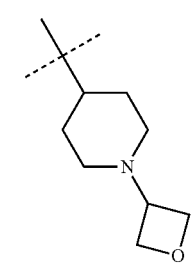 | Cl | Me | Cl | CH | +++ |
| 28 | H | 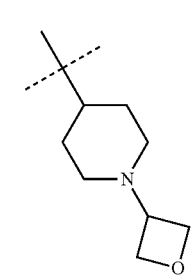 | Cl | Et | Cl | CH | ++++ |

TABLE 1-continued

| No. | R₁ | R₂ | R₃ | R₄ | R₅ | X | IC₅₀ |
|---|---|---|---|---|---|---|---|
| 29 | H | 4-(oxetan-3-yl)piperidin-1-yl (via piperidine C4) | Cl | cyclopropyl (quaternary) | Cl | CH | +++ |
| 30 | Cl | 1-(methylsulfonyl)piperidin-4-yl | H | cyclopropyl (quaternary) | Cl | CH | ++++ |
| 31 | Cl | 1-(morpholine-4-carbonyl)piperidin-4-yl | H | Et | Cl | CH | ++++ |
| 32 | Cl | 1-(4-methylpiperazine-1-carbonyl)piperidin-4-yl | H | Et | Cl | CH | ++++ |
| 33 | Cl | 1-pivaloylpiperidin-4-yl | H | Et | Cl | CH | ++++ |
| 34 | Me | 1-(methylsulfonyl)piperidin-4-yl | Me | Et | Cl | CH | ++ |

TABLE 1-continued

| No. | R₁ | R₂ | R₃ | R₄ | R₅ | X | IC₅₀ |
|---|---|---|---|---|---|---|---|
| 35 | Cl | *(4-(cyclopropylsulfonyl)piperidinyl)* | H | Et | Cl | CH | ++++ |
| 36 | Cl | *(3-methyl-1-(methylsulfonyl)pyrrolidinyl, (R))* | H | Et | Cl | CH | +++ |
| 37 | Cl | *(3-methyl-1-(methylsulfonyl)pyrrolidinyl, (S))* | H | Et | Cl | CH | +++ |
| 38 | Cl | *(3-methyl-1-(cyclopentanecarbonyl)pyrrolidinyl, (R))* | H | Et | Cl | CH | +++ |
| 39 | Cl | *(3-methyl-1-(cyclopentanecarbonyl)pyrrolidinyl, (S))* | H | Et | Cl | CH | +++ |
| 40 | Cl | *(3-methyl-1-(methylsulfonyl)azetidinyl)* | H | Et | Cl | CH | +++ |
| 41 | Cl | *(3-methyl-1-(cyclopropanecarbonyl)azetidinyl)* | H | Et | Cl | CH | +++ |

TABLE 1-continued
| No. | R₁ | R₂ | R₃ | R₄ | R₅ | X | IC₅₀ |
|---|---|---|---|---|---|---|---|
| 42 | Cl | 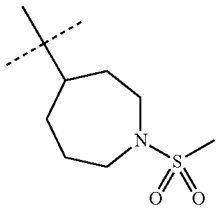 | H | Et | Cl | CH | ++++ |
| 43 | Cl | 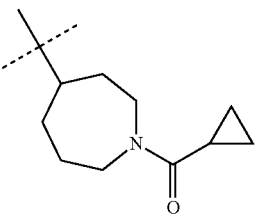 | H | Et | Cl | CH | ++++ |
| 44 | Cl | 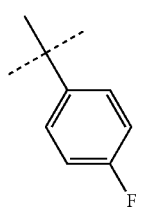 | H | Et | Cl | N | +++ |
| 45 | H | 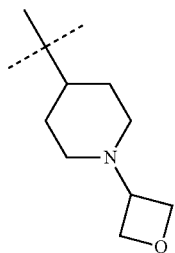 | Cl | Et | Cl | N | +++ |
| 46 | Cl | 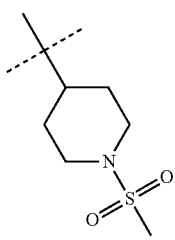 | H | 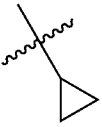 | Cl | N | ++++ |
| 47 | Cl | 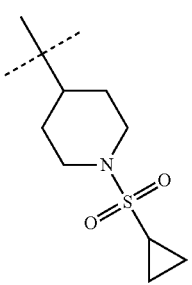 | H | Et | Cl | N | ++++ |

TABLE 1-continued

| No. | R₁ | R₂ | R₃ | R₄ | R₅ | X | IC₅₀ |
|-----|----|----|----|----|-----|---|------|
| 48 | Cl | 4-(trifluoroacetyl)piperidin-4-yl | H | Et | Cl | N | +++ |
| 49 | Cl | 4-(methylsulfonyl)piperidin-4-yl | H | CH₂CF₃ | Cl | N | +++ |
| 50 | H | 1-(oxetan-3-yl)piperidin-4-yl | Cl | CH₂CF₃ | Cl | N | +++ |
| 51 | Cl | 1-(methylsulfonyl)azepan-4-yl | H | Et | Cl | N | ++++ |
| 52 | Cl | 1-(cyclopropanecarbonyl)azepan-4-yl | H | Et | Cl | N | ++++ |
| 53 | Cl | 1-pivaloylpiperidin-4-yl | H | Et | Cl | N | ++++ |

TABLE 1-continued

| No. | R$_1$ | R$_2$ | R$_3$ | R$_4$ | R$_5$ | X | IC$_{50}$ |
|---|---|---|---|---|---|---|---|
| 54 | Cl | 4-(morpholine-4-carbonyl)piperidin-1-yl | H | Et | Cl | N | ++++ |
| 55 | Cl | 4-(methylsulfonyl)piperidin-1-yl | H | Et | Cl | N | ++++ |
| 56 | Cl | 4-(cyclopropanecarbonyl)piperidin-1-yl | Me | Et | Cl | N | ++ |
| 57 | Cl | 4-(cyclopropanecarbonyl)piperidin-1-yl | H | Et | Cl | N | ++++ |
| 58 | Cl | 4-acetylpiperidin-1-yl | H | Et | Cl | N | ++++ |
| 59 | Cl | 4-(ethylsulfonyl)piperidin-1-yl | H | Et | Cl | N | ++++ |

TABLE 1-continued

| No. | R₁ | R₂ | R₃ | R₄ | R₅ | X | IC₅₀ |
|---|---|---|---|---|---|---|---|
| 60 | Cl | ![azetidine-cyclopropyl carbonyl] | H | Et | Cl | N | +++ |
| 61 | H | ![azetidine-oxetane] | Cl | Et | Cl | N | +++ |
| 62 | H | ![piperidine-methanesulfonyl] | Cl | Et | Cl | N | +++ |

According to an embodiment, examples of the pharmaceutically acceptable salt of the compound represented by Formula 1 include alkaline metal salts, alkaline earth metal salts, ammonium salts, amine salts, acid addition salts, hydrate salts, and the like. They may be non-toxic and water-soluble. For example, they may be inorganic acid salts such as hydrochloride, hydrobromide, hydroiodide, sulfate, phosphate, and nitrate; and organic acid salts such as acetate, formate, lactate, tartrate, tannate, succinate, maleate, fumarate, benzoate, citrate, methanesulfonate, ethanesulfonate, benzenesulfonate, toluenesulfonate, isethionate, glucuronate, gluconate, and fatty acid salts.

According to an embodiment, the pharmaceutically acceptable salt may be one or more selected from the group consisting of hydrochloride, hydrobromide, hydroiodide, sulfate, nitrate, methanesulfonate, ethanesulfonate, benzenesulfonate, and toluenesulfonate.

The hydrate and solvate of the compound represented by Formula 1 according to an embodiment may be prepared by a method well known in the field. Specifically, they may be a hydrate and a solvate to which 1 to 5 molecules of water and an alcohol-based solvent (especially, ethanol or the like) are bonded, respectively, and are preferably non-toxic and water-soluble.

The prodrug of the compound represented by Formula 1 according to an embodiment is a chemical derivative capable of being converted into the compound represented by Formula 1 in vivo when administered. It may be prepared by a method well known in the field.

The isomer of the compound represented by Formula 1 according to an embodiment include optical isomers (e.g., enantiomers, diastereomers, and mixtures thereof), as well as conformation isomers and position isomers.

The compound of Formula 1a (where X is CH) according to an embodiment may be prepared by the method shown in Reaction Scheme 1 below.

[Reaction Scheme 1]

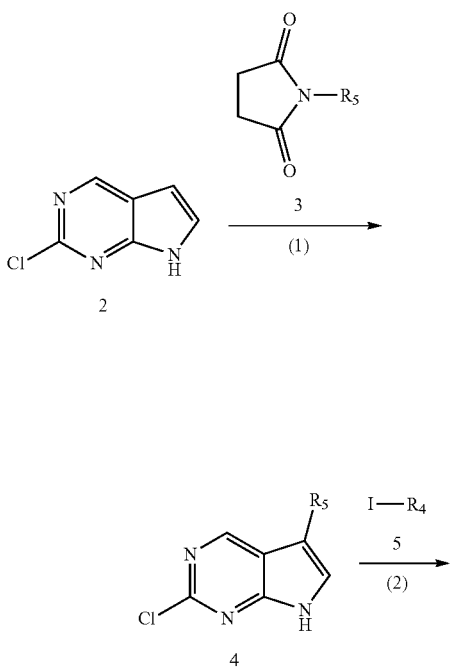

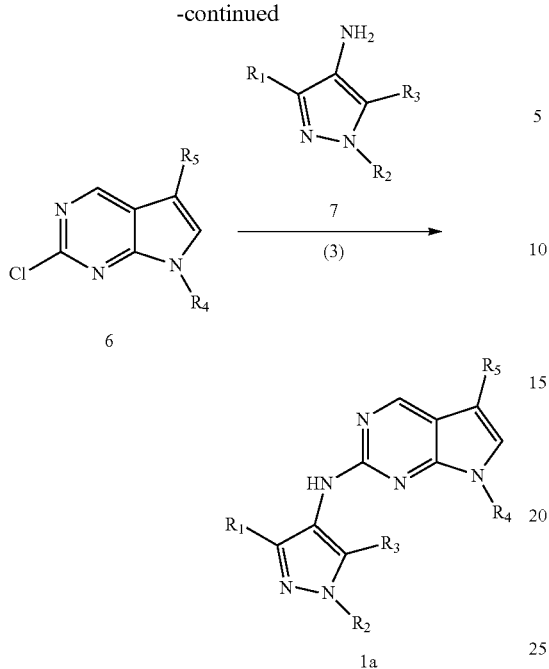

In Reaction Scheme 1, $R_1$ to $R_5$ are as defined in Formula 1 above.

Specifically, the compound of Formula 1a may be prepared by a process, which comprises (1) reacting a compound of Formula 2 with a compound of Formula 3 in an organic solvent to prepare a compound of Formula 4; (2) reacting the compound of Formula 4 with a compound of Formula 5 in an organic solvent to prepare a compound of Formula 6; and (3) reacting the compound of Formula 6 with a compound of Formula 7 in an organic solvent to prepare the compound of Formula Ta.

The organic solvent may be at least one selected from the group consisting of acetone, 1,4-dioxane, methyl ethyl ketone, N,N-dimethylformamide, N-methylpyrrolidone, and ethyl acetate, but it is not limited thereto.

In step (1), for example, a compound of Formula 2 may be reacted with N-chlorosuccinimide (NCS) in an N,N-dimethylformamide solvent for 1 to 2 hours at room temperature to prepare a compound of Formula 4.

In step (2), for example, the compound of formula 4 may be reacted with potassium hydroxide and a compound of Formula 5 in an N,N-dimethylformamide solvent for 2 hours at room temperature to prepare a compound of Formula 6.

Alternatively, unlike steps (1) and (2) above, after the compound of Formula 2 is reacted with iodine and potassium hydroxide in an N,N-dimethylformamide solvent at 0° C. to room temperature, iodomethane is added thereto, followed by reaction with methyl fluorosulfonyldifluoroacetate (MFSDA) at 100 to 130° C. for 4 hours to prepare 2-chloro-7-methyl-5-(trifluoromethyl)-7H-pyrrolo[2,3-d]pyrimidine.

In step (3), for example, after the compound of Formula 6 and a compound of Formula 7 are dissolved in an ethanol solvent, hydrochloric acid is added thereto, which is reacted at 80° C. for 12 hours to prepare a compound of Formula 1a.

Alternatively, palladium (II) acetate (0.1 to 0.5 eq.), Xantphos (0.5 to 1.0 eq.), potassium carbonate (2 to 3 eq.), compounds 6 and 7 are reacted in an organic solvent such as 1,4-dioxane at 80 to 110° C. for 10 to 12 hours to prepare the compound of Formula Ta.

The compound of Formula 1b (where X is N) according to an embodiment may be prepared by the method as shown in Reaction Scheme 2 below.

[Reaction Scheme 2]

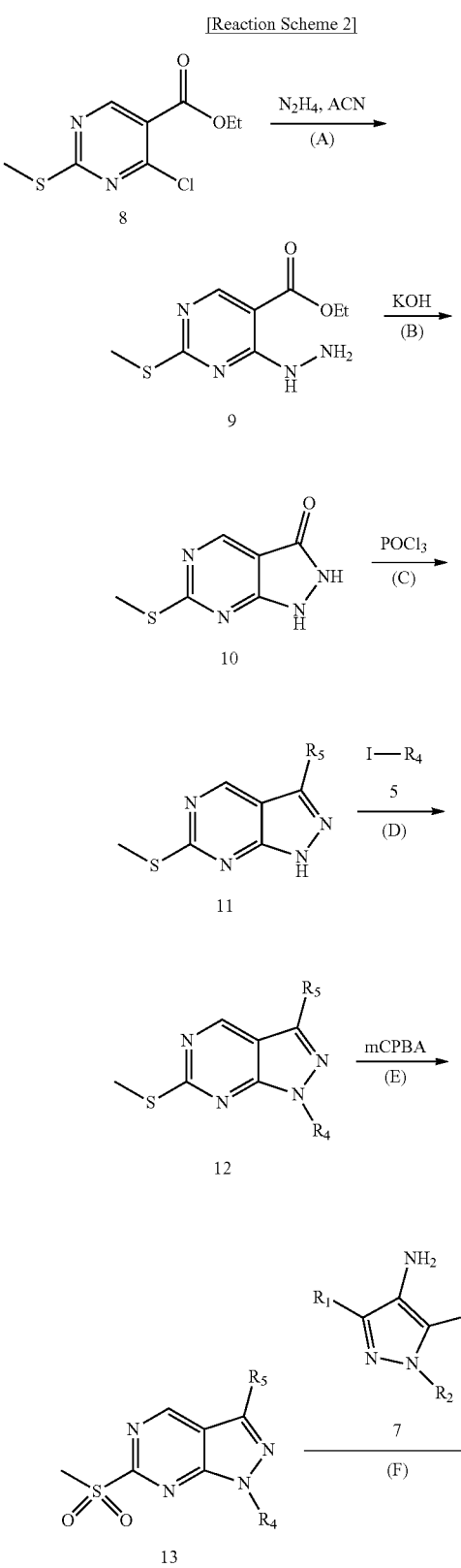

-continued

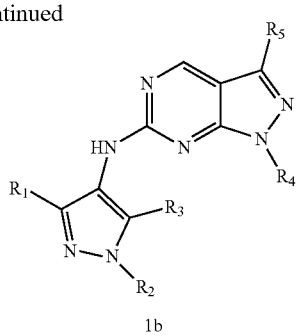

1b

In Reaction Scheme 2, $R_1$ to $R_5$ are as defined in Formula 1 above.

Specifically, the compound of Formula 1b may be prepared by a process, which comprises (A) reacting a compound of Formula 8 with $N_2H_4$ and acetonitrile (ACN) to prepare a compound of Formula 9; (B) reacting the compound of Formula 9 with KOH to prepare a compound of Formula 10; (C) reacting the compound of Formula 10 with phosphoryl chloride ($POCl_3$) to prepare a compound of Formula 11; (D) reacting the compound of Formula 11 with a compound of Formula 5 in an organic solvent to prepare a compound of Formula 12; (E) reacting the compound of Formula 12 with m-chloroperoxybenzoic acid (mCPBA) in an organic solvent to prepare a compound of Formula 13; and (F) reacting the compound of Formula 13 with p-toluenesulfonic acid and a compound of Formula 7 in an organic solvent to prepare the compound of Formula 1b.

The organic solvent may be at least one selected from the group consisting of acetone, dichloromethane, 1,4-dioxane, methyl ethyl ketone, N,N-dimethylformamide, N-methylpyrrolidone, and ethyl acetate, but it is not limited thereto.

In step (A), for example, a compound of Formula 8 may be reacted with $N_2H_4$ and acetonitrile (ACN) for 1 to 2 hours at room temperature to prepare a compound of Formula 9.

In step (B), for example, the compound of Formula 9 may be reacted with 10% KOH at 90 to 110° C. for 2 to 3 hours to prepare a compound of Formula 10.

In step (C), for example, the compound of Formula 10 may be reacted with phosphoryl chloride ($POCl_3$) at 90 to 110° C. to prepare a compound of Formula 11.

In step (D), for example, the compound of formula 11 may be reacted with a compound of Formula 5 in an N,N-dimethylformamide solvent at 0° C. to room temperature for 2 hours to prepare a compound of Formula 12.

In step (E), for example, the compound of Formula 12 may be reacted with m-chloroperoxybenzoic acid (mCPBA) in a dichloromethane or N,N-dimethylformamide solvent at room temperature for 4 hours to prepare a compound of Formula 13.

In step (F), for example, the compound of formula 13 may be reacted with p-toluenesulfonic acid and a compound of Formula 7 in an N-methylpyrrolidone solvent at 100 to 120° C. for 6 hours to prepare the compound of Formula 1b.

For the synthesis of the compounds of Formulae 10 and 11, reference was made to the literature (Hauser, Martin. et al., J. Org. Chem. 1960, 25, 1570-1573; J. Org. Chem. 1961, 26, 451-455; and Liu, Jing. et al., ACS Comb. Sci. 2011, 13, 414-420).

The compound represented by Formula 1 according to an embodiment, and a pharmaceutically acceptable salt, hydrate, solvate, prodrug, and isomer thereof have a high inhibitory activity to LRRK2, as well as excellent selectivity for other kinases. Thus, the compound represented by Formula 1 and a pharmaceutically acceptable salt, hydrate, solvate, prodrug, and isomer thereof are useful as a drug for preventing or treating a degenerative brain disease that requires inhibition of LRRK2 activity.

One embodiment provides a pharmaceutical composition for preventing or treating a degenerative brain disease, which comprises the compound as an active ingredient.

According to an embodiment, the degenerative brain disease may be Parkinson's disease.

According to an embodiment, the pharmaceutical composition has an inhibitory activity selective to LRRK2 (leucine-rich repeat kinase 2).

According to an embodiment, the pharmaceutical composition may comprise one or more pharmaceutically acceptable additives. For example, lubricants such as magnesium stearate, sodium lauryl sulfate, and talc; excipients such as lactose, sodium citrate, calcium carbonate, and dicalcium phosphate; disintegrants such as starch, alginic acid, and specific complex silicates; and various carriers may be used for the preparation of tablets. In addition, the type of carrier may vary depending on the solubility, chemical properties, and mode of administration of the active ingredient.

The pharmaceutical composition may be prepared according to conventional methods using one or more pharmaceutically acceptable additives. The additives may include, in particular, diluents, sterilized aqueous media, and various non-toxic organic solvents. If necessary, sweeteners, fragrances, colorants, or stabilizers may be further comprised.

The pharmaceutical composition may be formulated in various dosage forms such as tablets, pills, granules, capsules, powders, aqueous solutions, or suspensions, injection solutions, elixirs, or syrups according to conventional formulation methods in the pharmaceutical field.

In order to prepare capsules, it is advantageous to use lactose and high molecular weight polyethylene glycol. If aqueous suspensions are used, they may contain emulsifiers or agents that facilitate suspension. Such diluents as sucrose, ethanol, polyethylene glycol, propylene glycol, glycerol, chloroform, or mixtures thereof may also be used.

As such, the pharmaceutical composition may be administered non-orally or orally as needed. It may be administered in single or multiple doses once a day. The non-oral dose range is from 0.5 mg/kg to 5 mg/kg per body weight, preferably 1 mg/kg to 4 mg/kg per body weight; of the oral dose range is form 5 mg/kg to 50 mg/kg per body weight, preferably 10 mg/kg to 40 mg/kg per body weight. The dosage for patients may vary depending on body weight, age, sex, health status, diet, administration time, administration method, excretion rate, and severity of the disease for each patent.

According to an embodiment, there is provided a use of the compound for the preparation of a medicament for preventing or treating a degenerative brain disease.

According to an embodiment, there is provided a method of treating a degenerative brain disease, which comprises administering the compound to a patient.

Hereinafter, the present invention will be described in more detail with reference to the following examples. However, these examples are provided to illustrate the present invention with specific embodiments. It is not intended to limit the scope of the present invention to the those described therein.

Preparation Example 1: Synthesis of Intermediate 1 (2,5-dichloro-7-methyl-7H-pyrrolo[2,3-d]pyrimidine)

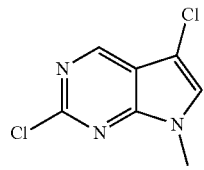

2,5-Dichloro-7H-pyrrolo[2,3-d]pyrimidine (2.16 g, 11.48 mmol) was added to an N,N-dimethylformamide solvent (20 ml), which was cooled to 0° C. NaH (0.68 g, 17.23 mmol) was slowly added thereto, followed by stirring thereof at 0° C. for 30 minutes. Iodomethane (1.59 ml, 17.23 mmol) was slowly added thereto dropwise, followed by elevation of the temperature to room temperature and stirring thereof for 2 hours. Water (50 ml) was added to precipitate a solid. It was filtered with water under reduced pressure and washed with n-heptane to obtain 2.20 g (yield: 94%) of the target compound as a solid in beige color.

MS (ESI) m/z 201.9, 204.1 [M+H]$^+$;
$^1$H NMR (300 MHz, CDCl$_3$) δ 8.95 (s, 1H), 7.88 (s, 1H), 3.77 (s, 3H).

Preparation Example 2: Synthesis of Intermediate 2 (2,5-dichloro-7-ethyl-7H-pyrrolo[2,3-d]pyrimidine)

2,5-Dichloro-7H-pyrrolo[2,3-d]pyrimidine (3.31 g, 17.60 mmol) was added to an N,N-dimethylformamide solvent (33 ml), which was cooled to 0° C. NaH (1.15 g, 26.40 mmol) was slowly added thereto, followed by stirring thereof at 0° C. for 30 minutes. Iodomethane (1.69 ml, 21.12 mmol) was slowly added thereto dropwise, followed by elevation of the temperature to room temperature and stirring thereof for 2 hours. Water (80 ml) was added to precipitate a solid. It was filtered with water under reduced pressure to obtain 3.15 g (yield: 82%) of the target compound.

MS (ESI) m/z 216.0, 217.8 [M+H]$^+$;
$^1$H NMR (300 MHz, DMSO-d$_6$) δ 8.92 (s, 1H), 7.96 (s, 1H), 4.21 (q, J=7.2 Hz, 2H), 1.38 (t, J=7.2 Hz, 3H).

Preparation Example 3: Synthesis of Intermediate 3 (2,5-dichloro-7-(2,2,2-trifluoroethyl)-7H-pyrrolo[2,3-d]pyrimidine)

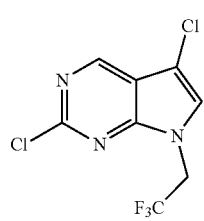 [SMILES: FC(F)(F)Cn1cc(Cl)c2cnc(Cl)nc21]

2,5-Dichloro-7H-pyrrolo[2,3-d]pyrimidine (900 mg, 4.79 mmol), cesium carbonate (Cs$_2$CO$_3$, 1.9 g, 5.7 mmol), and 1,1,1-trifluoro-2-iodoethane (9.58 mmol, 0.94 ml) were added to an N,N-dimethylformamide solvent (50 ml), which was stirred at 100° C. for 12 hours. It was extracted with water and dichloromethane (DCM), which was depressurized and subjected to column chromatography (EA:Hep=1:1) to obtain 1.0 g of the target compound (yield: 77%).

MS (ESI) m/z 269.8 [M+H]$^+$;
$^1$H NMR (300 MHz, CDCl$_3$) δ 8.89 (s, 1H), 7.279 (s, 1H), 4.84 (q, J=8.4 Hz, 2H).

Preparation Example 4: Synthesis of Intermediate 4 (2,5-dichloro-7-isopropyl-7H-pyrrolo[2,3-d]pyrimidine)

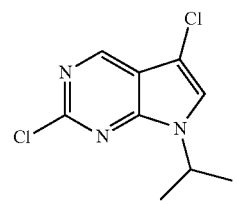

2,5-Dichloro-7H-pyrrolo[2,3-d]pyrimidine (1.0 g, 5.31 mmol) was added to an N,N-dimethylformamide solvent (10 ml), which was cooled to 0° C. NaH (0.32 g, 7.97 mmol) was slowly added thereto, followed by stirring thereof at 0° C. for 30 minutes. 2-Iodopropane (0.79 ml, 7.97 mmol) was slowly added thereto dropwise, followed by elevation of the temperature to room temperature and stirring thereof for 2 hours. Water (30 ml) was added at room temperature to precipitate a solid. It was filtered with water under reduced pressure to obtain 1.05 g of the target compound (yield: 85%).

MS (ESI) m/z 230.0, 232.0 [M+H]$^+$;
$^1$H NMR (300 MHz, CDCl$_3$) δ 8.85 (s, 1H), 7.82 (s, 1H), 5.09 (p, J=6.9 Hz, 1H), 1.57 (s, 3H), 1.55 (s, 3H).

Preparation Example 5: Synthesis of Intermediate 5 (2,5-dichloro-7-cyclopropyl-7H-pyrrolo[2,3-d]pyrimidine)

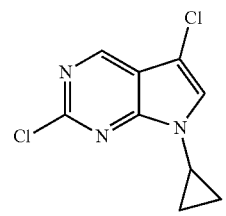 [SMILES: Clc1ncc2c(Cl)cn(C3CC3)c2n1]

2,5-Dichloro-7H-pyrrolo[2,3-d]pyrimidine (0.2 g, 1.06 mmol) was added to an N,N-dimethylformamide solvent (10 ml), which was cooled to 0° C. NaH (69.6 mg, 1.59 mmol) was slowly added thereto, followed by stirring thereof at 0° C. for 30 minutes. Cyclopropanecarbonyl chloride (0.11 ml, 1.27 mmol) was slowly added thereto dropwise, followed by elevation of the temperature to room temperature and stirring thereof for 2 hours. Water (30 ml) was added at room temperature to precipitate a solid. It was filtered with water under reduced pressure to obtain 0.23 g of the target compound (yield: 87%).

MS (ESI) m/z 255.9, 258.1 [M+H]+;
1H NMR (300 MHz, CDCl3) δ 8.90 (s, 1H), 7.98 (s, 1H), 3.85-3.79 (m, 1H), 1.43-1.40 (m, 2H), 1.33-1.30 (m, 2H).

Preparation Example 6: Synthesis of Intermediate 6 (2-chloro-7-methyl-5-(trifluoromethyl)-7H-pyrrolo[2,3-d]pyrimidine)

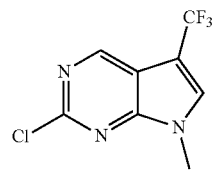

Step 1: Synthesis of 2-chloro-5-iodo-7H-pyrrole[2,3-d]pyrimidine

2-Chloro-7H-pyrrole[2,3-d]pyrimidine (1.0 g, 6.51 mmol) was dissolved in an N,N-dimethylformamide solvent (10 ml), which was cooled to 0° C. Potassium hydroxide (1.37 g, 24.41 mmol) and iodine (3.3 g, 13.02 mmol) were slowly added thereto, followed by gradual elevation of the temperature to room temperature. After it was stirred for 2 hours, water (80 ml) was added thereto to terminate the reaction, and a solid was precipitated. It was filtered with water under reduced pressure and washed with ethyl acetate (EtOAc) to obtain 1.68 g of the target compound as a solid in yellow color (yield: 89%).
MS (ESI) m/z 279.8, 281.8 [M+H]+;
1H NMR (300 MHz, CDCl3) δ 8.37 (s, 1H), 7.64 (s, 1H).

Step 2: Synthesis of 2-chloro-5-iodo-7-methyl-7H-pyrrole[2,3-d]pyrimidine

2-Chloro-5-iodo-7H-pyrrole[2,3-d]pyrimidine (1 g, 3.57 mmol) was dissolved in an N,N-dimethylformamide solvent (5 ml), which was cooled to 0° C. NaH (0.21 g, 5.36 mmol) was slowly added thereto, followed by stirring thereof at 0° C. for 30 minutes. Iodomethane (0.49 ml, 5.36 mmol) was slowly added thereto dropwise, followed by elevation of the temperature to room temperature and stirring thereof for 2 hours. Water (10 ml) was added to precipitate a solid. It was filtered with water under reduced pressure and washed with n-heptane to obtain 0.60 g of the target compound as a solid in beige color (yield: 57%).
MS (ESI) m/z 236.1 [M+H]+;
1H NMR (300 MHz, CDCl3) δ 8.60 (s, 1H), 7.29 (s, 1H), 3.88 (s, 3H).

Step 3: Synthesis of Intermediate 6

2-Chloro-5-iodo-7-methyl-7H-pyrrole[2,3-d]pyrimidine (0.5 g, 1.70 mmol) was dissolved in an N,N-dimethylformamide solvent (10 ml). Methyl 2,2-difluoro-2-(fluorosulfonyl)acetate (0.53 ml, 4.25 mmol) and Cu(I)I (0.32 g, 1.70 mmol) were added thereto, which was stirred at 130° C. for 2 hours. The temperature was lowered to room temperature, ethyl acetate (50 ml) was added thereto, and water (30 ml) was added thereto to terminate the reaction. It was filtered with celite, extracted with ethyl acetate and water, and washed with brine. The organic layer was dried over MgSO4, filtered under reduced pressure, and concentrated. It was subjected to column chromatography to obtain 0.12 g of the target compound (yield: 310%).
MS (ESI) m/z 235.9, 238.0 [M+H]+;
1H NMR (300 MHz, CDCl3) δ 8.96 (s, 1H), 7.57 (s, 1H), 3.90 (s, 3H).

Preparation Example 7: Synthesis of Intermediate 7 (3-chloro-1-methyl-6-(methylthio)-1H-pyrazolo[3,4-d]pyrimidine)

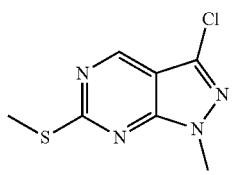

Step 1: Synthesis of ethyl 4-hydrazinyl-2-(methylthio)pyrimidin-5-carboxylate Ethanol (5.5 ml) was added to ethyl 4-chloro-2-(methylthio)pyrimidin-5-carboxylate (1.3 g, 5.58 mmol), which was cooled to 0° C. Methyl hydrazine (0.58 ml, 11.17 mmol) dilute in ethanol (5.5 ml) was slowly added thereto, which was stirred at room temperature for 2 hours. Water (30 ml) was added thereto to terminate the reaction, and a white solid was precipitated. It was filtered under reduced pressure to obtain 0.86 g of the target compound (yield: 64%).
MS (ESI) m/z 243.3 [M+H]+;
1H NMR (300 MHz, CDCl3) δ 8.33 (s, 1H), 4.33 (q, J=7.2 Hz, 2H), 4.17 (s, 2H), 3.40 (s, 3H), 2.53 (s, 3H), 1.37 (t, J=7.2 Hz, 3H).

Step 2: Synthesis of 6-(methylthio)-1H-pyrazolo[3,4-d]pyrimidin-3(2H)-one

Ethyl 4-hydrazinyl-2-(methylthio)pyrimidin-5-carboxylate (0.86 g, 3.54 mmol) was added to 10% KOH (9.0 ml), which was refluxed at 100° C. for 15 minutes. After the temperature was lowered to room temperature, a 25% aqueous acetic acid solution (8 ml) was added thereto for neutralization, thereby precipitating a yellow solid. It was filtered with water under reduced pressure to obtain 0.58 g of the target compound (yield: 84%).
MS (ESI) m/z 197.0 [M+H]+;
1H NMR (300 MHz, DMSO-d6) δ 11.59 (s, 1H), 8.86 (s, 1H), 3.72 (s, 3H), 2.56 (s, 3H).

Step 3: Synthesis of Intermediate 7

A suction flask was charged with 6-(methylthio)-1H-pyrazolo[3,4-d]pyrimidin-3(2H)-one (0.58 g, 2.95 mmol), and POCl3 (2.34 ml, 25.12 mmol) was added thereto, which was stirred at 140° C. for 5 hours. After the temperature was lowered to room temperature, ammonium hydroxide (20 ml) was slowly added thereto at 0° C. for neutralization, thereby precipitating a beige solid. It was filtered with water under reduced pressure and washed with a solution of ethanol and water (1:1) to obtain 0.50 g of the target compound (yield: 79%).
MS (ESI) m/z 214.9, 216.9 [M+H]+;
1H NMR (300 MHz, CDCl3) δ 8.87 (s, 1H), 4.02 (s, 2H), 2.66 (s, 3H).

Preparation Example 8: Synthesis of Intermediate 8 (3-chloro-1-ethyl-6-(methylthio)-1H-pyrazolo[3,4-d]pyrimidine)

3-Chloro-6-(methylthio)-1H-pyrazolo[3,4-d]pyrimidine (12.7 g, 63.29 mmol) was dissolved in an N,N-dimethylformamide solvent (63 ml), which was cooled to 0° C. NaH (3.31 g, 75.95 mmol) was slowly added thereto, followed by stirring thereof at 0° C. for 30 minutes. Iodomethane (6.10 ml, 75.95 mmol) was slowly added thereto, followed by elevation of the temperature to room temperature and stirring thereof for 2 hours. After the reaction was terminated, water (100 ml) was added to precipitate a brown solid. It was filtered and dried under reduced pressure to obtain 12.26 g of the target compound (yield: 84%).

MS (ESI) m/z 228.70 [M+H]$^+$;

$^1$H NMR (300 MHz, CDCl$_3$) δ 8.86 (s, 1H), 4.44 (q, J=7.2 Hz, 2H), 2.65 (s, 3H), 1.53 (t, J=7.2 Hz, 3H).

Preparation Example 9: Synthesis of Intermediate 9 (3-chloro-6-(methylthio)-1-(2,2,2-trifluoroethyl)-1H-pyrazolo[3,4-d]pyrimidin)

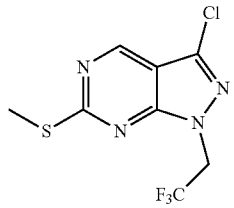 [SMILES: CSc1ncc2c(Cl)nn(CC(F)(F)F)c2n1]

3-Chloro-6-(methylthio)-1H-pyrazolo[3,4-d]pyrimidine (70 mg, 0.49 mmol) was dissolved in an N,N-dimethylformamide solvent (63 ml). Cesium carbonate (243 mg, 0.74 mmol) and 2,2,2-trifluoroethyl methanesulfonate (70.0 ml, 0.59 mmol) were added thereto, which was stirred at 80° C. for 5 hours. The temperature was lowered to room temperature, and it was extracted with water and ethyl acetate. The organic layer was dried over MgSO$_4$, filtered under reduced pressure, and concentrated. It was subjected to column chromatography to obtain 48.3 mg of the target compound (yield: 48%).

MS (ESI) m/z 282.8, 285.0 [M+H]$^+$;

$^1$H NMR (300 MHz, Acetone-d$_6$) δ 9.09 (s, 1H), 5.27 (q, J=8.7 Hz, 2H), 2.66 (s, 3H).

Preparation Example 10: Synthesis of Intermediate 10 (3-chloro-1-cyclopropyl-6-(methylthio)-1H-pyrazolo[3,4-d]pyrimidine)

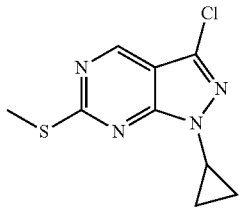

A suction flask was charged with 3-chloro-6-(methylthio)-1H-pyrazolo[3,4-d]pyrimidine (0.2 g, 0.99 mmol), cycloboronic acid (0.17 g, 1.99 mmol), 2,2'-bipyridine (0.15 g, 0.99 mmol), and Na$_2$CO$_3$ (0.21 g, 1.99 mmol). Dichloroethane (10 ml) was added thereto, and nitrogen (N$_2$) was bubbled for 10 minutes. Cu(OAc)$_2$ (0.18 g, 0.99 mmol) was added thereto, and N$_2$ was bubbled for 1 minute, which was stirred at 60° C. for 18 hours. The temperature was lowered to room temperature, and it was filtered with ethyl acetate and then concentrated. It was extracted with ethyl acetate and a 1N aqueous hydrochloric acid solution, dried over MgSO$_4$, filtered under reduced pressure, and concentrated. It was subjected to column chromatography to obtain 0.16 g of the target compound (yield: 67%).

MS (ESI) m/z 241.1, 243.2 [M+H]$^+$;

$^1$H NMR (300 MHz, CDCl$_3$) δ 8.84 (s, 1H), 3.82-3.75 (m, 1H), 2.67 (s, 3H), 1.36-1.33 (m, 2H), 1.18-1.14 (m, 2H).

Preparation Example 11: Synthesis of Intermediate 11 (1-isopropyl-3-methoxy-1H-pyrazol-4-amine)

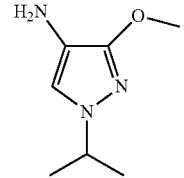

Step 1: Synthesis of 1-nitro-1H-pyrazole

HNO$_3$ (18 ml) was slowly added to acetic anhydride (42 ml) at 0° C. to prepare acetyl nitrate. Another flask was charged with 1H-pyrazole (10 g), and acetic acid (28 ml) was added thereto. The acetyl nitrate was slowly added to the pyrazole compound at 0° C., followed by stirring thereof for 1 hour and the addition of water to precipitate a solid. It was filtered with water under reduced pressure to obtain 16.0 g of the target compound (yield: 97%).

$^1$H NMR (300 MHz, CDCl$_3$) δ 8.79 (t, J=3.3 Hz, 1H), 7.88 (d, J=0.6 Hz, 1H).

Step 2: Synthesis of 3-nitro-1H-pyrazole

1-Nitro-1H-pyrazole (10 g) was dissolved in benzonitrile (70 ml), which was refluxed at 180° C. for 4 hours. The temperature was lowered to room temperature to precipitate a solid. Heptane (250 ml) was added thereto, which was stirred for 10 minutes, followed by filtration under reduced pressure to obtain 8.9 g of the target compound (yield: 89%).

$^1$H NMR (300 MHz, CDCl$_3$) δ 12.80 (br s, 1H), 7.87 (d, J=2.4 Hz, 1H), 7.04 (t, J=1.2 Hz, 1H).

Step 3: Synthesis of 3,4-dinitro-1H-pyrazole

3-Nitro-1H-pyrazole (2.5 g, 22.11 mmol) was dissolved in H$_2$SO$_4$ (7.6 ml, 143.71 mmol), which was cooled to 0° C. Fuming nitric acid (fuming HNO$_3$, 1.03 ml, 24.32 mmol) was slowly added thereto, followed by stirring thereof at 80° C. for 4 hours. The temperature was lowered to 0° C., and it was neutralized with NaHCO$_3$. It was extracted with ethyl acetate, dried over MgSO$_4$, filtered under reduced pressure, and concentrated. It was subjected to column chromatography to obtain 0.80 g of the target compound (yield: 22%).

MS (ESI) m/z 159.1 [M+H]$^+$;

$^1$H NMR (300 MHz, CDCl$_3$) δ 9.12 (s, 1H).

Step 4: Synthesis of 1-isopropyl-3,4-dinitro-1H-pyrazole 3,4-Dinitro-1H-pyrazole (0.8 g, 5.06 mmol) was dissolved in dimethylformamide (DMF, 10 ml), which was cooled to 0° C. NaH (0.30 g, 7.59 mmol) was slowly added thereto, followed by stirring thereof for 30 minutes. 2-Iodopropane (0.75 ml, 7.59 mmol) was added thereto dropwise, followed by stirring thereof at room temperature for 1 hour. Water was added thereto to terminate the reaction, and it was extracted with ethyl acetate. It was dried over MgSO$_4$, filtered under reduced pressure, and concentrated. It was subjected to column chromatography to obtain 0.31 g of the target compound (yield: 30%).

MS (ESI) m/z 201.0 [M+H]$^+$;

$^1$H NMR (300 MHz, CDCl$_3$) δ 8.19 (s, 1H), 4.58 (q, J=6.9 Hz, 1H), 1.64 (s, 3H), 1.61 (s, 3H).

Step 5: Synthesis of 1-isopropyl-3-methoxy-4-nitro-1H-pyrazole

1-Isopropyl-3,4-dinitro-1H-pyrazole (0.31 g, 1.54 mmol) was dissolved in MeOH, and NaOMe (0.78 g, 3.09 mmol) was added thereto. After it was refluxed for 6 hours, the temperature was lowered to room temperature, and it was extracted with water and ethyl acetate. It was dried over MgSO$_4$, filtered under reduced pressure, and concentrated. It was subjected to column chromatography to obtain 0.26 g of the target compound (yield: 92%).

MS (ESI) m/z 186.0 [M+H]$^+$;

$^1$H NMR (300 MHz, CDCl$_3$) δ 8.03 (s, 1H), 4.32 (p, J=6.6 Hz, 1H), 4.06 (s, 3H), 1.53 (s, 3H), 1.51 (s, 3H).

Step 6: Synthesis of Intermediate 11

1-Isopropyl-3-methoxy-4-nitro-1H-pyrazol (0.26 g, 1.40 mmol) was dissolved in MeOH, and 10 wt % Pd/C (37.75 mg, 0.03 mmol) was slowly added thereto. It was stirred for 14 hours under H$_2$ conditions. It was filtered with Celite, concentrated, and subjected to column chromatography to obtain 0.16 g of the target compound (yield: 75%).

MS (ESI) m/z 201.0 [M+H]$^+$;

$^1$H NMR (300 MHz, CDCl$_3$) δ 6.95 (s, 1H), 4.20 (q, J=6.6 Hz, 1H), 3.93 (s, 3H), 1.41 (s, 3H), 1.39 (s, 3H).

Preparation Example 12: Synthesis of Intermediate 12 (4-nitro-3-(trifluoromethyl)-1H-pyrazole)

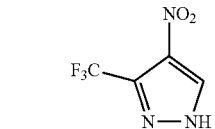

3-(Trifluoromethyl)-1H-pyrazole (2 g, 14.69 mmol) and H$_2$SO$_4$ (9.36 g, 95.53 mmol) were added, which was stirred in an ice bath. HNO$_3$ (1.01 g, 16.16 mmol) was added thereto, followed by stirring thereof at 80° C. for 4 hours. Upon termination of the reaction, ice was added thereto, followed by stirring thereof. The resulting solid compound was filtered first, and the filtrate was extracted again with ethyl acetate, dried over MgSO$_4$, and depressurized to obtain 2.60 g of a white solid compound (yield: 97%).

$^1$H NMR (300 MHz, CDCl$_3$) δ 8.46 (s, 1H).

Preparation Example 13: Synthesis of Intermediate 13 (1-(tetrahydro-2H-pyran-4-yl)-3-(trifluoromethyl)-1H-pyrazol-4-amine)

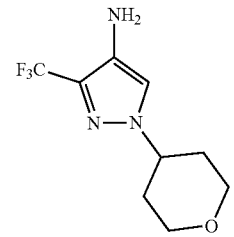 [SMILES: Nc1cn(C2CCOCC2)nc1C(F)(F)F]

Step 1: Synthesis of tetrahydro-2H-pyran-4-ol

Dihydro-2H-pyran-4(3H)-one (1 g, 9.98 mmol) was added to tetrahydrofuran (THF, 10 ml), which was stirred for 10 minutes in an ice bath. LiAlH$_4$ (2 M in THF, 10 ml) was added thereto dropwise, followed by stirring thereof for 3 hours. Upon termination of the reaction, it was immersed in 2 N NaOH. NH$_4$Cl was added thereto, which was stirred and then filtered. The solution was evaporated under reduced pressure, and isopropyl ether (IPE) was added thereto, which was stirred and then filtered. The filtrate was depressurized again to obtain 0.18 g of the target compound (yield: 18%).

$^1$H NMR (300 MHz, CDCl$_3$) δ 3.54-3.47 (m, 4H), 1.25-1.20 (m, 5H).

Step 2: Synthesis of tetrahydro-2H-pyran-4-yl methanesulfonate

Tetrahydro-2H-pyran-4-ol (0.18 g, 1.82 mmol) and DCM (15 ml) were added, which was stirred for 10 minutes in an ice bath. Methanesulfonyl chloride (0.31 g, 2.73 mmol) and triethylamine (TEA, 0.27 g, 2.73 mmol) were added thereto, which was stirred for 7 hours. Upon termination of the reaction, it was extracted, dried over MgSO$_4$, and depressurized to obtain 0.20 g of the target compound (yield: 62%).

$^1$H NMR (300 MHz, CDCl$_3$) δ 4.97-4.88 (m, 1H), 4.00-3.93 (m, 2H), 3.61-3.53 (m, 2H), 3.06 (s, 3H), 2.11-2.03 (m, 2H), 1.96-1.84 (m, 2H).

Step 3: Synthesis of 4-nitro-1-(tetrahydro-2H-pyran-4-yl)-3-(trifluoromethyl)-1H-pyrazole 4-Nitro-3-(trifluoromethyl)-1H-pyrazole (0.1 g, 0.55 mmol, Intermediate 12), DMF (13 ml), and $Cs_2CO_3$ (0.27 g, 0.82 mmol) were added and stirred for 30 minutes. Tetrahydro-2H-pyran-4-yl methanesulfonate (0.13 g, 0.82 mmol) was added thereto, which was refluxed for 2 hours. Upon termination of the reaction, the solution was evaporated under reduced pressure, and it was extracted with ethyl acetate. After it was dried over $MgSO_4$, the solution was evaporated under reduced pressure, and it was subjected to column chromatography (MC:MeOH=10:1) to obtain 0.045 g of the target compound (yield: 31%).

Step 4: Synthesis of Intermediate 13

4-Nitro-1-(tetrahydro-2H-pyran-4-yl)-3-(trifluoromethyl)-1H-pyrazole (0.045 g, 0.17 mmol) and THF:MeOH (7 ml, 10:1 v/v) were added, which was stirred for 10 minutes in an ice bath. $Ni(OAc)_2 \cdot 4H_2O$ (0.0042 g, 0.016 mmol) and $NaBH_4$ (0.025 g, 0.67 mmol) were added thereto, which was stirred for 30 minutes. Upon termination of the reaction, it was filtered, and the solution was evaporated under reduced pressure. It was subjected to column chromatography (MC:MeOH=10:1) to obtain 0.039 g of the target compound (yield: 98%).

MS (ESI) m/z 236.0 $[M+H]^+$

Preparation Example 14: Synthesis of Intermediate 14 (1-isopropyl-3-(trifluoromethyl)-1H-pyrazol-4-amine)

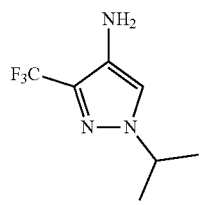

Step 1: Synthesis of 1-isopropyl-4-nitro-3-(trifluoromethyl)-1H-pyrazole

4-Nitro-3-(trifluoromethyl)-1H-pyrazole (0.10 g, 0.58 mmol, Intermediate 12) and DMF (15 ml) were added and stirred for 10 minutes in an ice bath. NaH (0.038 g, 0.87 mmol) was added thereto, followed by stirring thereof for 30 minutes. 2-Iodopropane (0.13 g, 0.76 mmol) was added thereto, followed by refluxing thereof for 3 hours. Upon termination of the reaction, the solution was evaporated under reduced pressure, and it was extracted with ethyl acetate. After it was dried over $MgSO_4$, the solution was depressurized, and it was subjected to column chromatography (Hep:EA=1:1) to obtain 0.09 g of the target compound (yield: 69%).

$^1$H NMR (300 MHz, $CDCl_3$) δ 8.28 (s, 1H), 4.64-4.55 (m, 1H), 1.59 (s, 6H).

Step 2: Synthesis of Intermediate 14

The same procedure as in steps 3 and 4 of Preparation Example 13 was carried out, except that 1-isopropyl-4-nitro-3-(trifluoromethyl)-1H-pyrazole was used instead of tetrahydro-2H-pyran-4-yl methanesulfonate, to obtain 0.09 g of the target compound (yield: 69%).

$^1$H NMR (300 MHz, $CDCl_3$) δ 7.06 (s, 1H), 4.49-4.38 (m, 1H), 3.19 (bs, 2H), 1.49 (s, 3H), 1.47 (s, 3H).

Preparation Example 15: Synthesis of Intermediate 15 (1-(2-methoxyethyl)-3-(trifluoromethyl)-1H-pyrazol-4-amine)

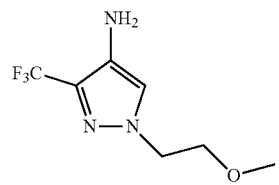

The same procedure as in Preparation Example 14 was carried out, except that 1-bromo-2-methoxyethane was used instead of 2-iodopropane, to obtain 0.14 g of the target compound (yield: 72%).

$^1$H NMR (300 MHz, $CDCl_3$) δ 7.14 (s, 1H), 4.22-4.19 (t, 2H, J=10.2 Hz), 3.73-3.71 (t, 2H, J=10.2 Hz), 3.36 (s, 3H), 3.19 (bs, 2H).

Preparation Example 16: Synthesis of Intermediate 16 (1-butyl-3-(trifluoromethyl)-1H-pyrazol-4-amine)

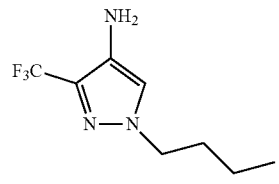

The same procedure as in Preparation Example 14 was carried out, except that 1-bromobutane was used instead of 2-iodopropane, to obtain 0.17 g of the target compound (yield: 93%).

$^1$H NMR (300 MHz, $CDCl_3$) δ 7.01 (s, 1H), 4.06-4.01 (t, 2H, J=14.7 Hz), 3.19 (s, 2H), 1.87-1.77 (m, 2H), 1.40-1.28 (m, 2H), 0.97-0.93 (t, 3H, J=14.7 Hz).

Preparation Example 17: Synthesis of Intermediate 17 (5-chloro-1-methyl-1H-pyrazol-4-amine)

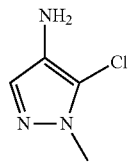

Step 1: Synthesis of 1-methyl-4-nitro-1H-pyrazole

4-Nitropyrazole (1.0 g, 8.84 mmol) was dissolved in DMF (10 ml). $K_2CO_3$ (3.6 g, 26.5 mmol) was added thereto, followed by stirring thereof for 30 minutes. Then, MeI (1.65 ml, 13.26 mmol) was added thereto. After overnight, it was filtered with K$_2$CO$_3$, and the solvent was concentrated. It was extracted with dichloromethane (DCM) and water, dried over MgSO$_4$, and then concentrated to obtain 0.82 g of the target compound (yield: 73%).

MS (ESI) m/z 128.1 [M+H]$^+$;

$^1$H NMR (300 MHz, DMSO-d$_6$) δ 8.84 (s, 1H), 8.23 (s, 1H), 3.91 (s, 3H).

Step 2: Synthesis of 5-chloro-1-methyl-4-nitro-1H-pyrazole

THF (20 ml) was added to 1-methyl-4-nitro-1H-pyrazole (1.0 g, 7.86 mmoles). After the temperature was lowered to −78° C., lithium bis(trimethylsilyl)amide (LiHMDS, 1 M in THF, 15.6 ml) was added thereto dropwise. After it was stirred for 30 minutes, hexachloroethane (2.79 g, 11.8 mmol) was added thereto. After it was stirred at room temperature for 1 hour, NaCl (10 ml) was added thereto to terminate the reaction. Then, it was extracted with ethyl acetate, dried over MgSO$_4$, and concentrated to obtain 1.1 g of the target compound (yield: 87%).

MS (ESI) m/z 162.2 [M+H]$^+$;

$^1$H NMR (300 MHz, DMSO-d$_6$) δ 8.14 (s, 3H), 3.91 (s, 3H).

Step 3: Synthesis of Intermediate 17

THF (50 ml) was added to 5-chloro-1-methyl-4-nitro-1H-pyrazole (1.1 g, 6.83 mmol). Ni(OAc)$_2$.4H$_2$O (169 mg, 0.68 mmol) was then added thereto. After the temperature was lowered to 0 to 4° C. using an ice bath, NaBH$_4$ (590 mg, 13.6 mmol) was added thereto in two portions. After it was stirred for 30 minutes and checked with TLC, aqueous NH$_4$Cl was added thereto to terminate the reaction, followed by extraction with ethyl acetate. After it was dried over MgSO$_4$, a solution (3.4 ml, 13.6 mmol) in which 4 M HCl was dissolved in dioxane was added thereto. After it was stirred for 30 minutes and concentrated, acetone was added for recrystallization to obtain 160 mg of the target compound (yield: 18%).

MS (ESI) m/z 132.0, 134.2 [M+H]$^+$;

$^1$H NMR (300 MHz, DMSO-d$_6$) δ 10.48 (brs, 2H), 7.68 (s, 1H), 3.81 (s, 3H).

Preparation Example 18: Synthesis of Intermediate 18 (5-chloro-1-(oxetan-3-yl)-1H-pyrazol-4-amine)

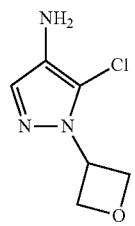

Step 1: Synthesis of 4-nitro-1-(oxetan-3-yl)-1H-pyrazole

4-Nitro-1H-pyrazole (0.66 g, 5.88 mmol) and oxetan-3-yl methanesulfonate (0.94 g, 6.17 mmol) were dissolved in DMF. Cs$_2$CO$_3$ (3.80 g, 11.67 mmol) was added thereto, followed by stirring thereof at 90° C. for 18 hours. The temperature was lowered to room temperature, and the reaction was then terminated with water. It was extracted with acetate and then dried over MgSO$_4$. It was filtered under reduced pressure, concentrated, and subjected to column chromatography to obtain 0.83 g of the target compound (yield: 84%).

MS (ESI) m/z 170.0 [M+H]$^+$

Step 2: Synthesis of 5-chloro-4-nitro-1-(oxetan-3-yl)-1H-pyrazole

THF (10 ml) was added to 4-nitro-1-(oxetan-3-yl)-1H-pyrazole (0.83 g, 4.90 mmol). After the temperature was lowered to −78° C., LiHMDS (1 M in THF, 9.81 ml) was added thereto dropwise. After it was stirred for 30 minutes, hexachloroethane (1.39 g, 5.88 mmol) dissolved in THF (5 ml) was added thereto. After it was stirred at −78° C. for 1 hour, aqueous NaCl (10 ml) was added thereto to terminate the reaction, followed by extraction with ethyl acetate. It was dried over MgSO$_4$, concentrated, and then subjected to column chromatography to obtain 0.42 g of the target compound (yield: 43%).

MS (ESI) m/z 204.1 [M+H]$^+$

Step 3: Synthesis of Intermediate 18

EtOH (20 ml) and water (2 ml) were added to 5-chloro-4-nitro-1-(oxetan-3-yl)-1H-pyrazole (0.42 g, 2.06 mmol). Fe (0.34 g, 6.18 mmol) and NH$_4$Cl (0.33 g, 6.18 mmol) were added thereto, followed by refluxing thereof at 90° C. for 3 hours. After the temperature was lowered to room temperature, it was filtered and concentrated under reduced pressure. Ethyl acetate was added thereto, and it was subjected to sonication for 3 minutes. After the insoluble material was filtered out, it was concentrated to obtain 0.34 g of the target compound (yield: 95%).

MS (ESI) m/z 173.9, 176.1 [M+H]$^+$

Preparation Example 19: Synthesis of Intermediate 19 (5-chloro-1-(4-chlorophenyl)-1H-pyrazol-4-amine)

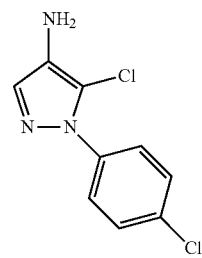 [SMILES: Nc1cnn(-c2ccc(Cl)cc2)c1Cl]

Step 1: Synthesis of 1-(4-chlorophenyl)-4-nitro-1H-pyrazole

4-Nitro-1H-pyrazole (1 g, 8.84 mmol), 4-chlorobenzeneboronic acid (2.76 g, 17.68 mmol) and Cu(OAc)$_2$ (2.40 g, 13.26 mmol) were added to DCM (40 ml). Pyridine (2.85 ml, 35.37 mmol) was added thereto, followed by stirring thereof at room temperature for 20 hours. Upon termination of the reaction, it was filtered and extracted with DCM and water. The organic layer was dried over MgSO$_4$ and filtered.

It was concentrated under reduced pressure and subjected to column chromatography to obtain 0.88 g of the target compound (yield: 44%).

Step 2: Synthesis of 5-chloro-1-(4-chlorophenyl)-4-nitro-1H-pyrazole

THF (6 ml) was added to 1-(4-chlorophenyl)-4-nitro-1H-pyrazole (0.64 g, 2.86 mmol). After the temperature was lowered to −78° C., LiHMDS (1 M in THF, 5.7 ml) was added thereto dropwise. After it was stirred for 30 minutes, hexachloroethane (0.81 g, 3.43 mmol) dissolved in THF (3 ml) was added thereto. After it was stirred at −78° C. for 1 hour, aqueous NaCl (10 ml) was added thereto to terminate the reaction. It was extracted with ethyl acetate, dried over MgSO$_4$, and concentrated. It was subjected to column chromatography to obtain 0.20 g of the target compound (yield: 27%).

MS (ESI) m/z 258.2, 260.0 [M+H]$^+$

Step 3: Synthesis of Intermediate 19

EtOH (15 ml) and water (1.5 ml) were added to 5-chloro-1-(4-chlorophenyl)-4-nitro-1H-pyrazole (0.20 g, 0.77 mmol). Fe (0.12 g, 2.32 mmol) and NH$_4$Cl (0.12 g, 2.32 mmol) were added thereto, followed by refluxing thereof at 90° C. for 3 hours. After the temperature was lowered to room temperature, it was filtered and concentrated under reduced pressure. Ethyl acetate was added thereto, and it was subjected to sonication for 3 minutes. After the insoluble material was filtered out, it was concentrated to obtain 0.17 g of the target compound (yield: 99%).

MS (ESI) m/z 228.0, 230.1 [M+H]$^+$

Preparation Example 20: Synthesis of Intermediate 20 (tert-butyl 4-(methylsulfonyloxy)piperidin-1-carboxylate)

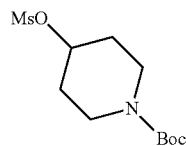

Tert-butyl-4-hydroxypiperidin-1-carboxylate (20.0 g, 99.42 mmol) was dissolved in DCM (200 ml). Methanesulfonyl chloride (10 ml, 1.3 eq.) was added thereto, followed by stirring thereof. Triethylamine (41.6 ml, 3.0 eq.) was added thereto, followed by stirring thereof for 1 hour. Upon termination of the reaction, it was extracted three times with brine and DCM, dried over MgSO$_4$, and concentrated under reduced pressure to obtain 27.7 g of a solid compound in ivory color (yield: 99%).

MS (ESI) m/z 280.1 [M+H]$^+$;
$^1$H NMR (300 MHz, CDCl$_3$) δ 4.95-4.54 (m, 1H), 3.74-3.70 (m, 2H), 3.35-3.28 (m, 2H), 3.05 (s, 3H), 1.96-1.84 (m, 4H), 1.48 (s, 9H).

Preparation Example 21: Synthesis of Intermediate 21 (tert-butyl 3-(methylsulfonyloxy)azetidin-1-carboxylate)

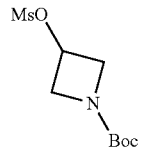

Step 1: Synthesis of tert-butyl-3-hydroxyazetidin-1-carboxylate

Azetidin-3-ol hydrochloride (3.0 g, 27.38 mmol) was dissolved in H$_2$O (6 ml). K$_2$CO$_3$ (3.78 g, 1.0 eq.) dissolved in H$_2$O (6 ml) was added thereto. Di-tert-butyl dicarbonate (5.98 g, 1.0 eq.) dissolved in THF (27 ml) was added thereto dropwise, followed by stirring thereof for 4 hours. Upon termination of the reaction, ethyl acetate was added thereto three times for extraction, it was dried and concentrated to obtain 4.7 g of the target compound in yellow color (yield: 99%).

MS (ESI) m/z 174.2 [M+H]$^+$;
$^1$H NMR (300 MHz, CDCl$_3$) δ 4.59-4.56 (m, 1H), 4.54-4.11 (m, 2H), 3.82-3.77 (m, 2H), 3.16 (s, 1H), 1.43 (s, 9H).

Step 2: Synthesis of Intermediate 21

Tert-butyl-3-hydroxyazetidin-1-carboxylate (4.7 g, 27.13 mmol) was dissolved in DCM (50 ml). Methanesulfonyl chloride (2.7 ml, 1.3 eq.) was added thereto, followed by stirring thereof. Triethylamine (11.3 mL, 3.0 eq.) was added thereto, followed by stirring thereof for 1 hour. Upon termination of the reaction, it was extracted three times with brine and DCM, dried over MgSO$_4$, and concentrated to obtain 6.8 g of the target compound in brown color (yield: 99%).

MS (ESI) m/z 252.1 [M+H]$^+$;
$^1$H NMR (300 MHz, CDCl$_3$) δ 5.24-5.17 (m, 1H), 4.31-4.25 (m, 2H), 4.13-4.08 (m, 2H), 3.07 (s, 3H), 1.45 (s, 9H).

Preparation Example 22: Synthesis of Intermediate 22 (tert-butyl 4-(methylsulfonyloxy)azepan-1-carboxylate)

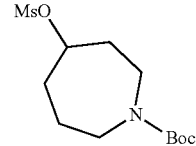

The same procedure as in Preparation Example 20 was carried out, except that tert-butyl-4-hydroxyazepan-1-carboxylate (2.0 g, 9.29 mmol) was used instead of tert-butyl-4-hydroxypiperidin-1-carboxylate, to obtain 2.7 g of the target compound (yield: 99%).

MS (ESI) m/z 294.0 [M+H]$^+$;
$^1$H NMR (300 MHz, CDCl$_3$) δ 4.91 (s, 1H), 3.45-3.38 (m, 1H), 3.02 (s, 3H), 2.08-2.04 (m, 5H), 1.73-1.64 (m, 1H), 1.47 (s, 9H).

Preparation Example 23: Synthesis of Intermediate 23 ((R)-tert-butyl 3-(methylsulfonyloxy)pyrrolidin-1-carboxylate)

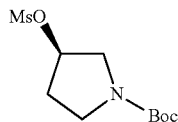

The same procedure as in Preparation Example 20 was carried out, except that (R)-tert-butyl-3-hydroxypyrrolidin-1-carboxylate (10.0 g, 53.41 mmol) was used instead of tert-butyl-4-hydroxypiperidin-1-carboxylate, to obtain 14.4 g of the target compound (yield: 99%).

MS (ESI) m/z 266.1 [M+H]$^+$;
$^1$H NMR (300 MHz, CDCl$_3$) δ 5.28-5.26 (m, 1H), 3.68-3.50 (m, 4H), 3.05 (s, 3H), 2.27-2.16 (m, 2H), 1.47 (s, 9H).

Preparation Example 24: Synthesis of Intermediate 24 ((S)-tert-butyl 3-(methylsulfonyloxy)pyrrolidin-1-carboxylate)

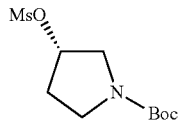

The same procedure as in Preparation Example 20 was carried out, except that (S)-tert-butyl-3-hydroxypyrrolidin-1-carboxylate (10.0 g, 53.41 mmol) was used instead of tert-butyl-4-hydroxypiperidin-1-carboxylate, to obtain 14.0 g of the target compound (yield: 98.8%).

MS (ESI) m/z 266.1 [M+H]$^+$

Preparation Example 25: Synthesis of Intermediate 25 (4-(5-chloro-4-nitro-1H-pyrazol-1-yl)piperidine hydrochloride)

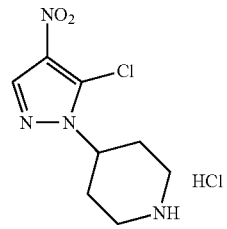 [SMILES: O=[N+]([O-])c1cnn(C2CCNCC2)c1Cl ; Cl]

Step 1: Synthesis of tert-butyl-4-(4-nitro-1H-pyrazol-1-yl)piperidin-1-carboxylate 4-Nitro-1H-pyrazole (4.71 g, 41.66 mmol) was dissolved in DMF (42 ml). NaH (2.7 g, 1.5 eq.) was added thereto, followed by stirring thereof at 0° C. for 30 minutes. Tert-butyl 4-(methylsulfonyloxy)piperidin-1-carboxylate (12.8 g, 1.1 eq. Intermediate 20) was added thereto, followed by elevation of the temperature to 150° C. and stirring thereof for 12 hours. Upon termination of the reaction, it was extracted three times with H$_2$O and DCM, dried over MgSO$_4$, and concentrated. It was subjected to column chromatography (MeOH:MC=1:40) to obtain 10.2 g of the target compound in yellow color (yield: 83%).

MS (ESI) m/z 297.2 [M+H]$^+$;
$^1$H NMR (300 MHz, CDCl$_3$) δ 8.17 (s, 1H), 8.09 (s, 1H), 4.34-4.26 (m, 3H), 2.20-2.16 (m, 3H), 1.98-1.89 (m, 2H), 1.49 (s, 9H).

Step 2: Synthesis of tert-butyl-4-(5-chloro-4-nitro-1H-pyrazol-1-yl)piperidin-1-carboxylate Tert-butyl-4-(4-nitro-1H-pyrazol-1-yl)piperidin-1-carboxylate (800 mg, 2.70 mmol) was dissolved in THF (9.0 ml). After the temperature was lowered to −78° C., LiHMDS (1 M in THF, 5.4 mL, 2.0 eq.) was added thereto, followed by stirring thereof for 30 minutes. Cl$_3$CCCl$_{13}$ (765 mg, 1.2 eq.) dissolved in THF (8.0 ml) was added thereto, followed by stirring thereof for 1 hour. Water was added thereto to terminate the reaction. Ethyl acetate was added thereto three times for extraction, it was dried over MgSO$_4$ and concentrated to obtain 500 mg of the target compound in brown color (yield: 56%).

MS (ESI) m/z 331.1 [M+H]$^+$;
$^1$H NMR (300 MHz, CDCl$_3$) δ 8.19 (s, 1H), 7.28 (s, 1H), 4.54-4046 (m, 1H), 4.32 (d, J=12.3 Hz, 2H), 2.91 (t, J=12.6 Hz, 2H), 2.20-2.07 (m, 2H), 1.94 (d, J=12.3 Hz, 2H), 1.49 (s, 9H).

Step 3: Synthesis of Intermediate 25

Tert-butyl-4-(5-chloro-4-nitro-1H-pyrazol-1-yl)piperidin-1-carboxylate (500 mg, 1.51 mmol) was dissolved in DCM (5 ml). HCl (4 M in dioxane, 1.13 ml, 3.0 eq.) was added thereto, followed by stirring thereof for 12 hours. Upon termination of the reaction, it was filtered to obtain 120 mg of the target compound in white color (yield: 34%).

MS (ESI) m/z 230.7 [M+H]$^+$;
$^1$H NMR (300 MHz, CDCl$_3$) δ 8.19 (s, 1H), 4.49-4.41 (m, 1H), 3.29 (d, J=12.9 Hz, 2H), 2.79 (t, J=10.8 Hz, 2H), 2.17-2.03 (m, 2H), 1.94 (d, J=11.7 Hz, 2H).

Preparation Example 26: Synthesis of Intermediate 26 (1-(4-(4-amino-5-chloro-1H-pyrazol-1-yl)piperidin-1-yl)ethanone)

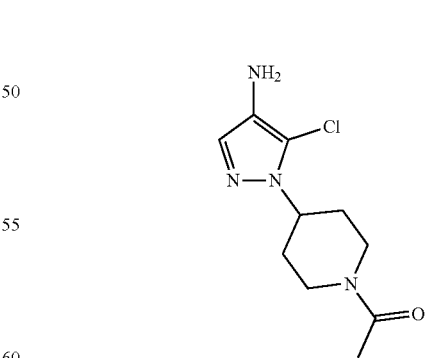

Step 1: Synthesis of 1-(4-(5-chloro-4-nitro-1H-pyrazol-1-yl)piperidin-1-yl)ethanone 4-(5-Chloro-4-nitro-1H-pyrazol-1-yl)piperidine hydrochloride (120 mg, 0.52 mmol, Intermediate 25) was added to THF (1.0 ml). K$_2$CO$_3$ (108 mg, 1.5 eq.) was added thereto, and acetyl chloride (0.04 ml, 1.1 eq.) was added thereto dropwise, followed by stirring thereof for 12 hours. Upon termination of the reaction, it was extracted with water and DCM and concentrated to obtain 110 mg of the target compound in white color (yield: 78%).

MS (ESI) m/z 273.1 [M+H]$^+$;

$^1$H NMR (300 MHz, CDCl$_3$) δ 8.19 (s, 1H), 4.82-4.78 (m, 1H), 4.63-4.53 (m, 1H), 4.07-4.01 (m, 1H), 3.44-3.27 (m, 2H), 2.83-2.75 (m, 1H), 2.16 (s, 3H), 2.06 (s, 3H).

Step 2: Synthesis of Intermediate 26

1-(4-(5-chloro-4-nitro-1H-pyrazol-1-yl)piperidin-1-yl)ethanone (110 mg, 0.403 mmol) was dissolved in EtOH (5 ml) and water (0.5 ml). NH$_4$Cl (64 mg, 3.0 eq.) and Fe (67 mg, 3.0 eq.) were added thereto, followed by stirring thereof at 90° C. for 12 hours. Upon termination of the reaction, Fe was removed, and it was concentrated. It was extracted with water and ethyl acetate, dried, and concentrated to obtain 90 mg of the target compound in red color (yield: 92%).

MS (ESI) m/z 243.1 [M+H]$^+$;

$^1$H NMR (300 MHz. CDCl$_3$) δ 7.23 (s, 1H), 4.75-4.70 (m, 1H), 4.37-4.32 (m, 1H), 4.00-3.95 (m, 1H), 3.43-2.73 (m, 4H), 2.13 (s, 3H), 2.05-1.98 (m, 2H).

Preparation Example 27: Synthesis of Intermediate 27 (5-chloro-1-(1-(methylsulfonyl)piperidin-4-yl)-1H-pyrazol-4-amine)

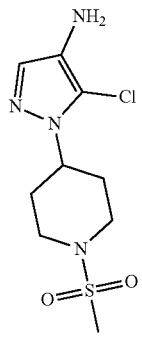

The same procedure as in Preparation Example 26 was carried out, except that methanesulfonyl chloride was used instead of acetyl chloride, to obtain 0.23 g of the target compound (yield: 73%).

MS (ESI) m/z 278.7, 280.4 [M+H]$^+$;

$^1$H NMR (300 MHz, DMSO-d$_6$) δ 7.21 (s, 1H) 4.13-4.05 (m, 1H), 3.90 (s, 2H), 3.65-3.59 (m, 2H), 2.92 (s, 3H), 2.90-2.83 (m, 2H), 2.02-1.88 (m, 2H), 1.88-1.82 (m, 2H).

Preparation Example 28: Synthesis of Intermediate 28 (4-(4-nitro-1H-pyrazol-1-yl)piperidine hydrochloride)

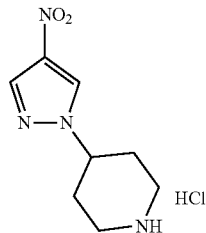 [SMILES: O=[N+]([O-])c1cnn(C2CCNCC2)c1 ; Cl]

Step 1: Synthesis of tert-butyl-4-(4-nitro-1H-pyrazol-1-yl)piperidin-1-carboxylate 4-Nitro-1H-pyrazole (4.71 g, 41.66 mmol) was dissolved in DMF (42 ml). NaH (2.7 g, 1.5 eq.) was added thereto, followed by stirring thereof at 0° C. for 30 minutes. Tert-butyl 4-(methylsulfonyloxy)piperidin-1-carboxylate (12.8 g, 1.1 eq. Intermediate 20) was added thereto, followed by elevation of the temperature to 150° C. and stirring thereof for 12 hours. Upon termination of the reaction, it was extracted three times with H$_2$O and DCM. It was dried over MgSO$_4$, concentrated, and subjected to column chromatography (MeOH:MC=1:40) to obtain 10.2 g of the target compound in yellow color (yield: 83%).

MS (ESI) m/z 297.2 [M+H]$^+$;

$^1$H NMR (300 MHz, CDCl$_3$) δ 8.17 (s, 1H), 8.09 (s, 1H), 4.34-4.26 (m, 3H), 2.20-2.16 (m, 3H), 1.98-1.89 (m, 2H), 1.49 (s, 9H).

Step 2: Synthesis of Intermediate 28

Tert-butyl-4-(4-nitro-1H-pyrazol-1-yl)piperidin-1-carboxylate (10.2 g, 34.42 mmol) was dissolved in DCM (68 ml). HCl (4 M in dioxane, 25.8 ml, 3.0 eq.) was added thereto, followed by stirring thereof for 12 hours. Upon termination of the reaction, it was filtered to obtain 6.0 g of the target compound in white color (yield: 75%).

MS (ESI) m/z 197.2 [M+H]$^+$;

$^1$H NMR (300 MHz. MeOD): δ 8.67 (s, 1H), 8.18 (s, 1H), 4.70-4.61 (m, 1H), 3.58 (d, J=13.2 Hz, 2H), 3.27-3.18 (m, 2H), 2.41-2.32 (m, 4H).

Preparation Example 29: Synthesis of Intermediate 29 (5-chloro-1-(1-(oxetan-3-yl)piperidin-4-yl)-1H-pyrazol-4-amine)

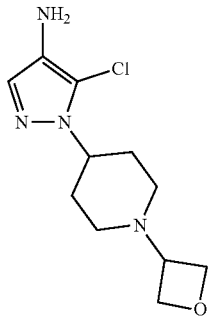 [SMILES: Nc1cnn(C2CCN(C3COC3)CC2)c1Cl]

Step 1: Synthesis of 4-(4-nitro-1H-pyrazol-1-yl)-1-(oxetan-3-yl)piperidine 4-(4-Nitro-1H-pyrazol-1-yl)piperidine hydrochloride (0.40 g, 1.74 mmol, Intermediate 28), dichloroethane (DCE, 15 ml), diisopropylethylamine (DIPEA, 0.44 g, 3.48 mmol), and oxetan-3-one (0.31 g, 4.35 mmol) were added and stirred for 15 minutes. NaBH(OAc)$_3$ (1.10 g, 5.22 mmol) and AcOH (0.12 g, 2.08 mmol) were added thereto, followed by stirring thereof for 2 hours. Upon termination of the reaction, it was immersed in NaHCO$_3$ and then extracted with DCM. After it was dried, the solution was evaporated under reduced pressure to obtain 0.42 g of the target compound (yield: 96%).

$^1$H NMR (300 MHz, CDCl$_3$) δ 8.19 (s, 1H), 8.10 (s, 1H), 4.72-4.62 (m, 4H), 4.19-4.17 (d, 1H, J=4.5 Hz), 3.60-3.52 (m, 1H), 2.92-2.90 (d, 2H, J=5.4 Hz), 2.231 (s, 2H), 2.11-2.05 (m, 4H).

Step 2: Synthesis of 4-(5-chloro-4-nitro-1H-pyrazol-1-yl)-1-(oxetan-3-yl)piperidine 4-(4-Nitro-1H-pyrazol-1-yl)-1-(oxetan-3-yl)piperidine (0.32 g, 1.26 mmol) was added to THF (15 ml), followed by stirring thereof at −78° C. LiHMDS (1 M in THF, 2.53 ml, 2.53 mmol) was added thereto, followed by stirring thereof for 30 minutes. Hexachloroethane (0.36 g, 1.52 mmol) dissolved in THF (3 ml) was added thereto dropwise, followed by stirring thereof for 30 minutes. Upon termination of the reaction, it was immersed in NH$_4$Cl and then extracted with ethyl acetate. It was dried over MgSO$_4$ and depressurized to obtain 0.26 g of the target compound (yield: 72%).

$^1$H NMR (300 MHz, CDCl$_3$) δ 8.20 (s, 1H), 4.72-4.62 (m, 4H), 4.42-4.31 (m, 1H), 3.61-3.52 (m, 1H), 2.95-2.91 (m, 2H), 2.38-2.25 (m, 2H), 2.09-1.96 (m, 4H).

Step 3: Synthesis of Intermediate 29

The same procedure as in step 2 of Preparation Example 26 was carried out, except that 4-(5-chloro-4-nitro-1H-pyrazol-1-yl)-1-(oxetan-3-yl)piperidine was used instead of 1-(4-(5-chloro-4-nitro-1H-pyrazol-1-yl)piperidin-1-yl)ethanone, to obtain 1.0 g of the target compound (yield: 86%).

MS (ESI) m/z 257.3, 259.1 [M+H]$^+$;
$^1$H NMR (300 MHz, CDCl$_3$) δ 7.24 (s, 1H), 4.70-4.62 (m, 4H), 4.19-4.09 (m, 1H), 3.59-3.51 (m, 1H), 2.90 (s, 4H), 2.28-2.16 (m, 2H), 2.05-1.92 (m, 4H).

Preparation Example 30: Synthesis of Intermediate 30 (1-(azetidin-3-yl)-4-nitro-1H-pyrazole hydrochloride)

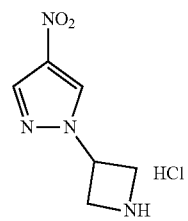

Step 1: Synthesis of tert-butyl-3-(4-nitro-1H-pyrazol-1-yl)azetidin-1-carboxylate 4-Nitro-1H-pyrazole (2.9 g, 25.77 mmol) was dissolved in DMF (30 ml). Cs$_2$CO$_3$ (17.6 g, 2.0 eq.) and tert-butyl-3-(methylsulfonyloxy)azetidin-1-carboxylate (6.8 g, 1.05 eq., Intermediate 21) were added thereto, followed by stirring thereof at 90° C. for 12 hours. Water was added thereto to terminate the reaction. It was extracted three times with ethyl acetate, dried over MgSO$_4$, and concentrated. It was subjected to column chromatography (MeOH:MC=1:40) to obtain 6.45 g of the target compound in yellow color (yield: 93%).

MS (ESI) m/z: 268.9 [M+H]$^+$;
$^1$H NMR (300 MHz, CDCl$_3$) δ 8.30 (s, 1H), 8.14 (s, 1H), 5.09-5.03 (m, 1H), 4.44-4.29 (m, 4H), 1.46 (s, 9H).

Step 2: Synthesis of Intermediate 30

Tert-butyl-3-(4-nitro-1H-pyrazol-1-yl)azetidin-1-carboxylate (6.45 g, 24.05 mmol) was dissolved in DCM (50 ml). HCl (4 M in dioxane, 20 ml, 3.0 eq.) was added thereto, followed by stirring thereof for 12 hours. Upon termination of the reaction, it was filtered to obtain 4.5 g of the target compound in white color (yield: 91%).

MS (ESI) m/z 429.9 [M+H]$^+$;
$^1$H NMR (300 MHz, MeOD) δ 8.68 (s, 1H), 8.32 (s, 1H), 5.54-5.50 (m, 1H), 4.62-4.55 (m, 4H).

Preparation Example 31: Synthesis of Intermediate 31 (5-chloro-1-(1-(oxetan-3-yl)azetidin-3-yl)-1H-pyrazol-4-amine)

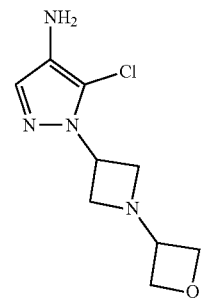 [SMILES: Nc1cnn(C2CN(C3COC3)C2)c1Cl]

Step 1: Synthesis of 4-nitro-1-(1-(oxetan-3-yl)azetidin-3-yl)-1H-pyrazole 1-(Azetidin-3-yl)-4-nitro-1H-pyrazole hydrochloride (1.0 g, 4.89 mmol, Intermediate 30) was added to DCE (20 ml). DIPEA (1.7 ml, 2.0 eq.) and oxetan-3-one (881 mg, 2.5 eq.) were added thereto, followed by stirring thereof at room temperature for 15 minutes. NaBH(OAc)$_3$ (3.1 g, 3.0 eq.) and AcOH (0.336 ml, 1.2 eq.) were added thereto, followed by stirring thereof at room temperature for 1.5 hours. Upon termination of the reaction, it was extracted with NaHCO$_3$ and DCM and concentrated. It was then subjected to column chromatography (MeOH:MC=1:40) to obtain 540 mg of the target compound in yellow color (yield: 49%).

MS (ESI) m/z 225.2 [M+H]$^+$;
$^1$H NMR (300 MHz, CDCl$_3$) δ 8.36 (s, 1H), 8.12 (s, 1H), 5.02-4.98 (m, 1H), 4.78-4.57 (m, 4H), 3.93-3.68 (m, 5H).

Step 2: Synthesis of 5-chloro-4-nitro-1-(1-(oxetan-3-yl)azetidin-3-yl)-1H-pyrazole The same procedure as in step 2 of Preparation Example 29 was carried out, except that 4-nitro-1-(1-(oxetan-3-yl)azetidin-3-yl)-1H-pyrazole was used instead of 4-(4-nitro-1H-pyrazol-1-yl)-1-(oxetan-3-yl)piperidine, to obtain 0.43 g of the target compound (yield: 69%).

MS (ESI) m/z 259.2 [M+H]$^+$;
$^1$H NMR (300 MHz, CDCl$_3$) δ 8.25 (s, 1H), 5.28-5.19 (m, 1H), 4.79-4.74 (m, 2H), 4.64-4.60 (m, 2H), 3.79-3.76 (m, 5H).

Step 3: Synthesis of Intermediate 31

The same procedure as in step 2 of Preparation Example 26 was carried out, except that 5-chloro-4-nitro-1-(1-(oxetan-3-yl)azetidin-3-yl)-1H-pyrazole was used instead of 1-(4-(5-chloro-4-nitro-1H-pyrazol-1-yl)piperidin-1-yl)ethanone, to obtain 0.1 g of the target compound (yield: 26%).

MS (ESI) m/z 229.2 [M+H]$^+$;
$^1$H NMR (300 MHz, CDCl$_3$) δ 7.30 (s, 1H), 5.08-5.03 (m, 1H), 4.77-4.73 (m, 2H), 4.64-4.60 (m, 2H), 3.96-3.69 (m, 5H).

Preparation Example 32: Synthesis of Intermediate 32 (3,5-dimethyl-4-nitro-1H-pyrazole)

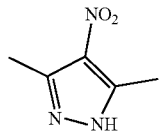

The same procedure as in Preparation Example 12 was carried out, except that 3,5-dimethyl-1H-pyrazole was used instead of 3-(trifluoromethyl)-1H-pyrazole, to obtain 7.0 g of the target compound (yield: 96%).

$^1$H NMR (300 MHz, CDCl$_3$) δ 11.01 (bs, 1H), 2.62 (s, 6H).

Preparation Example 33: Synthesis of Intermediate 33 (3-chloro-5-methyl-4-nitro-1H-pyrazole)

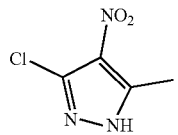

Step 1: Synthesis of 5-methyl-1H-pyrazol-3(2H)-one

Ethyl 3-oxobutanoate (28.59 g, 219.73 mmol) was added to EtOH (50 ml), followed by stirring thereof for 10 minutes in an ice bath. Hydrazine hydrate (10 g, 199.76 mmol) was added thereto, followed by refluxing thereof overnight. Upon termination of the reaction, it was evaporated under reduced pressure. Ethyl acetate was added thereto, followed by stirring and filtering thereof to obtain 14.68 g of the target compound in white color (yield: 75%).

$^1$H NMR (300 MHz, DMSO-d$_6$) δ 5.21 (s, 1H), 2.08 (s, 3H)

Step 2: Synthesis of 3-chloro-5-methyl-1H-pyrazole

A high-pressure reactor was charged with 5-methyl-1H-pyrazol-3(2H)-one (14 g, 101.93 mmol) and POCl$_3$ (42.20 g, 275.22 mmol), followed by refluxing thereof at 160° C. overnight. Upon termination of the reaction, it was evaporated and neutralized with NaHCO$_3$ and 5 N NaOH. It was extracted with DCM, dried over MgSO$_4$, and evaporated under reduced pressure. It was subjected to column chromatography (Hep:EA=2:1) to obtain 2.90 g of the target compound (yield: 17%).

MS (ESI) m/z 117.0 [M+H]$^+$;
$^1$H NMR (300 MHz, CDCl$_3$) δ 11.58 (bs, 1H), 6.01 (s, 1H), 2.37 (s, 3H).

Step 3: Synthesis of Intermediate 33

The same procedure as in Preparation Example 12 was carried out, except that 3-chloro-5-methyl-1H-pyrazole was used instead of 3-(trifluoromethyl)-1H-pyrazole, to obtain 3.68 g of the target compound (yield: 910%).
$^1$H NMR (300 MHz, CDCl$_3$) δ 2.72 (s, 3H).

Preparation Example 34: Synthesis of Intermediate 34 (3-chloro-1-isopropyl-1H-pyrazol-4-amine)

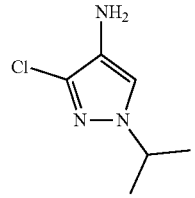

Step 1: Synthesis of 1-isopropyl-4-nitro-1H-pyrazole

4-Nitro-1H-pyrazole (0.30 g, 2.65 mmol) and DMF (30 ml) were added and stirred for 10 minutes in an ice bath. NaH (0.17 g, 3.97 mmol) was added thereto, followed by stirring thereof for 30 minutes. 2-Iodopropane (0.58 g, 3.44 mmol) was then added thereto, followed by refluxing thereof for 3 hours. Upon termination of the reaction, it was evaporated under reduced pressure and extracted with ethyl acetate. It was dried over MgSO$_4$ and evaporated under reduced pressure. It was subjected to column chromatography (Hep:EA=1:1) to obtain 0.26 g of the target compound in liquid phase (yield: 65%).

$^1$H NMR (300 MHz, CDCl$_3$) δ 8.17 (s, 1H), 8.09 (s, 1H), 4.58-4.49 (m, 1H), 1.56 (s, 6H).

Step 2: Synthesis of Intermediate 34

4-Nitro-3-(trifluoromethyl)-1H-pyrazole (0.26 g, 1.72 mmol), EtOH (20 ml) and HCl (1.43 ml, 17.20 mmol) were added and stirred under N$_2$. After Pd/Al (0.026 g) was added thereto, triethylsilane (1.20 g, 10.35 mmol) was added thereto dropwise, followed by reaction thereof overnight. Upon termination of the reaction, it was filtered with celite- 545. It was extracted with ethyl acetate and evaporated under reduced pressure to obtain 0.17 g of the target compound (yield: 50%).

MS (ESI) m/z 160.2 [M+H]+;
1H NMR (300 MHz, CDCl3) δ 7.59 (s, 1H), 4.67-4.58 (m, 1H), 1.38 (s, 3H), 1.36 (s, 3H).

Preparation Example 35: Synthesis of Intermediate 35 (3-chloro-1-cyclopropylmethyl-1H-pyrazol-4-amine)

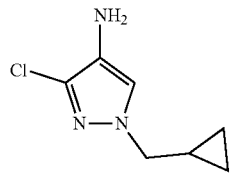 [SMILES: Nc1cn(CC2CC2)nc1Cl]

The same procedure as in Preparation Example 34 was carried out, except that (bromomethyl)cyclopropane was used instead of 2-iodopropane, to obtain 0.66 g of the target compound (yield: 88%).

MS (ESI) m/z 171.9, 174 [M+H]+;
1H NMR (300 MHz, CDCl3) δ 7.78 (s, 1H), 3.99 (s, 2H), 1.27-1.23 (m, 1H), 0.62-0.60 (m, 2H), 0.41 (s, 2H).

Preparation Example 36: Synthesis of Intermediate 36 (3-chloro-1-cyclopropyl-1H-pyrazol-4-amine)

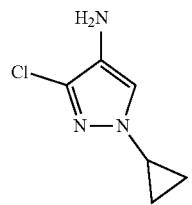

Step 1: Synthesis of 1-cyclopropyl-4-nitro-1H-pyrazole

A suction flask was charged with 4-nitro-1H-pyrazole (0.5 g, 4.42 mmol), cyclopropylboronic acid (0.75 g, 8.84 mmol), 2,2'-bipyridine (0.69 g, 4.42 mmol), and Na2CO3 (0.93 g, 8.84 mmol). Dichloroethane (22 ml) was added thereto, and nitrogen (N2) was bubbled for 10 minutes. Cu(OAc)2 (0.80 g, 4.42 mmol) was added thereto, and N2 was bubbled for 1 minute, followed by stirring thereof at 70° C. for 18 hours. The temperature was lowered to room temperature, and it was filtered with ethyl acetate and then concentrated. It was extracted with ethyl acetate and a 1 N aqueous hydrochloric acid solution, dried over MgSO4, filtered under reduced pressure, and concentrated to obtain 0.67 g of the target compound (yield: 45%).

1H NMR (300 MHz, CDCl3) δ 8.20 (s, 1H), 3.69 (p, J=1.8 Hz, 1H), 1.27-1.16 (m, 4H).

Step 2: Synthesis of Intermediate 36

The same procedure as in step 2 of Preparation Example 34 was carried out, except that 1-cyclopropyl-4-nitro-1H-pyrazole (0.3 g, 1.95 mmol) was used instead of 4-nitro-3-(trifluoromethyl)-1H-pyrazole, to obtain 0.14 g of the target compound (yield: 47%).

MS (ESI) m/z 158.0, 160.2 [M+H]+;
1H NMR (300 MHz, CDCl3) δ 7.16 (s, 1H), 4.37 (p, J=3.9 Hz, 1H), 2.89 (s, 2H), 1.18-1.14 (m, 2H), 1.07-1.04 (m, 2H).

Preparation Example 37: Synthesis of Intermediate 37 (3-chloro-1-(1-methylpiperidin-4-yl)-1H-pyrazol-4-amine)

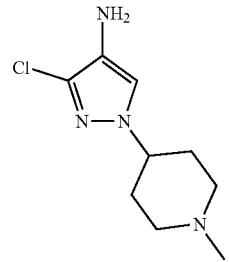

Step 1: Synthesis of 1-methyl-4-(4-nitro-1H-pyrazol-1-yl)piperidine 4-(4-Nitro-1H-pyrazol-1-yl)piperidine hydrochloride (0.4 g, 1.71 mmol) was dissolved in DMF (5 ml), and the temperature was lowered to 0° C. NaH (0.30 g, 6.87 mmol) was slowly added thereto, followed by stirring thereof for 30 minutes. Iodomethane (0.16 ml, 2.57 mmol) was added thereto dropwise, followed by stirring thereof at room temperature for 1 hour. Water was added thereto to terminate the reaction, and it was extracted with ethyl acetate. It was dried over MgSO4, filtered under reduced pressure, and concentrated. It was subjected to column chromatography to obtain 0.16 g of the target compound (yield: 45%).

MS (ESI) m/z 211.1 [M+H]+;
1H NMR (300 MHz, Acetone-d6) δ 8.64 (s, 1H), 8.12 (s, 1H), 4.26 (p J=7.2 Hz, 1H), 2.95-2.91 (m, 2H), 2.25 (s, 3H), 2.12-2.05 (m, 6H).

Step 2: Synthesis of Intermediate 37

The same procedure as in step 2 of Preparation Example 34 was carried out, except that 1-methyl-4-(4-nitro-1H-pyrazol-1-yl)piperidine (0.16 g, 0.76 mmol) was used instead of 4-nitro-3-(trifluoromethyl)-1H-pyrazole, to obtain 0.18 g of the target compound (yield: 95%).

MS (ESI) m/z 215.0, 217.0 [M+H]+

Preparation Example 38: Synthesis of Intermediate 38 (3-chloro-1-(1-ethylpiperidin-4-yl)-1H-pyrazol-4-amine)

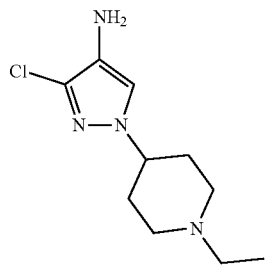

The same procedure as in Preparation Example 37 was carried out, except that iodoethane was used instead of iodomethane, to obtain 0.05 g of the target compound (yield: 21%).

MS (ESI) m/z 229.1 [M+H]$^+$

Preparation Example 39: Synthesis of Intermediate 39 (3-chloro-1-(tetrahydro-2H-pyran-4-yl)-1H-pyrazol-4-amine)

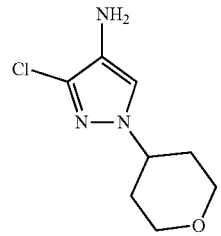 [SMILES: Nc1cn(C2CCOCC2)nc1Cl]

Step 1: Synthesis of 4-nitro-1-(tetrahydro-2H-pyran-4-yl)-1H-pyrazole

4-Nitro-1H-pyrazole (0.08 g, 0.76 mmol), DMF (10 ml), and Cs$_2$CO$_3$ (0.37 g, 1.14 mmol) were added and stirred for 30 minutes. Tetrahydro-2H-pyran-4-yl methanesulfonate (0.20 g, 1.314 mmol) was added thereto, followed by refluxing thereof for 2 hours. Upon termination of the reaction, it was evaporated under reduced pressure and extracted with ethyl acetate. It was dried over MgSO$_4$ and evaporated under reduced pressure. It was subjected to column chromatography (MC:MeOH=10:1) to obtain 0.085 g of the target compound (yield: 57%).

$^1$H NMR (300 MHz, CDCl$_3$) δ 8.19 (s, 1H), 8.11 (s, 1H), 4.44-4.34 (m, 1H), 4.18-4.13 (m, 2H), 3.61-3.52 (m, 2H), 2.20-2.01 (m, 4H).

Step 2: Synthesis of Intermediate 39

The same procedure as in step 2 of Preparation Example 34 was carried out, except that 4-nitro-1-(tetrahydro-2H-pyran-4-yl)-1H-pyrazole was used instead of 4-nitro-3-(trifluoromethyl)-1H-pyrazole, to obtain 0.04 g of the target compound (yield: 99%).

MS (ESI) m/z 202.0 [M+H]$^+$

Preparation Example 40: Synthesis of Intermediate 40 (3-chloro-1-(2,6-dimethyltetrahydro-2H-pyran-4-yl)-1H-pyrazol-4-amine)

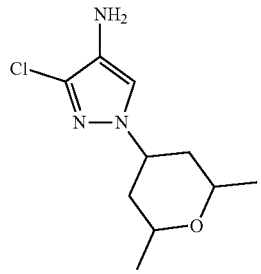

The same procedure as in Preparation Example 39 was carried out, except that 2,6-dimethyltetrahydro-2H-pyran-4-yl methanesulfonate was used instead of tetrahydro-2H-pyran-4-yl methanesulfonate, to obtain 0.09 g of the target compound (yield: 71%).

MS (ESI) m/z 230.1 [M+H]$^+$

Preparation Example 41: Synthesis of Intermediate 41 (3-chloro-1-(4-fluorophenyl)-1H-pyrazol-4-amine)

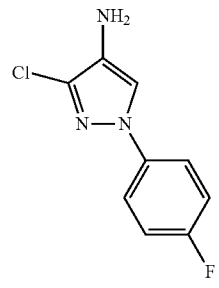 [SMILES: Nc1cn(-c2ccc(F)cc2)nc1Cl]

Step 1: Synthesis of 1-(4-fluorophenyl)-4-nitro-1H-pyrazole

4-Nitro-1H-pyrazole (1 g, 8.84 mmol), 4-fluorophenylboronic acid (2.47 g, 17.68 mmol), and Cu(OAc)$_2$ (2.41 g, 13.27 mmol) were added to DCM (40 ml). Pyridine (2.85 ml, 35.37 mmol) was added thereto, followed by stirring thereof at room temperature for 20 hours. Upon termination of the reaction, it was filtered and extracted with DCM and water. The organic layer was dried over MgSO$_4$, filtered, and concentrated under reduced pressure. It was subjected to column chromatography to obtain 0.82 g of the target compound (yield: 45%).

MS (ESI) m/z 208.0 [M+H]$^+$;

$^1$H NMR (300 MHz, CDCl$_3$) δ 9.62 (s, 1H), 8.55 (s, 1H), 8.01-7.98 (m, 2H), 7.45-7.41 (m, 2H).

Step 2: Synthesis of Intermediate 41

The same procedure as in step 2 of Preparation Example 34 was carried out, except that 1-(4-fluorophenyl)-4-nitro-1H-pyrazole (0.82 g, 3.95 mmol) was used instead of 4-nitro-3-(trifluoromethyl)-1H-pyrazole, to obtain 0.23 g of the target compound (yield: 27%).

MS (ESI) m/z 212.2, 214.1 [M+H]$^+$

Preparation Example 42: Synthesis of Intermediate 42 ((4-(4-amino-3-chloro-1H-pyrazol-1-yl)piperidin-1-yl)(cyclopropyl)methanone)

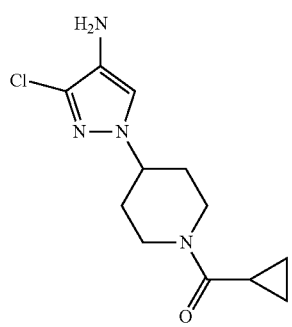 [SMILES: Nc1cn(C2CCN(C(=O)C3CC3)CC2)nc1Cl]

Step 1: Synthesis of cyclopropyl(4-(4-nitro-1H-pyrazol-1-yl)piperidin-1-yl)methanone 4-(4-Nitro-1H-pyrazol-1-yl)piperidine hydrochloride (0.25 g, 1.07 mmol, Intermediate 28) was dissolved in DCM. Triethylamine (0.37 ml, 2.68 mmol) was added thereto, and the temperature was lowered to 0° C. Cyclopropanecarbonyl chloride (0.11 ml, 1.28 mmol) was slowly added thereto dropwise, followed by stirring thereof at room temperature for 2 hours. Water was added thereto to terminate the reaction, and it was extracted with ethyl acetate. The organic layer was dried over $MgSO_4$, filtered under reduced pressure, and concentrated. It was subjected to column chromatography to obtain 0.28 g of the target compound (yield: 99%).

MS (ESI) m/z 265.1 $[M+H]^+$;

$^1$H NMR (300 MHz, Acetone-$d_6$) δ 8.69 (s, 1H), 8.14 (s, 1H), 4.65 (m, 3H), 3.37 (s, 1H), 2.78-2.75 (m, 2H), 2.27-2.25 (m, 2H), 2.02-1.97 (m, 2H), 0.84-0.82 (m, 2H), 0.81-0.78 (m, 2H).

Step 2: Synthesis of Intermediate 42

The same procedure as in step 2 of Preparation Example 34 was carried out, except that cyclopropyl(4-(4-nitro-1H-pyrazol-1-yl)piperidin-1-yl)methanone (0.28 g, 1.07 mmol) was used instead of 4-nitro-3-(trifluoromethyl)-1H-pyrazole, to obtain 0.10 g of the target compound (yield: 34%).

MS (ESI) m/z 269.1, 271.0 $[M+H]^+$;

$^1$H NMR (300 MHz, Acetone-$d_6$) δ 7.14 (s, 1H), 4.58-4.42 (m, 3H), 3.63 (s, 2H), 3.37 (m, 1H), 2.02-1.97 (m, 6H), 0.83-0.82 (m, 2H), 0.75-0.70 (m, 2H).

Preparation Example 43: Synthesis of Intermediate 43 (1-(4-(4-amino-3-chloro-1H-pyrazol-1-yl)piperidin-1-yl)-2-methylpropane-1-one)

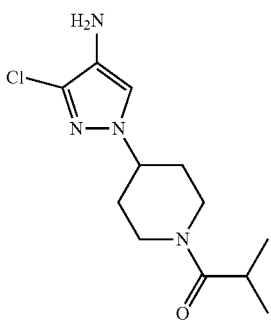 [SMILES: CC(C)C(=O)N1CCC(n2cc(N)c(Cl)n2)CC1]

The same procedure as in Preparation Example 42 was carried out, except that isobutyryl chloride was used instead of cyclopropanecarbonyl chloride, to obtain 0.35 g of the target compound (yield: 100%).

MS (ESI) m/z 271.1, 273.1 $[M+H]^+$;

$^1$H NMR (300 MHz, $CDCl_3$) δ 7.24 (s, 1H), 4.79-4.76 (d, 1H, J=11.4 Hz), 4.41-4.31 (m, 1H), 4.13-4.09 (d, 1H, J=12.6 Hz), 3.25-3.17 (t, 1H, J=24.6 Hz), 2.97-2.70 (m, 5H), 2.19-1.99 (m, 4H). 1.17-1.15 (d, 7H, J=6 Hz).

Preparation Example 44: Synthesis of Intermediate 44 (1-(4-(4-amino-3-chloro-1H-pyrazol-1-yl)piperidin-1-yl)-2,2-dimethylpropane-1-one)

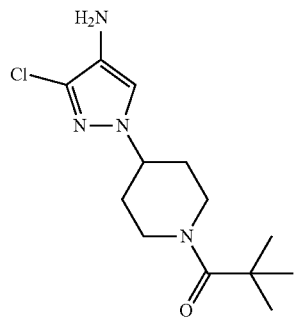 [SMILES: CC(C)(C)C(=O)N1CCC(n2cc(N)c(Cl)n2)CC1]

The same procedure as in Preparation Example 42 was carried out, except that pivaloyl chloride was used instead of cyclopropanecarbonyl chloride, to obtain 0.15 g of the target compound (yield: 22%).

MS (ESI) m/z 285.1, 287.0 $[M+H]^+$

Preparation Example 45: Synthesis of Intermediate 45 ((4-(4-amino-3-chloro-1H-pyrazol-1-yl)piperidin-1-yl)(morpholino)methanone)

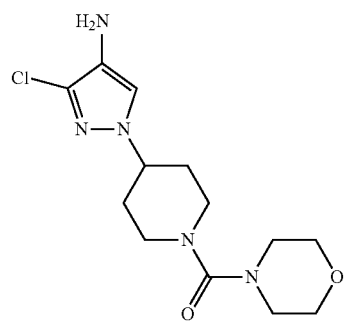 [SMILES: Nc1cn(C2CCN(C(=O)N3CCOCC3)CC2)nc1Cl]

The same procedure as in Preparation Example 42 was carried out, except that 4-morpholinecarbonyl chloride was used instead of cyclopropanecarbonyl chloride, to obtain 0.12 g of the target compound (yield: 48%).

MS (ESI) m/z 314.1, 316.0 $[M+H]^+$

Preparation Example 46: Synthesis of Intermediate 46 ((4-(4-amino-3-chloro-1H-pyrazol-1-yl)piperidin-1-yl)(4-methylpiperazin-1-yl)methanone)

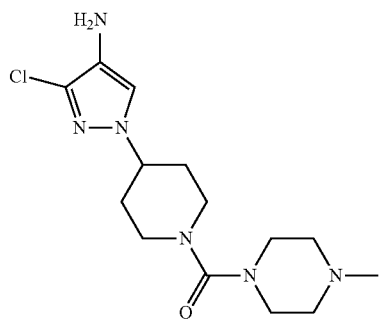 [SMILES: CN1CCN(C(=O)N2CCC(n3cc(N)c(Cl)n3)CC2)CC1]

The same procedure as in Preparation Example 42 was carried out, except that 4-methyl-1-piperazincarbonyl chloride hydrochloride was used instead of cyclopropanecarbonyl chloride, to obtain 0.35 g of the target compound (yield: 95%).

MS (ESI) m/z 327.1, 329.0 [M+H]+

Preparation Example 47: Synthesis of Intermediate 47 (3-chloro-1-(1-(methylsulfonyl)piperidin-4-yl)-1H-pyrazol-4-amine)

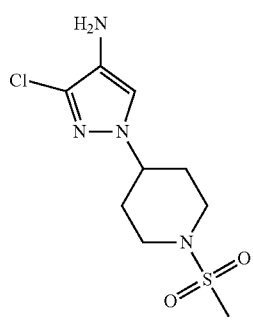 [SMILES: CS(=O)(=O)N1CCC(n2cc(N)c(Cl)n2)CC1]

The same procedure as in Preparation Example 42 was carried out, except that methanesulfonyl chloride was used instead of cyclopropanecarbonyl chloride, to obtain 5.4 g of the target compound (yield: 53%).

MS (ESI) m/z 278.9 [M+H]+;

$^1$H NMR (300 MHz, CDCl$_3$) δ 7.24 (s, 1H), 4.31-4.24 (m, 1H), 3.95-3.89 (m, 2H), 3.02-2.92 (m, 2H), 2.86 (s, 3H), 2.31-2.18 (m, 2H), 2.08-2.02 (m, 2H).

Preparation Example 48: Synthesis of Intermediate 48 (3-chloro-1-(1-(ethylsulfonyl)piperidin-4-yl)-1H-pyrazol-4-amine)

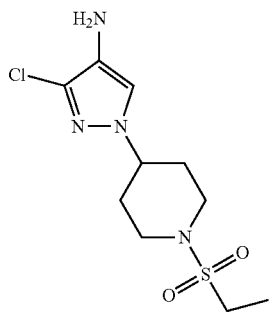 [SMILES: CCS(=O)(=O)N1CCC(n2cc(N)c(Cl)n2)CC1]

The same procedure as in Preparation Example 42 was carried out, except that ethanesulfonyl chloride was used instead of cyclopropanecarbonyl chloride, to obtain 0.58 g of the target compound (yield: 46%).

MS (ESI) m/z 293.2, 295.1 [M+H]+;

$^1$H NMR (300 MHz, CDCl$_3$) δ 7.11 (s, 1H), 4.29 (p, J=6.9 Hz, 1H), 4.00 (s, 2H), 3.72-3.66 (m, 2H), 3.08 (q, J=7.2 Hz, 2H), 1.94-1.86 (m, 4H), 1.22 (t, J=7.2 Hz, 3H).

Preparation Example 49: Synthesis of Intermediate 49 (3-chloro-1-(1-(cyclopropylsulfonyl)piperidin-4-yl)-1H-pyrazol-4-amine)

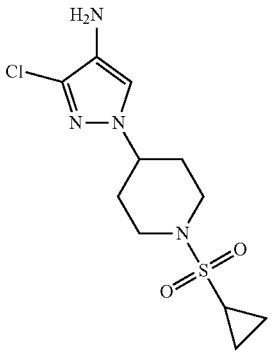 [SMILES: Nc1cn(C2CCN(S(=O)(=O)C3CC3)CC2)nc1Cl]

The same procedure as in Preparation Example 42 was carried out, except that cyclopropylsulfonyl chloride was used instead of cyclopropanecarbonyl chloride, to obtain 0.56 g of the target compound (yield: 46%).

MS (ESI) m/z 305.1, 307.1 [M+H]+;

$^1$H NMR (300 MHz, CDCl$_3$) δ 7.24 (s, 1H), 4.33-4.23 (m, 1H), 3.98-3.94 (m, 2H), 3.11-3.06 (m, 2H), 2.92 (s, 2H), 2.35-2.18 (m, 3H), 2.09-1.98 (m, 2H), 1.24-1.18 (m, 2H), 1.06-0.98 (m, 2H).

Preparation Example 50: Synthesis of Intermediate 50 (1-(4-(4-amino-3-chloro-1H-pyrazol-1-yl)piperidin-1-yl)2,2,2-trifluoroethanone)

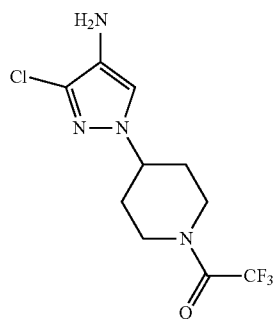 [SMILES: Nc1cn(C2CCN(C(=O)C(F)(F)F)CC2)nc1Cl]

Step 1: Synthesis of 2,2,2-trifluoro-1-(4-(4-nitro-1H-pyrazol-1-yl)piperidin-1-yl)ethanone 4-(5-Chloro-4-nitro-1H-pyrazol-1-yl)piperidine hydrochloride (500 mg, 2.15 mmol) was added to DCM (5 ml). TEA (0.66 ml, 2.2 eq.) and 2,2,2-trifluoroacetic anhydride (0.45 ml, 1.5 eq.) were added thereto, followed by stirring thereof at room temperature for 12 hours. Upon termination of the reaction, it was extracted with water and DCM and concentrated to obtain 680 mg of the target compound in white color (yield: 98%).

$^1$H NMR (300 MHz. CDCl$_3$) δ 8.21 (s, 1H), 8.10 (s, 1H), 4.70-4.64 (m, 1H), 4.52-4.43 (m, 1H), 4.21-4.17 (m, 1H), 3.42-3.32 (m, 1H), 3.11-3.03 (m, 1H), 2.34-2.30 (m, 2H), 2.16-2.07 (m, 2H).

Step 2: Synthesis of Intermediate 50

The same procedure as in step 2 of Preparation Example 34 was carried out, except that 2,2,2-trifluoro-1-(4-(4-nitro-1H-pyrazol-1-yl)piperidin-1-yl)ethanone (680 mg, 2.33 mmol) was used instead of 4-nitro-3-(trifluoromethyl)-1H-pyrazole, to obtain 200 mg of the target compound (yield: 29%).

MS (ESI) m/z: 297.1 [M+H]+;

$^1$H NMR (300 MHz. CDCl$_3$) δ 7.24 (s, 1H), 4.61-4.57 (m, 1H), 4.48-4.40 (m, 1H), 4.19-4.15 (m, 1H), 3.40-3.30 (m, 1H), 3.13-3.04 (m, 1H), 2.93 (s, 2H), 2.22-2.06 (m, 4H).

Preparation Example 51: Synthesis of Intermediate 51 (3-chloro-1-(1-(methylsulfonyl)azetidin-3-yl)-1H-pyrazol-4-amine)

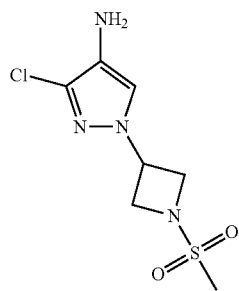

Step 1: Synthesis of 1-(1-(methylsulfonyl)azetidin-3-yl)-4-nitro-1H-pyrazole 1-(Azetidin-3-yl)-4-nitro-1H-pyrazole hydrochloride (500 mg, 2.44 mmol, Intermediate 30) was added to DCM (12 ml). TEA (1.4 ml, 3.0 eq.) and methanesulfonyl chloride (0.266 ml, 1.2 eq.) were added thereto dropwise, followed by stirring thereof at room temperature for 1 hour. Upon termination of the reaction, it was extracted with water and DCM and concentrated to obtain 500 mg of the target compound in yellow color (yield: 83%).

MS (ESI) m/z 247.1 [M+H]+;

$^1$H NMR (300 MHz, CDCl$_3$) δ 8.31 (s, 1H), 8.19 (s, 1H), 5.16-5.12 (m, 1H), 4.48-4.41 (m, 4H), 3.03 (s, 3H).

Step 2: Synthesis of Intermediate 51

The same procedure as in step 2 of Preparation Example 34 was carried out, except that 21-(1-(methylsulfonyl)azetidin-3-yl)-4-nitro-1H-pyrazole (500 mg, 2.03 mmol) was used instead of 4-nitro-3-(trifluoromethyl)-1H-pyrazole, to obtain 240 mg of the target compound (yield: 47%).

MS (ESI) m/z 250.1 [M+H]+;

$^1$H NMR (300 MHz, CDCl$_3$) δ 7.33 (s, 1H), 5.16-5.11 (m, 1H), 4.46-4.30 (m, 4H), 3.02 (s, 3H).

Preparation Example 52: Synthesis of Intermediate 52 ((3-(4-amino-3-chloro-1H-pyrazol-1-yl)azetidin-1-yl)(cyclopropyl)methanone)

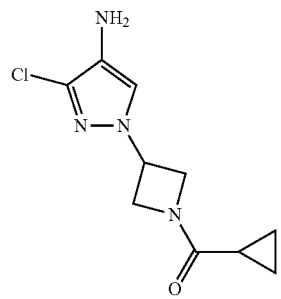 [SMILES: Nc1cn(C2CN(C(=O)C3CC3)C2)nc1Cl]

The same procedure as in Preparation Example 51 was carried out, except that cyclopropanecarbonyl chloride was used instead of methanesulfonyl chloride, to obtain 0.21 g of the target compound (yield: 41%).

MS (ESI) m/z: 241.2 [M+H]+;

$^1$H NMR (300 MHz, CDCl$_3$) δ 7.31 (s, 1H), 4.78-4.66 (m, 4H), 3.21-3.06 (m, 1H), 1.00-0.76 (m, 4H).

Preparation Example 53: Synthesis of Intermediate 53 (4-(4-nitro-1H-pyrazol-1-yl)azepane hydrochloride)

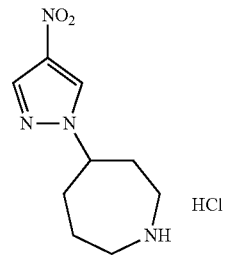 [SMILES: O=[N+]([O-])c1cnn(C2CCCNCC2)c1 ; Cl]

Step 1: Synthesis of tert-butyl-4-(4-nitro-1H-pyrazol-1-yl)azepan-1-carboxylate 4-Nitro-1H-pyrazole (0.946 g, 8.37 mmol) was dissolved in DMF (9 ml). NaH (0.548 g, 1.5 eq.) was added thereto, followed by stirring thereof at 0° C. for 30 minutes. Tert-butyl 4-(methylsulfonyloxy)azepan-1-carboxylate (2.7 g, 1.1 eq.) was added thereto, followed by elevation of the temperature to 150° C. and stirring thereof for 12 hours. Upon termination of the reaction, it was extracted three times with H$_2$O and DCM. It was dried over MgSO$_4$, concentrated, and then subjected to column chromatography (MeOH:MC=1:40) to obtain 2.2 g of the target compound in yellow color (yield: 85%).

MS (ESI) m/z 311.3 [M+H]+;

$^1$H NMR (300 MHz, CDCl$_3$) δ 8.15 (s, 1H), 8.07 (s, 1H), 4.33-4.26 (m, 1H), 3.78-3.33 (m, 4H), 2.29-1.72 (m, 6H), 1.49 (s, 9H).

Step 2: Synthesis of Intermediate 53

Tert-butyl-4-(4-nitro-1H-pyrazol-1-yl)azepan-1-carboxylate (2.2 g, 7.09 mmol) was dissolved in DCM (14 ml). HCl (4 M in dioxane, 5.32 ml, 3.0 eq.) was added thereto, followed by stirring thereof for 12 hours. Upon termination of the reaction, it was filtered to obtain 1.4 g of the target compound in white color (yield: 80%).

MS (ESI) m/z 211.2 [M+H]⁺;

¹H NMR (300 MHz, MeOD) δ 11.05 (s, 1H), 10.56 (s, 1H), 7.13-7.08 (m, 1H), 5.77-5.71 (m, 5H), 4.88-4.35 (m, 6H).

Preparation Example 54: Synthesis of Intermediate 54 ((R)-4-nitro-1-(pyrrolidin-3-yl)-1H-pyrazole hydrochloride)

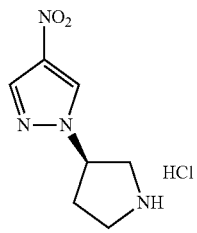 [SMILES: O=[N+]([O-])c1cnn([C@@H]2CCNC2)c1 ; Cl]

The same procedure as in Preparation Example 53 was carried out, except that (R)-tert-butyl-3-hydroxypyrrolidin-1-carboxylate was used instead of tert-butyl-4-(methylsulfonyloxy)azepan-1-carboxylate, to obtain 3.5 g of the target compound (yield: 90%).

MS (ESI) m/z 183.3 [M+H]⁺;

¹H NMR (300 MHz, MeOD) δ 8.73 (s, 1H), 8.21 (s, 1H), 5.39-5.32 (m, 1H), 3.80-3.53 (m, 4H), 2.69-2.47 (m, 2H).

Preparation Example 55: Synthesis of Intermediate 55 ((S)-4-nitro-1-(pyrrolidin-3-yl)-1H-pyrazole hydrochloride)

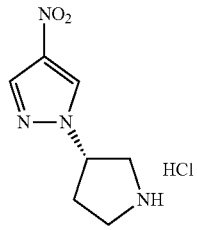 [SMILES: O=[N+]([O-])c1cnn([C@H]2CCNC2)c1 ; Cl]

The same procedure as in Preparation Example 53 was carried out, except that (S)-tert-butyl-3-hydroxypyrrolidin-1-carboxylate was used instead of tert-butyl-4-(methylsulfonyloxy)azepan-1-carboxylate, to obtain 3.0 g of the target compound (yield: 77.4%).

MS (ESI) m/z 183.3 [M+H]⁺

Preparation Example 56: Synthesis of Intermediate 56 (3-chloro-1-(1-(methylsulfonyl)azepan-4-yl)-1H-pyrazol-4-amine)

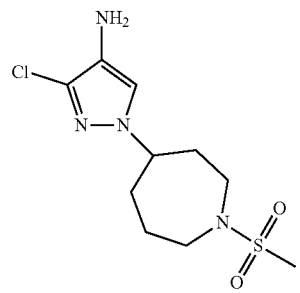 [SMILES: CS(=O)(=O)N1CCCC(n2cc(N)c(Cl)n2)CC1]

The same procedure as in Preparation Example 53 was carried out, except that 3-chloro-4-nitro-1H-pyrazole and tert-butyl-4-(methylsulfonyl)azepan-1-carboxylate were used instead of 4-nitro-1H-pyrazole and tert-butyl-4-(methylsulfonyloxy)azepan-1-carboxylate, to obtain 0.05 g of the target compound (yield: 11%).

MS (ESI) m/z 292.9 [M+H]⁺;

¹H NMR (300 MHz, CDCl₃) δ 7.28 (s, 1H), 4.48-4.44 (m, 1H), 3.70-3.50 (m, 3H), 3.26-3.18 (m, 1H), 2.86 (s, 3H), 3.31-1.99 (m, 6H).

Preparation Example 57: Synthesis of Intermediate 57 ((4-(4-amino-3-chloro-1H-pyrazol-1-yl)azepan-1-yl)(cyclopropyl)methanone)

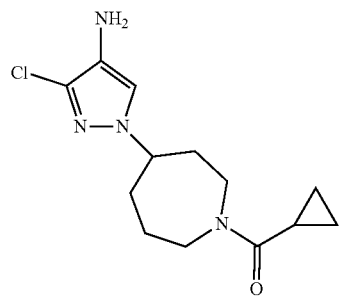 [SMILES: Nc1cn(C2CCCN(C(=O)C3CC3)CC2)nc1Cl]

The same procedure as in Preparation Example 53 was carried out, except that 3-chloro-4-nitro-1H-pyrazole and tert-butyl-4-(cyclopropanecarbonyl)azepan-1-carboxylate were used instead of 4-nitro-1H-pyrazole and tert-butyl-4-(methylsulfonyloxy)azepan-1-carboxylate, to obtain 0.22 g of the target compound (yield: 53%).

MS (ESI) m/z 282.9 [M+H]⁺;

¹H NMR (300 MHz, CDCl₃) δ 7.21 (s, 1H), 4.38-4.26 (m, 1H), 3.92-3.56 (m, 4H), 2.92 (s, 2H), 2.20-1.70 (m, 7H), 1.08-0.76 (m, 4H).

Preparation Example 58: Synthesis of Intermediate 58 ((R)-3-chloro-1-(1-(methylsulfonyl)pyrrolidin-3-yl)-1H-pyrazol-4-amine)

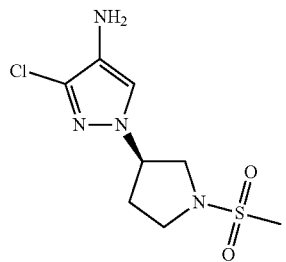 [SMILES: CS(=O)(=O)N1CC[C@@H](n2cc(N)c(Cl)n2)C1]

The same procedure as in Preparation Example 39 was carried out, except that (R)-1-(methylsulfonyl)pyrrolidin-3-yl methanesulfonate was used instead of tetrahydro-2H-pyran-4-yl methanesulfonate, to obtain 0.22 g of the target compound (yield: 36%).

MS (ESI) m/z 264.9 [M+H]$^+$;

$^1$H NMR (300 MHz, MeOD) δ 7.25 (s, 1H), 5.11-5.07 (m, 1H), 4.82-3.50 (m, 4H), 2.90 (s, 3H), 2.45-2.35 (m, 2H).

Preparation Example 59: Synthesis of Intermediate 59 ((S)-3-chloro-1-(1-(methylsulfonyl)pyrrolidin-3-yl)-1H-pyrazol-4-amine)

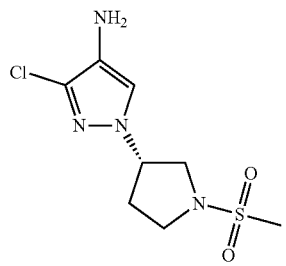 [SMILES: CS(=O)(=O)N1CC[C@H](n2cc(N)c(Cl)n2)C1]

The same procedure as in Preparation Example 39 was carried out, except that (S)-1-(methylsulfonyl)pyrrolidin-3-yl methanesulfonate was used instead of tetrahydro-2H-pyran-4-yl methanesulfonate, to obtain 0.2 g of the target compound (yield: 32.8%).

MS (ESI) m/z 264.9 [M+H]$^+$;

$^1$H NMR (300 MHz, CD$_3$OD) δ 7.25 (s, TH), 5.11-5.07 (m, 1H), 3.81-3.52 (m, 4H), 2.90 (s, 3H), 2.39-2.36 (m, 2H).

Preparation Example 60: Synthesis of Intermediate 60 ((R)-(3-(4-amino-3-chloro-1H-pyrazol-1-yl)pyrrolidin-1-yl)(cyclopentyl)methanone)

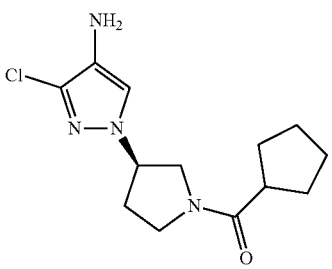 [SMILES: Nc1cn([C@@H]2CCN(C(=O)C3CCCC3)C2)nc1Cl]

The same procedure as in Preparation Example 39 was carried out, except that (R)-1-(cyclopentanecarbonyl)pyrrolidin-3-yl methanesulfonate was used instead of tetrahydro-2H-pyran-4-yl methanesulfonate, to obtain 0.28 g of the target compound (yield: 46%).

MS (ESI) m/z 283.0 [M+H]$^+$

Preparation Example 61: Synthesis of Intermediate 61 ((S)-(3-(4-amino-3-chloro-1H-pyrazol-1-yl)pyrrolidin-1-yl)(cyclopentyl)methanone)

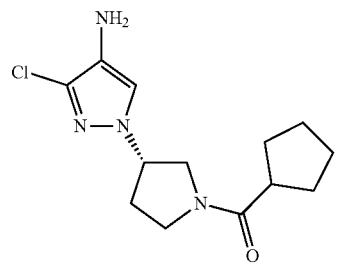 [SMILES: Nc1cn([C@H]2CCN(C(=O)C3CCCC3)C2)nc1Cl]

The same procedure as in Preparation Example 39 was carried out, except that (S)-1-(cyclopentanecarbonyl)pyrrolidin-3-yl methanesulfonate was used instead of tetrahydro-2H-pyran-4-yl methanesulfonate, to obtain 0.27 g of the target compound (yield: 44.2%).

MS (ESI) m/z 283.0 [M+H]$^+$;

$^1$H NMR (300 MHz, CD$_3$OD) δ 7.23 (s, 1H), 5.14-5.09 (m, 1H), 3.85-3.53 (m, 4H), 3.02-2.92 (m, 1H), 2.90 (s, 3H), 2.45-2.31 (m, 2H), 1.92-1.61 (m, 8H).

Preparation Example 62: Synthesis of Intermediate 62 ((4-(4-amino-3-chloro-5-methyl-1H-pyrazol-1-yl)piperidin-1-yl)(cyclopropyl)methanone)

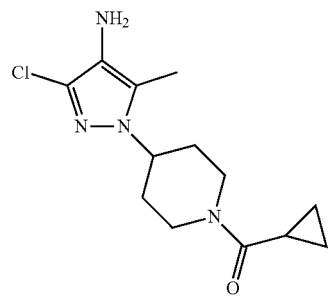 [SMILES: Cc1c(N)c(Cl)nn1C1CCN(C(=O)C2CC2)CC1]

Step 1: Synthesis of tert-butyl 4-(3-chloro-5-methyl-4-nitro-1H-pyrazol-1-yl)piperidin-1-carboxylate 3-Chloro-5-methyl-4-nitro-1H-pyrazole (1.84 g, 11.44 mmol, Intermediate 33) was dissolved in DMF (15 ml), which was stirred for 10 minutes in an ice bath. NaH (0.99 g, 22.89 mmol) was added thereto, followed by stirring thereof for 30 minutes. Tert-butyl 4-(methylsulfonyloxy)piperidin-1-carboxylate (4.79 g, 17.16 mmol) was added thereto, followed by stirring thereof at room temperature for 12 hours. Upon termination of the reaction, the solution was evaporated under reduced pressure, and it was extracted with ethyl acetate. It was dried over MgSO$_4$ and evaporated under reduced pressure. The filtrate was recrystallized with isopropyl ether to obtain 1.2 g of the target compound (yield: 30%).

Step 2: Synthesis of 4-(3-chloro-5-methyl-4-nitro-1H-pyrazol-1-yl)piperidine

Tert-butyl 4-(3-chloro-5-methyl-4-nitro-1H-pyrazol-1-yl)piperidin-1-carboxylate (0.90 g, 2.61 mmol) was added to DCM (dichloromethane, 30 ml). TFA (trifluoroacetic acid, 2.97 g, 26.10 mmol) was added thereto, followed by stirring thereof for 12 hours under reflux conditions. Upon termination of the reaction, the solution was evaporated under reduced pressure. Isopropyl ether was added to the residue, which was stirred to obtain 0.92 g of the target compound (yield: 98%).

Step 3: Synthesis of (4-(3-chloro-5-methyl-4-nitro-1H-pyrazol-1-yl)piperidin-1-yl)(cyclopropyl)methanone)

4-(3-Chloro-5-methyl-4-nitro-1H-pyrazol-1-yl)piperidine (0.50 g, 1.39 mmol) was added to DCM (30 ml). TEA (0.42 g, 4.18 mmol) and cyclopropanecarbonyl chloride (0.21 g, 2.09 mmol) were added thereto, followed by stirring thereof at room temperature for 1 hour. Upon termination of the reaction, water was added for extraction, which was dried over MgSO$_4$. The solution was evaporated under reduced pressure, and it was subjected to column chromatography (DCM:MeOH=10:1) to obtain 0.2 g of the target compound (yield: 46%).

Step 4: Synthesis of Intermediate 62

(4-(3-Chloro-5-methyl-4-nitro-1H-pyrazol-1-yl)piperidin-1-yl)(cyclopropyl)methanone) (0.2 g, 0.63 mmol) was added to ethanol and water (20 ml, 3:1 v/v). NH$_4$Cl (0.034 g, 0.63 mmol) and Fe (0.35 g, 6.39 mmol) were added thereto, followed by stirring at 70° C. for 1 hour. Upon termination of the reaction, it was filtered, and the solution was evaporated under reduced pressure. The filtrate was extracted again with ethyl acetate, dried over MgSO$_4$, and the solution was evaporated under reduced pressure to obtain 0.14 g of the target compound in liquid phase (yield: 90%).

MS (ESI) m/z 283.1, 285.0 [M+H]$^+$;
$^1$H NMR (300 MHz, CDCl$_3$) δ 4.73-4.60 (m, 1H, 4.48-4.41 (m, 1H), 4.17-4.08 (m, 1H), 3.24 (s, 1H), 2.68 (s, 2H), 2.23 (s, 3H), 1.93-1.84 (m, 2H), 1.81-1.73 (m, 1H), 1.00 (s, 2H), 0.80-0.76 (m, 2H).

Preparation Example 63: Synthesis of Intermediate 63 (3,5-dimethyl-1-(1-(methylsulfonyl)piperidin-4-yl)-1H-pyrazol-4-amine)

Step 1: Synthesis of tert-butyl-4-(3,5-dimethyl-4-nitro-1H-pyrazol-1-yl)piperidin-1-carboxylate 3,5-Dimethyl-4-nitro-1H-pyrazole (0.46 g, 3.25 mmol) was dissolved in DMF (4 ml). Tert-butyl 4-(methylsulfonyloxy)piperidine-1-carboxylate (1 g, 3.57 mmol) and Cs$_2$CO$_3$ (2.12 g, 6.52 mmol) were added thereto, followed by stirring thereof at 80° C. for 15 hours. Upon termination of the reaction, it was extracted with ethyl acetate and dried over MgSO$_4$. After the solution was evaporated under reduced pressure, ethyl acetate/heptane (1:3) was added to the residue to obtain 0.48 g of the target compound (yield: 46%).

MS (ESI) m/z 325.2 [M+H]$^+$;
$^1$H NMR (300 MHz, CDCl$_3$) δ 4.38-4.25 (m, 2H), 4.22-4.11 (m, 1H), 2.93-2.83 (m, 2H), 2.67 (s, 3H), 2.52 (s, 3H), 2.24-2.12 (m, 2H), 1.86-1.81 (m, 2H), 1.49 (s, 9H).

Step 2: Synthesis of 4-(3,5-dimethyl-4-nitro-1H-pyrazol-1-yl)piperidine hydrochloric acid The same procedure as in step 3 of Preparation Example 25 was carried out to obtain 0.39 g of the target compound (yield: 99%).

MS (ESI) m/z 225.1 [M+H]$^+$;
$^1$H NMR (300 MHz, CDCl$_3$) δ 8.83 (br s, 2H), 4.68-4.59 (m, 1H), 3.44-3.37 (m, 2H), 3.10-3.00 (m, 2H), 2.62 (s, 3H), 2.41 (s, 3H), 2.27-2.12 (m, 2H), 2.02-1.98 (m, 2H).

Step 3: Synthesis of 4-(3,5-dimethyl-4-nitro-1H-pyrazol-1-yl)-1-(methylsulfonyl)piperidine The same procedure as in step 1 of Preparation Example 42 was carried out, except that methanesulfonyl chloride was used instead of cyclopropanecarbonyl chloride, to obtain 0.39 g of the target compound (yield: 97%).

MS (ESI) m/z 302.35 [M+H]$^+$;
$^1$H NMR (300 MHz, CDCl$_3$) δ 4.21-4.14 (m, 1H), 4.01-3.96 (m, 2H), 3.00-2.91 (m, 2H), 2.88 (s, 3H), 2.66 (s, 3H), 2.51 (s, 3H), 2.39-2.30 (m, 4H), 2.02-1.97 (m, 2H).

Step 4: Synthesis of Intermediate 63

The same procedure as in step 3 of Preparation Example 17 was carried out, except that 4-(3,5-dimethyl-4-nitro-1H-pyrazol-1-yl)-1-(methylsulfonyl)piperidine was used instead of 5-chloro-1-methyl-4-nitro-1H-pyrazole, to obtain 0.21 g of the target compound (yield: 67%).

MS (ESI) m/z 273.1 [M+H]$^+$;
$^1$H NMR (300 MHz, CDCl$_3$) δ 4.05-3.89 (m, 3H), 2.96-2.91 (m, 2H), 2.86 (s, 3H), 2.30-2.24 (m, 2H), 2.17 (s, 6H), 1.99-1.94 (m, 2H).

Preparation Example 64: Synthesis of Intermediate 64 (3-chloro-1-(2-methoxyethyl)-1H-pyrazol-4-amine)

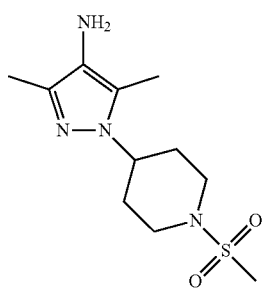 [SMILES: Cc1nn(C2CCN(S(C)(=O)=O)CC2)c(C)c1N]

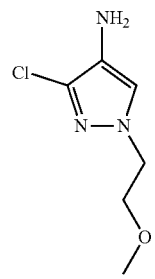

The same procedure as in Preparation Example 34 was carried out, except that 2-bromomethyl methyl ether was used instead of 2-iodopropane, to obtain 0.46 g of the target compound (yield: 59%).

MS (ESI) m/z 176.2, 178.1 [M+H]⁺;

¹H NMR (300 MHz, CDCl₃) δ 7.25 (s, 1H), 4.23 (t, J=5.7 Hz, 2H), 3.74 (t, J=5.7 Hz, 2H), 3.35 (s, 3H), 2.85 (s, 2H).

Preparation Example 65: Synthesis of Intermediate 65 (1-(4-(4-amino-3-chloro-1H-pyrazol-1-yl)piperidin-1-yl)ethanone)

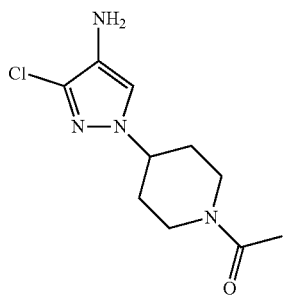 [SMILES: CC(=O)N1CCC(n2cc(N)c(Cl)n2)CC1]

The same procedure as in Preparation Example 37 was carried out, except that acetyl chloride was used instead of iodomethane, to obtain 0.22 g of the target compound (yield: 29%).

MS (ESI) m/z 243.2, 245.1 [M+H]⁺;

¹H NMR (300 MHz, CDCl₃) δ 7.24 (s, 1H), 4.77-4.74 (m, 1H), 4.39-4.30 (m, 1H), 4.01-3.97 (m, 1H), 3.28-3.19 (m, 1H), 2.92 (br s, 2H), 2.81-2.72 (m, 1H), 2.14 (s, 3H), 2.02-1.95 (m, 4H).

Example 1: Preparation of Compound 1

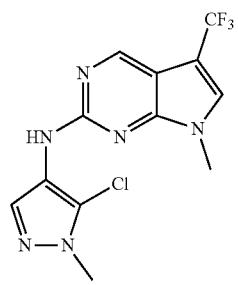 [SMILES: Cn1ncc(Nc2ncc3c(C(F)(F)F)cn(C)c3n2)c1Cl]

Intermediate 6 (2-chloro-7-methyl-5-(trifluoromethyl)-7H-pyrrolo[2,3-d pyrimidine, 45 mg, 0.29 mmol) and Intermediate 17 (5-chloro-1-methyl-1H-pyrazol-4-amine hydrochloride, 68.7 mg, 0.29 mmol) were dissolved in EtOH (1 ml). Added thereto was a drop of concentrated HCl. It was refluxed for 3 hours and cooled to room temperature to precipitate a solid. It was filtered with an ether to obtain 7.9 mg of the target compound (yield: 18%).

MS (ESI) m/z 331.0, 332.9 [M+H]⁺;

¹H NMR (300 MHz, CDCl₃) δ 8.98 (br s, 1H), 8.71 (s, 1H), 7.93 (s, 1H), 7.81 (s, 1H), 3.82 (s, 3H), 3.68 (s, 3H).

Example 2: Preparation of Compound 2

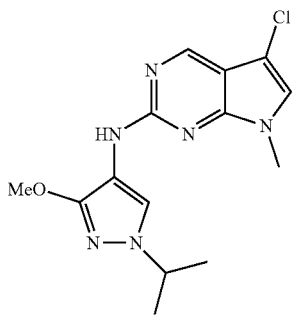 [SMILES: COc1nn(C(C)C)cc1Nc1ncc2c(Cl)cn(C)c2n1]

Method 1:

Intermediate 1 (2,5-dichloro-7-methyl-7H-pyrrolo[2,3-d] pyrimidine, 65 mg, 0.32 mmol) and Intermediate 11 (1-isopropyl-3-methoxy-1H-pyrazol-4-amine, 50 mg, 0.32 mmole) were added to n-BuOH (1 ml). Trifluoroacetic acid (TFA, 24.6 ul, 0.32 mmol) was added thereto, which was refluxed at 120° C. for 20 hours. The temperature was lowered to room temperature, and it was neutralized with NaHCO₃ and extracted with DCM. It was dried over MgSO₄, filtered under reduced pressure, and concentrated. It was subjected to column chromatography to obtain 46.1 mg of the target compound (yield: 44%).

MS (ESI) m/z 321.0, 323.1 [M+H]⁺;

¹H NMR (300 MHz, CDCl₃) δ 8.60 (s, 1H), 7.97 (s, 1H), 6.82 (s, 1H), 6.79 (s, 1H), 4.33 (p, J=6.6 Hz, 1H), 3.98 (s, 3H), 3.71 (s, 3H), 1.51 (s, 3H), 1.48 (s, 3H).

Method 2:

Pd(OAc)₂ (11.11 mg, 0.049 mmol) and Xantphos (34.3 mg, 0.059 mmol) were dissolved in dioxane (2 ml), followed by stirring thereof at room temperature for 30 minutes. Intermediate 11 (1-isopropyl-3-methoxy-1H-pyrazol-4-amine, 76.8 mg, 0.49 mmol) was added thereto, which was stirred for 5 minutes in an oil bath previously heated to 100° C. The temperature was then lowered to room temperature. Intermediate 1 (2,5-dichloro-7-methyl-7H-pyrrolo[2,3-d] pyrimidine, 100 mg, 0.49 mmol) and Cs₂CO₃ (0.45 g, 1.38 mmol) were added thereto, which was stirred at 100° C. for 5 hours. The temperature was then lowered to room temperature. H₂O was added thereto to terminate the reaction. It was filtered and then extracted with DCM and H₂O. It was dried over MgSO₄, filtered under reduced pressure, and concentrated. It was subjected to column chromatography to obtain 12.7 mg of the target compound (yield: 8%).

Examples 3 to 43: Preparation of Compounds 3 to 43

Compounds 3 to 43 were prepared by a procedure and a method similar to those of Examples 1 and 2, except that the type of each intermediate was changed as shown in Table 2 below. The physicochemical properties of each compound are shown in Table 3 below.

TABLE 2

| No. | Intermediate | |
| --- | --- | --- |
| Example 1 | Intermediate 6 | Intermediate 17 |
| Example 2 | Intermediate 1 | Intermediate 11 |
| Example 3 | Intermediate 1 | Intermediate 34 |

TABLE 2-continued

| No. | Intermediate | |
|---|---|---|
| Example 4 | Intermediate 1 | Intermediate 13 |
| Example 5 | Intermediate 1 | Intermediate 17 |
| Example 6 | Intermediate 2 | Intermediate 17 |
| Example 7 | Intermediate 4 | Intermediate 34 |
| Example 8 | Intermediate 2 | Intermediate 34 |
| Example 9 | Intermediate 1 | Intermediate 14 |
| Example 10 | Intermediate 1 | Intermediate 15 |
| Example 11 | Intermediate 1 | Intermediate 16 |
| Example 12 | Intermediate 2 | Intermediate 64 |
| Example 13 | Intermediate 2 | Intermediate 35 |
| Example 14 | Intermediate 2 | Intermediate 36 |
| Example 15 | Intermediate 5 | Intermediate 36 |
| Example 16 | Intermediate 2 | Intermediate 18 |
| Example 17 | Intermediate 2 | Intermediate 37 |
| Example 18 | Intermediate 2 | Intermediate 39 |
| Example 19 | Intermediate 2 | Intermediate 40 |
| Example 20 | Intermediate 2 | Intermediate 38 |
| Example 21 | Intermediate 2 | Intermediate 41 |
| Example 22 | Intermediate 2 | Intermediate 19 |
| Example 23 | Intermediate 1 | Intermediate 26 |
| Example 24 | Intermediate 2 | Intermediate 42 |
| Example 25 | Intermediate 2 | Intermediate 47 |
| Example 26 | Intermediate 2 | Intermediate 43 |
| Example 27 | Intermediate 1 | Intermediate 29 |
| Example 28 | Intermediate 2 | Intermediate 29 |
| Example 29 | Intermediate 5 | Intermediate 29 |
| Example 30 | Intermediate 5 | Intermediate 47 |
| Example 31 | Intermediate 2 | Intermediate 45 |
| Example 32 | Intermediate 2 | Intermediate 46 |
| Example 33 | Intermediate 2 | Intermediate 44 |
| Example 34 | Intermediate 2 | Intermediate 63 |
| Example 35 | Intermediate 2 | Intermediate 49 |
| Example 36 | Intermediate 2 | Intermediate 58 |
| Example 37 | Intermediate 2 | Intermediate 59 |
| Example 38 | Intermediate 2 | Intermediate 60 |
| Example 39 | Intermediate 2 | Intermediate 61 |
| Example 40 | Intermediate 2 | Intermediate 51 |
| Example 41 | Intermediate 2 | Intermediate 52 |
| Example 42 | Intermediate 2 | Intermediate 56 |
| Example 43 | Intermediate 2 | Intermediate 57 |

TABLE 3

| Compound No. | Structure | Analysis results (MS, $^1$H NMR) |
|---|---|---|
| 3 | 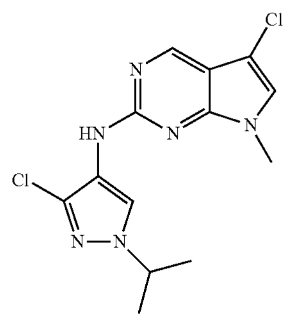 [SMILES: CC(C)n1cc(Nc2ncc3c(Cl)cn(C)c3n2)c(Cl)n1] | MS (ESI) m/z 325.0, 327.0 [M + H]$^+$; $^1$H NMR (300 MHz, CDCl$_3$) δ 8.61 (s, 1H), 8.31 (s, 1H), 6.85 (s, 1H), 4.71-4.62 (m, 1H), 3.72 (s, 3H), 1.56 (s, 3H), 1.54 (s, 3H). |
| 4 | 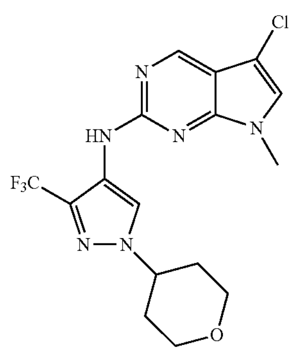 [SMILES: Cn1cc(Cl)c2cnc(Nc3cn(C4CCOCC4)nc3C(F)(F)F)nc21] | MS (ESI) m/z 401.0, 403.1 [M + H]$^+$; $^1$H NMR (300 MHz, CDCl$_3$) δ 8.62 (s, 1H), 8.42 (s, 1H), 7.04 (s, 1H), 6.85 (s, 1H), 4.45-4.34 (m, 1H), 4.14-4.10 (m, 2H), 3.72 (s, 3H), 3.58-3.50 (m, 2H), 2.16-2.13 (m, 4H). |
| 5 | 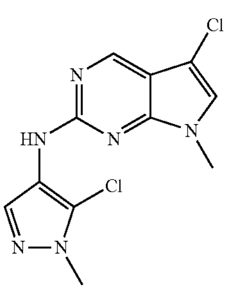 [SMILES: Cn1ncc(Nc2ncc3c(Cl)cn(C)c3n2)c1Cl] | MS (ESI) m/z 297.0, 299.0 [M + H]$^+$; $^1$H NMR (300 MHz, CDCl$_3$) δ 8.61 (s, 1H), 8.23 (s, 1H), 6.84 (s, 1H), 6.64 (s, 1H), 3.87 (s, 3H), 3.72 (s, 3H). |

TABLE 3-continued

| Compound No. | Structure | Analysis results (MS, ¹H NMR) |
|---|---|---|
| 6 | 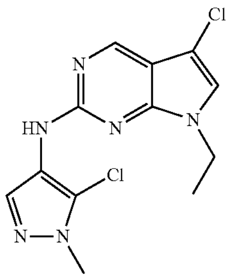 [SMILES: CCn1cc(Cl)c2cnc(Nc3cnn(C)c3Cl)nc21] | MS (ESI) m/z 311.0 [M + H]$^+$; $^1$H NMR (300 MHz, CDCl$_3$) δ 8.61 (s, 1H), 8.22 (s, 1H), 6.88 (s, 1H), 6.63 (s, 1H), 4.20-4.15 (m, 2H), 3.87 (s, 3H), 1.45 (t, J = 7.2 Hz, 3H). |
| 7 | 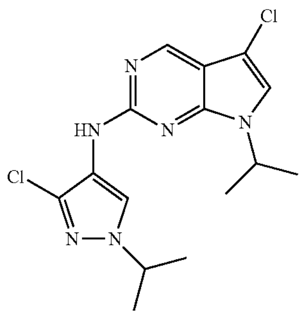 [SMILES: CC(C)n1cc(Nc2ncc3c(Cl)cn(C(C)C)c3n2)c(Cl)n1] | MS (ESI) m/z 350.0, 355.1 [M + H]$^+$; $^1$H NMR (300 MHz, CDCl$_3$) δ 10.17 (s, 1H), 8.39 (s, 1H), 8.06 (s, 1H), 7.20 (s, 1H), 4.93 (p, J = 6.9 Hz, 1H), 4.70 (p, J = 6.9 Hz, 1H), 1.54 (s, 3H), 1.53 (s, 3H), 1.52 (s, 3H), 1.51 (s, 3H). |
| 8 | 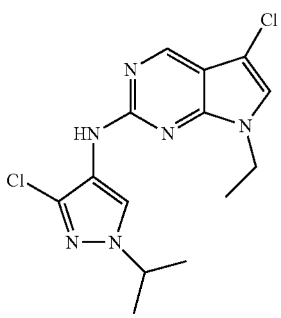 [SMILES: CCn1cc(Cl)c2cnc(Nc3cn(C(C)C)nc3Cl)nc21] | MS (ESI) m/z 339.1, 341.0 [M + H]$^+$; $^1$H NMR (300 MHz, CDCl$_3$) δ 8.62 (s, 1H), 8.33 (s, 1H), 6.88 (s, 1H), 6.65 (s, 1H), 4.69-4.64 (m, 1H), 4.21-4.13 (m, 2H), 1.54 (s, 3H), 1.52 (s, 1H), 1.48-1.43 (t, 3H, J = 14.7 Hz). |
| 9 | 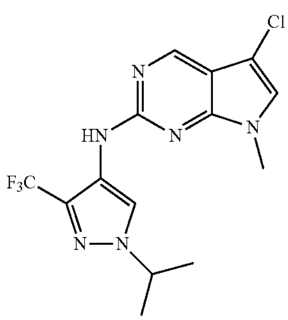 [SMILES: CC(C)n1cc(Nc2ncc3c(Cl)cn(C)c3n2)c(C(F)(F)F)n1] | MS (ESI) m/z 359.1, 361.0 [M + H]$^+$; $^1$H NMR (300 MHz, CDCl$_3$) δ 8.66 (s, 1H), 8.41 (s, 1H), 7.06 (s, 1H), 6.87 (s, 1H), 4.61-4.52 (m, 1H), 3.75 (s, 3H), 1.60 (s, 3H), 1.58 (s, 3H) |
| 10 | 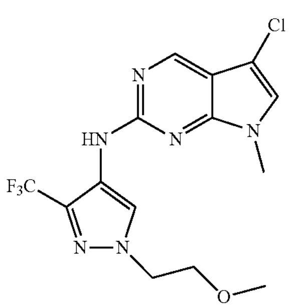 [SMILES: COCCn1cc(Nc2ncc3c(Cl)cn(C)c3n2)c(C(F)(F)F)n1] | MS (ESI) m/z 375.0, 377.0 [M + H]$^+$; $^1$H NMR (300 MHz, CDCl$_3$) δ 8.65 (s, 1H), 8.48 (s, 1H), 7.00 (s, 1H), 6.87 (s, 1H), 4.37-4.34 (t, 2H, J = 10.5 Hz), 3.83-3.80 (t, 2H, J = 10.5 Hz), 3.76 (s, 3H), 3.39 (s, 3H). |

TABLE 3-continued

| Compound No. | Structure | Analysis results (MS, ¹H NMR) |
|---|---|---|
| 11 | (structure) | MS (ESI) m/z 373.1, 375.0 [M + H]⁺;<br>¹H NMR (300 MHz, CDCl₃) δ 8.66 (s, 1H), 8.36 (s, 1H), 7.05 (s, 1H), 6.88 (s, 1H), 4.21-4.16 (t, 2H, J = 14.1 Hz), 3.75 (s, 3H), 1.98-1.88 (m, 2H), 1.45-1.38 (m, 2H), 1.01-0.97 (t, 3H, J = 14.7 Hz). |
| 12 | (structure) | MS (ESI) m/z 355.0, 357.1 [M + H]⁺;<br>¹H NMR (300 MHz, CDCl₃) δ 10.11 (s, 1H), 8.39 (s, 1H), 8.01 (s, 1H), 7.12 (s, 1H), 4.37-4.35 (m, 2H), 4.18 (q, J = 7.2 Hz, 2H), 3.80-3.78 (m, 2H), 3.31 (s, 3H), 1.45 (t, J = 7.2 Hz, 3H). |
| 13 | (structure) | MS (ESI) m/z 351.0, 353.1 [M + H]⁺;<br>¹H NMR (300 MHz, CDCl₃) δ 8.62 (s, 1H), 8.29 (s, 1H), 6.89 (s, 1H), 6.65 (s, 1H), 4.21-4.14 (m, 2H), 4.04-4.02 (d, 2H, J = 7.2 Hz), 1.48-1.43 (t, 3H, J = 6.6 Hz), 1.27 (s, 1H), 0.65-0.58 (m, 2H), 0.47-0.42 (m, 2H). |
| 14 | (structure) | MS (ESI) m/z 336.9, 339.1 [M + H]⁺;<br>¹H NMR (300 MHz, CDCl₃) δ 8.61 (s, 1H), 8.23 (s, 1H), 6.89 (s, 1H), 6.63 (s, 1H), 4.16 (q, J = 7.2 Hz, 2H), 3.51-3.44 (m, 1H), 1.45 (t, J = 7.2 Hz, 3H), 1.27-1.22 (m, 2H), 1.13-1.09 (m, 2H). |
| 15 | (structure) | MS (ESI) m/z 348.9, 351.0 [M + H]⁺;<br>¹H NMR (300 MHz, CDCl₃) δ 8.58 (s, 1H), 8.35 (s, 1H), 6.86 (s, 1H), 6.68 (s, 1H), 3.51-3.45 (m, 1H), 3.37-3.31 (m, 1H), 1.27-1.23 (m, 4H), 1.14-1.06 (m, 4H). |

TABLE 3-continued

| Compound No. | Structure | Analysis results (MS, $^1$H NMR) |
|---|---|---|
| 16 | *[structure: 5-chloro-N-(5-chloro-1-(oxetan-3-yl)-1H-pyrazol-4-yl)-7-ethyl-7H-pyrrolo[2,3-d]pyrimidin-2-amine]* | MS (ESI) m/z 353.0, 355.0 [M + H]$^+$ |
| 17 | *[structure: 5-chloro-N-(3-chloro-1-(1-methylpiperidin-4-yl)-1H-pyrazol-4-yl)-7-ethyl-7H-pyrrolo[2,3-d]pyrimidin-2-amine]* | MS (ESI) m/z 394.1, 396.3 [M + H]$^+$; $^1$H NMR (300 MHz, CDCl$_3$) δ 8.60 (s, 1H), 8.32 (s, 1H), 6.88 (s, 1H), 6.73 (s, 1H), 4.21-4.13 (m, 3H), 3.03 (d, J = 11.1 Hz, 2H), 2.36 (s, 3H), 2.32-2.13 (m, 6H), 2.01-1.97 (m, 2H), 1.45 (t, J = 7.2 Hz, 3H). |
| 18 | *[structure: 5-chloro-N-(3-chloro-1-(tetrahydro-2H-pyran-4-yl)-1H-pyrazol-4-yl)-7-ethyl-7H-pyrrolo[2,3-d]pyrimidin-2-amine]* | MS (ESI) m/z 381.0, 383.0 [M + H]$^+$; $^1$H NMR (300 MHz, CDCl$_3$) δ 8.62 (s, 1H), 8.35 (s, 1H), 6.89 (s, 1H), 6.71 (s, 1H), 4.50-4.42 (m, 1H), 4.19-4.14 (m, 2H), 3.67-3.55 (m, 2H), 2.53-2.44 (m, 2H), 2.38-2.24 (m, 2H), 2.08-1.92 (m, 4H), 1.48-1.43 (t, 3H, J = 14.7 Hz). |
| 19 | *[structure: 5-chloro-N-(3-chloro-1-(2,6-dimethyltetrahydro-2H-pyran-4-yl)-1H-pyrazol-4-yl)-7-ethyl-7H-pyrrolo[2,3-d]pyrimidin-2-amine]* | MS (ESI) m/z 409.1, 411.1 [M + H]$^+$; $^1$H NMR (300 MHz, CDCl$_3$) δ 8.62 (s, 1H), 8.32 (s, 1H), 6.90 (s, 1H), 6.68 (s, 1H), 4.76 (s, 1H), 4.28-4.15 (m, 4H), 2.08-2.03 (m, 2H), 1.79-1.69 (m, 2H), 1.49-1.44 (t, 3H, J = 14.4), 1.26 (s, 3H), 1.21 (s, 3H). |

TABLE 3-continued

| Compound No. | Structure | Analysis results (MS, $^1$H NMR) |
|---|---|---|
| 20 | 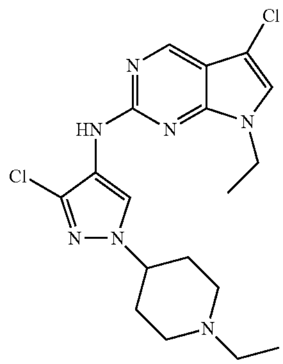 [SMILES: CCN1CCC(n2cc(Nc3ncc4c(Cl)cn(CC)c4n3)c(Cl)n2)CC1] | MS (ESI) m/z 408.1 [M + H]$^+$ |
| 21 | 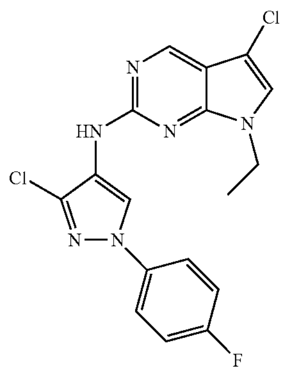 [SMILES: CCn1cc(Cl)c2cnc(Nc3cn(-c4ccc(F)cc4)nc3Cl)nc21] | MS (ESI) m/z 391.0, 393.0 [M + H]$^+$ |
| 22 | 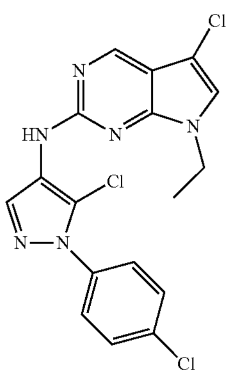 [SMILES: CCn1cc(Cl)c2cnc(Nc3cnn(-c4ccc(Cl)cc4)c3Cl)nc21] | MS (ESI) m/z 407.0, 409.0 [M + H]$^+$; $^1$H NMR (300 MHz, CDCl$_3$) δ 8.65 (s, 1H), 8.56 (s, 1H), 7.61-7.58 (m, 2H), 7.50-7.47 (m, 2H), 6.93 (s, 1H), 6.76 (s, 1H), 4.21 (q, J = 7.2 Hz, 2H), 1.48 (t, J = 7.2 Hz, 3H). |
| 23 | 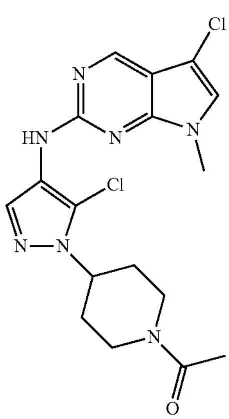 [SMILES: CC(=O)N1CCC(n2ncc(Nc3ncc4c(Cl)cn(C)c4n3)c2Cl)CC1] | MS (ESI) m/z 408.0 [M + H]$^+$; $^1$H NMR (300 MHz, CDCl$_3$) δ 8.61 (s, 1H), 8.31 (s, 1H), 6.85 (s, 1H), 6.76 (s, 1H), 4.77 (d, J = 13.8 Hz, 1H), 4.50-4.45 (m, 1H), 4.01 (d, J = 12.3 Hz, 2H), 3.72 (s, 3H) 3.28 (t, J = 12.3 Hz, 3H), 2.80 (t, J = 13.5 Hz, 1H), 2.16 (s, 3H), 2.08-2.03 (m, 3H). |

TABLE 3-continued
| Compound No. | Structure | Analysis results (MS, ¹H NMR) |
|---|---|---|
| 24 | 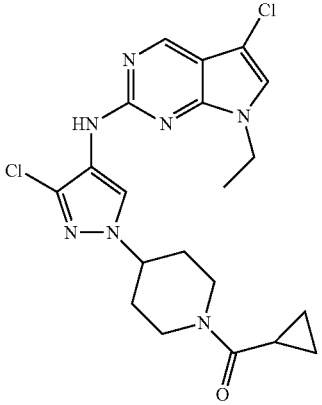 [SMILES: CCn1cc(Cl)c2cnc(Nc3cn(C4CCN(C(=O)C5CC5)CC4)nc3Cl)nc21] | MS (ESI) m/z 448.1, 450.1 [M + H]$^+$;<br>¹H NMR (300 MHz, CDCl$_3$) δ 8.62 (s, 1H), 8.33 (s, 1H), 6.89 (s, 1H), 6.70 (s, 1H), 4.82-4.80 (m, 1H), 4.56-4.45 (m, 2H), 4.17 (q, J = 7.2 Hz, 2H), 2.23-2.07 (m, 6H), 1.83-1.76 (m, 1H), 1.45 (t, J = 7.2 Hz, 3H), 1.03-1.02 (m, 2H), 1.01-0.82 (m, 2H). |
| 25 | 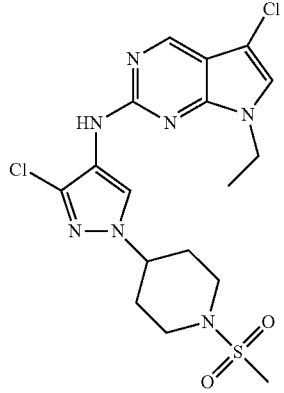 [SMILES: CCn1cc(Cl)c2cnc(Nc3cn(C4CCN(S(C)(=O)=O)CC4)nc3Cl)nc21] | MS (ESI) m/z 458.0, 460.0 [M + H]$^+$;<br>¹H NMR (300 MHz, CDCl$_3$) δ 8.62 (s, 1H), 8.33 (s, 1H), 6.90 (s, 1H), 6.69 (s, 1H), 4.38 (p, J = 3.9 Hz, 1H), 4.17 (q, J = 7.2 Hz, 2H), 3.99-3.95 (m, 2H), 3.05-2.98 (m, 2H), 2.88 (s, 3H), 2.34-2.27 (m, 2H), 2.14-2.09 (m, 2H), 1.46 (t, J = 7.2 Hz, 3H). |
| 26 | 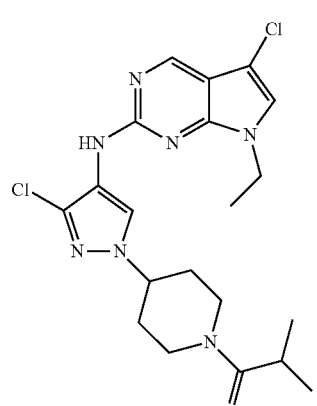 | MS (ESI) m/z 450.1, 452.2 [M + H]$^+$;<br>¹H NMR (300 MHz, CDCl$_3$) δ 8.62 (s, 1H), 8.33 (s, 1H), 6.89 (s, 1H), 6.68 (s, 1H), 4.83-4.80 (m, 1H), 4.52-4.43 (m, 1H), 4.20-4.13 (m, 2H), 3.28-3.24 (m, 1H), 2.91-2.74 (m, 3H), 2.06 (s, 4H), 1.48-1.43 (t, 3H, J = 14.7 Hz), 1.18-1.17 (m, 6H). |

TABLE 3-continued
| Compound No. | Structure | Analysis results (MS, $^1$H NMR) |
|---|---|---|
| 27 | 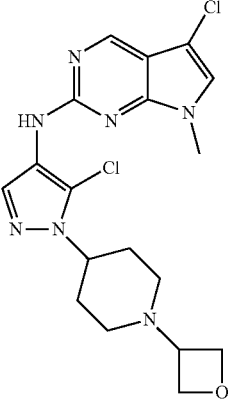 [SMILES: Cn1cc(Cl)c2cnc(Nc3cnn(C4CCN(C5COC5)CC4)c3Cl)nc21] | MS (ESI) m/z 422.2, 424.1 [M + H]$^+$; $^1$H NMR (300 MHz, CDCl$_3$) δ 8.16 (s, 1H), 8.33 (s, 1H), 6.84 (s, 1H), 6.67 (s, 1H), 4.72-4.64 (m, 4H), 4.28-4.21 (m, 1H), 3.73 (s, 3H), 3.61-3.53 (m, 1H), 2.94-2.90 (d, 25H, J = 11.7 Hz), 2.37-2.24 (m, 2H), 2.09-1.99 (m, 4H) |
| 28 | 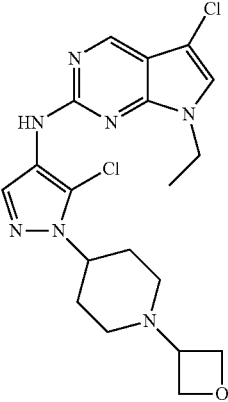 [SMILES: CCn1cc(Cl)c2cnc(Nc3cnn(C4CCN(C5COC5)CC4)c3Cl)nc21] | MS (ESI) m/z 436.1 [M + H]$^+$; $^1$H NMR (300 MHz, CDCl$_3$) δ 8.61 (s, 1H), 8.32 (s, 1H), 6.88 (s, 1H), 6.70 (s, 1H), 4.69-4.66 (m, 4H), 4.20-4.15 (m, 3H), 3.59-3.54 (t, J = 6.6 Hz, 1H), 2.91 (d, J = 11.1 Hz, 2H) 2.31-2.22 (m, 2H), 2.11-2.04 (m, 4H), 1.45 (t, J = 7.2 Hz, 3H). |
| 29 | 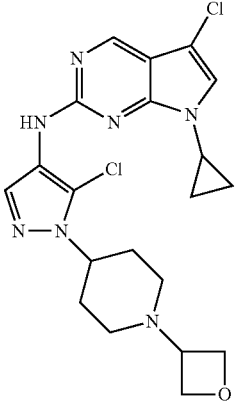 [SMILES: Clc1cn(C2CC2)c2nc(Nc3cnn(C4CCN(C5COC5)CC4)c3Cl)ncc12] | MS (ESI) m/z 448.0 [M + H]$^+$; $^1$H NMR (300 MHz, CDCl$_3$) δ 8.58 (s, 1H), 8.42 (s, 1H), 6.86 (s, 1H), 6.72 (s, 1H), 4.69-4.66 (m, 4H), 4.28-4.23 (m, 1H), 3.61-3.55 (m, 1H), 3.39-3.33 (m, 1H) 2.91 (d, J = 11.1 Hz, 2H), 2.36-2.25 (m, 4H), 1.16-1.11 (m, 4H). |

TABLE 3-continued

| Compound No. | Structure | Analysis results (MS, $^1$H NMR) |
|---|---|---|
| 30 | 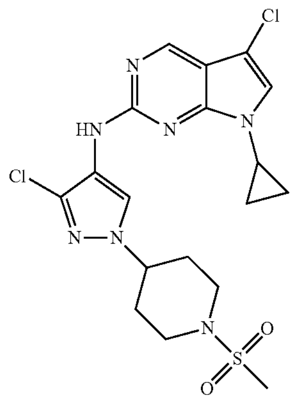 [SMILES: CS(=O)(=O)N1CCC(n2cc(Nc3ncc4c(Cl)cn(C5CC5)c4n3)c(Cl)n2)CC1] | MS (ESI) m/z 470.0 [M + H]$^+$; $^1$H NMR (300 MHz, CDCl$_3$) δ 8.59 (s, 1H), 8.44 (s, 1H), 6.88 (s, 1H), 6.71 (s, 1H), 4.42-4.35 (m, 1H), 3.99-3.95 (m, 2H), 3.39-3.32 (m, 1H), 3.011 (t, J = 11.4 Hz, 2H) 2.88 (s, 3H), 2.40-2.26 (m, 2H), 2.14-2.09 (m, 2H), 1.16-1.05 (m, 4H). |
| 31 | 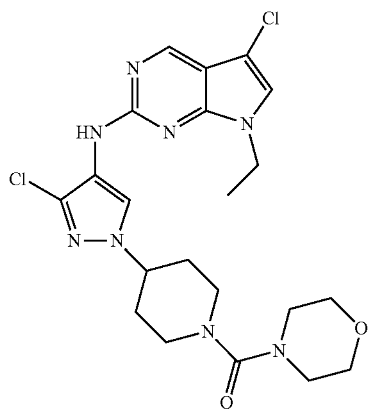 [SMILES: CCn1cc(Cl)c2cnc(Nc3cn(C4CCN(C(=O)N5CCOCC5)CC4)nc3Cl)nc21] | MS (ESI) m/z 493.0, 495.0 [M + H]$^+$ |
| 32 | 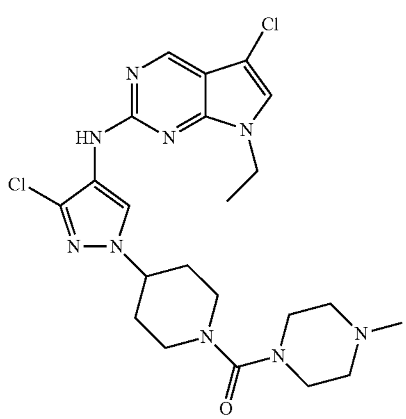 [SMILES: CCn1cc(Cl)c2cnc(Nc3cn(C4CCN(C(=O)N5CCN(C)CC5)CC4)nc3Cl)nc21] | MS (ESI) m/z 505.9, 508.0 [M + H]$^+$; $^1$H NMR (300 MHz, CDCl$_3$) δ 8.60 (s, 1H), 8.32 (s, 1H), 6.88 (s, 1H), 6.73 (s, 1H), 4.41-4.31 (m, 1H), 4.15 (q, J = 7.2 Hz, 2H), 3.90-3.78 (m, 2H), 3.41-3.31 (m, 4H), 2.94 (t, J = 12.3 Hz, 2H), 2.45-2.41 (m, 4H), 2.31 (s, 3H), 2.49-2.14 (m, 2H), 2.02-1.98 (m, 2H), 1.44 (t, J = 7.2 Hz, 3H). |

TABLE 3-continued

| Compound No. | Structure | Analysis results (MS, ¹H NMR) |
|---|---|---|
| 33 | 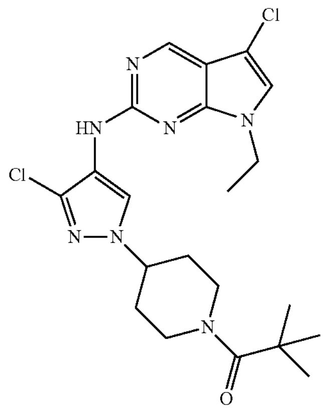 [SMILES: CCn1cc(Cl)c2cnc(Nc3cn(C4CCN(C(=O)C(C)(C)C)CC4)nc3Cl)nc21] | MS (ESI) m/z 464.2, 466.0 [M + H]⁺ |
| 34 | 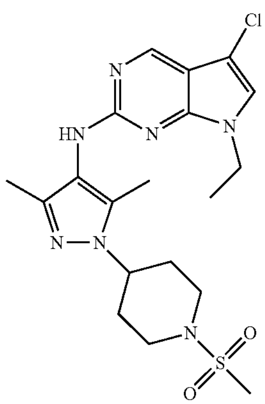 [SMILES: CCn1cc(Cl)c2cnc(Nc3c(C)nn(C4CCN(S(C)(=O)=O)CC4)c3C)nc21] | MS (ESI) m/z 452.2, 454.1 [M + H]⁺; ¹H NMR (300 MHz, CDCl₃) δ 8.55 (s, 1H), 6.81 (s, 1H), 6.17 (br s, 1H), 4.09-3.96 (m, 5H), 2.98-2.91 (m, 2H), 2.87 (s, 3H), 2.38-2.29 (m, 2H), 2.19 (s, 3H), 2.15 (s, 3H), 2.08-2.02 (m, 2H), 1.38 (t, J = 7.2 Hz, 3H). |
| 35 | 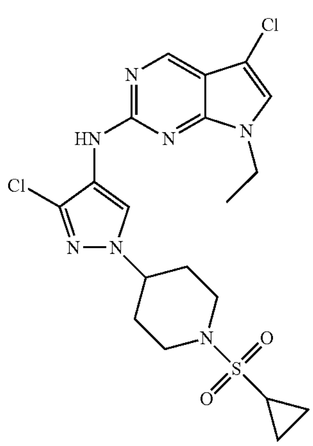 [SMILES: CCn1cc(Cl)c2cnc(Nc3cn(C4CCN(S(=O)(=O)C5CC5)CC4)nc3Cl)nc21] | MS (ESI) m/z 484.0, 486.0 [M + H]⁺; ¹H NMR (300 MHz, CDCl₃) δ 8.62 (s, 1H), 8.33 (s, 1H), 6.90 (s, 1H), 6.69 (br s, 1H), 4.42-4.35 (m, 1H), 4.17 (q, J = 7.2 Hz, 2H), 4.02-3.98 (m, 2H), 3.15-3.07 (m, 2H), 2.37-2.30 (m, 3H), 2.12-2.06 (m, 2H), 1.46 (t, J = 7.2 Hz, 3H), 1.24-1.22 (m, 2H), 1.10-1.02 (m, 2H). |

TABLE 3-continued

| Compound No. | Structure | Analysis results (MS, $^1$H NMR) |
|---|---|---|
| 36 | 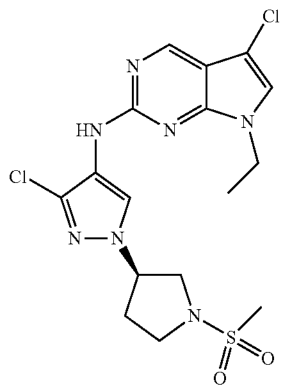 [SMILES: CCn1cc(Cl)c2cnc(Nc3cn([C@@H]4CCN(S(C)(=O)=O)C4)nc3Cl)nc21] | MS (ESI) m/z 444.0 [M + H]$^+$;<br>$^1$H NMR (300 MHz, CDCl$_3$) δ 8.62 (s, 1H), 8.28 (s, 1H), 6.90 (s, 1H), 6.66 (s, 1H), 5.19-5.07 (m, 1H), 4.17 (q, J = 7.2 Hz, 2H), 3.94-3.76 (m, 2H), 3.49 (q, J = 6.3 Hz, 2H), 2.93 (s, 3H), 1.46 (t, J = 7.5 Hz, 3H). |
| 37 | 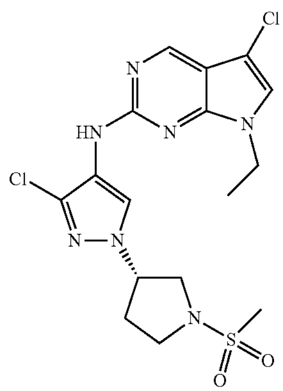 [SMILES: CCn1cc(Cl)c2cnc(Nc3cn([C@H]4CCN(S(C)(=O)=O)C4)nc3Cl)nc21] | MS (ESI) m/z 444.0 [M + H]$^+$;<br>$^1$H NMR (300 MHz, CDCl$_3$) δ 8.62 (s, 1H), 8.28 (s, 1H), 6.91 (s, 1H), 6.66 (s, 1H), 5.09-5.08 (m, 1H), 4.18 (q, J = 7.2 Hz, 2H), 3.94-3.88 (m, 1H), 3.81-3.76 (m, 1H), 3.67-3.63 (m, 2H), 2.93 (s, 3H), 2.50-2.43 (m, 2H), 1.46 (t, J = 7.2 Hz, 3H). |
| 38 | 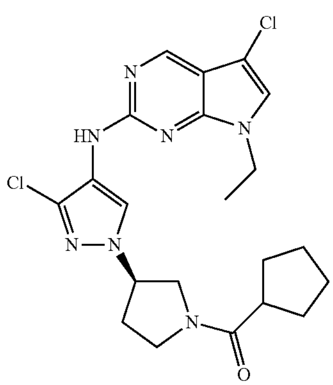 [SMILES: CCn1cc(Cl)c2cnc(Nc3cn([C@@H]4CCN(C(=O)C5CCCC5)C4)nc3Cl)nc21] | MS (ESI) m/z 461.9 [M + H]$^+$;<br>$^1$H NMR (300 MHz, CDCl$_3$) δ 8.61 (s, 1H), 8.28 (s, 1H), 6.90 (s, 1H), 6.72 (s, 1H), 5.08-4.99 (m, 1H), 4.30-4.12 (m, 2H), 3.98-3.93 (m, 2H), 3.68-3.64 (m, 1H), 2.86-2.74 (m, 1H), 2.49-2.36 (m, 2H), 1.86-1.78 (m, 6H), 1.61-1.55 (m, 1H), 1.48-1.42 (m, 1H). |
| 39 | 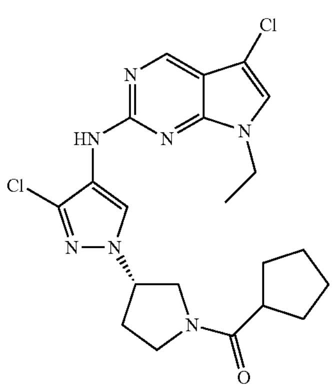 [SMILES: CCn1cc(Cl)c2cnc(Nc3cn([C@H]4CCN(C(=O)C5CCCC5)C4)nc3Cl)nc21] | MS (ESI) m/z 462.0 [M + H]$^+$;<br>$^1$H NMR (300 MHz, CDCl$_3$) δ 8.62 (s, 1H), 8.31-8.28 (d, J = 12.6 Hz, 1H), 6.90 (s, 1H), 6.70 (s, 1H), 5.01-4.98 (m, 1H), 4.17 (q, J = 7.2 Hz, 2H), 3.98-3.57 (m, 4H), 2.77-2.43 (m, 3H), 1.84-1.77 (m, 6H), 1.60-1.57 (m, 2H), 1.46 (t, J = 7.2 Hz, 3H). |

TABLE 3-continued
| Compound No. | Structure | Analysis results (MS, $^1$H NMR) |
|---|---|---|
| 40 | 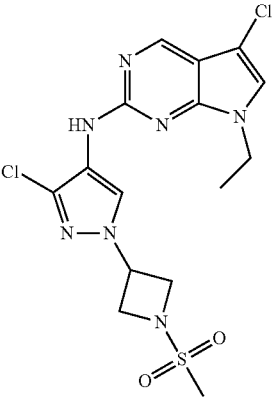 [SMILES: CCn1cc(Cl)c2cnc(Nc3cn(C4CN(S(C)(=O)=O)C4)nc3Cl)nc21] | MS (ESI) m/z 429.9 [M + H]$^+$;<br>$^1$H NMR (300 MHz, CDCl$_3$) δ 8.63 (s, 1H), 8.43 (s, 1H), 6.91 (s, 1H), 6.62 (s, 1H), 5.27 (quintet, J = 6.6 Hz, 1H), 4.53 (t, J = 2.4 Hz, 2H), 4.38 (t, J = 8.7 Hz, 2H), 4.18 (q, J = 7.2 Hz, 2H), 3.06 (s, 3H), 1.49 (t, J = 7.5 Hz, 3H). |
| 41 | 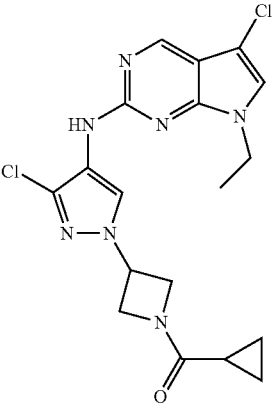 [SMILES: CCn1cc(Cl)c2cnc(Nc3cn(C4CN(C(=O)C5CC5)C4)nc3Cl)nc21] | MS (ESI) m/z 419.9 [M + H]$^+$;<br>$^1$H NMR (300 MHz, CDCl$_3$) δ 8.62 (s, 1H), 8.43 (s, 1H), 6.91 (s, 1H), 6.65 (s, 1H), 5.29 (quintet, J = 6.6 Hz, 1H), 4.84 (m, 1H), 4.70 (t, J = 7.5 Hz, 2H), 4.18 (q, J = 7.2 Hz, 2H), 1.27 (t, J = 7.2 Hz, 3H), 1.04 (d, J = 5.1 Hz, 2H), 0.80 (d, J = 5.1 Hz, 2H). |
| 42 | 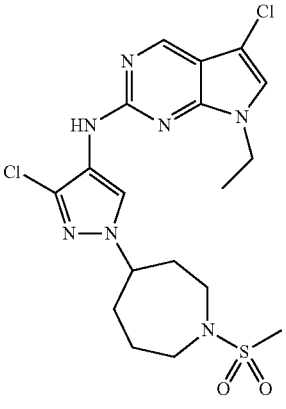 [SMILES: CCn1cc(Cl)c2cnc(Nc3cn(C4CCCN(S(C)(=O)=O)CC4)nc3Cl)nc21] | MS (ESI) m/z 473.2 [M + H]$^+$;<br>$^1$H NMR (300 MHz, CDCl$_3$) δ 8.75 (s, 1H), 8.29 (s, 1H), 6.94 (s, 1H), 4.94-4.57 (m, 1H), 4.34 (q, J = 7.5 Hz, 2H), 3.73-3.55 (m, 3H), 3.30-3.22 (m, 1H), 2.88 (s, 3H), 1.50 (t, J = 7.2 Hz, 3H). |

TABLE 3-continued

| Compound No. | Structure | Analysis results (MS, $^1$H NMR) |
|---|---|---|
| 43 | 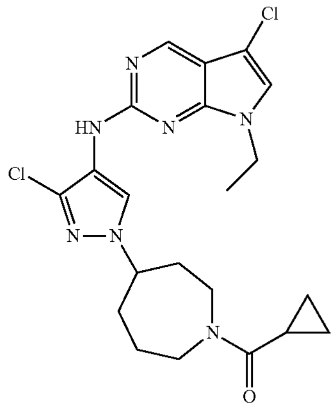 [SMILES: CCn1cc(Cl)c2cnc(Nc3cn(C4CCCN(C(=O)C5CC5)CC4)nc3Cl)nc21] | MS (ESI) m/z 463.2 [M + H]$^+$; $^1$H NMR (300 MHz, CDCl$_3$) δ 8.75 (s, 1H), 8.28 (s, 1H), 6.95 (s, 1H), 4.43-4.30 (m, 3H), 3.98-3.62 (m, 5H), 2.28-2.08 (m, 5H), 1.79-1.75 (m, 1H), 1.50 (t, J = 7.2 Hz, 3H), 1.11-1.00 (m, 2H), 0.83-0.79 (m, 2H). |

Example 44: Preparation of Compound 44

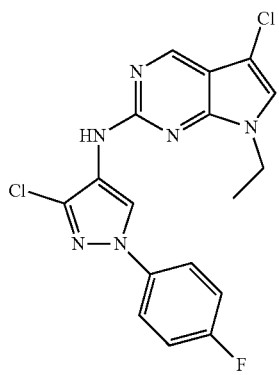 [SMILES: CCn1cc(Cl)c2cnc(Nc3cn(-c4ccc(F)cc4)nc3Cl)nc21]

Method 1:

Intermediate 8 (3-chloro-1-ethyl-6-(methylthio)-1H-pyrazolo[3,4-d]pyrimidine, 82.4 mg, 0.34 mmol) was dissolved in DMF (1 ml). mCPBA (156.5 mg, 0.90 mmol) was added thereto, followed by stirring thereof at room temperature for 1 hour. Intermediate 41 (3-chloro-1-(4-fluorophenyl)-1H-pyrazol-4-amine, 76.2 mg, 0.34 mmol) was added thereto, which was stirred at 120° C. for 16 hours. The temperature was then lowered to room temperature. Upon termination of the reaction, it was extracted with saturated NaHCO$_3$ and ethyl acetate, dried over MgSO$_4$, filtered, and concentrated under reduced pressure. It was subjected to column chromatography (MC:MeOH=40:1) to obtain 21 mg of the target compound (yield: 13%).

MS (ESI) m/z 392.0, 394.0 [M+H]$^+$

Method 2:

A suction flask was charged with Intermediate 8 (3-chloro-1-ethyl-6-(methylsulfonyl)-1H-pyrazolo[3,4-d]pyrimidine, 82.4 mg, 0.34 mmol), Intermediate 41 (3-chloro-1-(4-fluorophenyl)-1H-pyrazol-4-amine, 104.5 mg, 0.49 mmol), and p-toluenesulfonic acid (PTSA, 72.2 mg, 0.38 mmol). NMP (1 ml) was added thereto, followed by stirring thereof at 110° C. for 16 hours. The temperature was lowered to room temperature, and it was neutralized with saturated NaHCO$_3$ to precipitate a brown solid. The solid obtained by filtration was subjected to column chromatography with ethyl acetate to obtain 76.7 mg of the target compound (yield: 51%).

Examples 45 to 62: Preparation of Compounds 45 to 62

Compounds 45 to 62 were prepared by a procedure and a method similar to those of Example 44, except that the type of each intermediate was changed as shown in Table 4 below. The physicochemical properties of each compound are shown in Table 5 below.

TABLE 4

| No. | Intermediate | |
|---|---|---|
| Example 45 | Intermediate 8 | Intermediate 29 |
| Example 46 | Intermediate 10 | Intermediate 47 |
| Example 47 | Intermediate 8 | Intermediate 49 |
| Example 48 | Intermediate 8 | Intermediate 50 |
| Example 49 | Intermediate 9 | Intermediate 47 |
| Example 50 | Intermediate 9 | Intermediate 29 |
| Example 51 | Intermediate 8 | Intermediate 56 |
| Example 52 | Intermediate 8 | Intermediate 57 |
| Example 53 | Intermediate 8 | Intermediate 44 |
| Example 54 | Intermediate 8 | Intermediate 45 |
| Example 55 | Intermediate 8 | Intermediate 47 |
| Example 56 | Intermediate 8 | Intermediate 62 |
| Example 57 | Intermediate 8 | Intermediate 42 |
| Example 58 | Intermediate 8 | Intermediate 65 |
| Example 59 | Intermediate 8 | Intermediate 48 |
| Example 60 | Intermediate 8 | Intermediate 52 |
| Example 61 | Intermediate 8 | Intermediate 31 |
| Example 62 | Intermediate 8 | Intermediate 27 |

TABLE 5

| Compound No. | Structure | Analysis results (MS, ¹H NMR) |
|---|---|---|
| 45 | 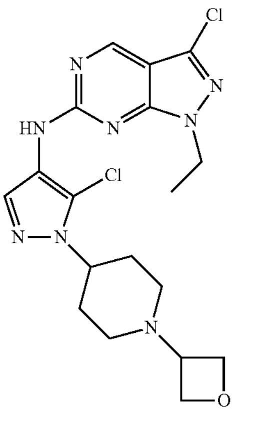 [SMILES: CCn1nc(Cl)c2cnc(Nc3cnn(C4CCN(C5COC5)CC4)c3Cl)nc21] | MS (ESI) m/z 437.4, 439.1 [M + H]⁺ |
| 46 | 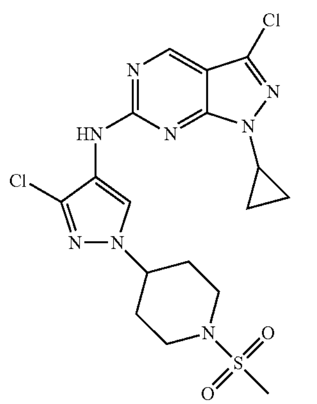 [SMILES: CS(=O)(=O)N1CCC(n2cc(Nc3ncc4c(Cl)nn(C5CC5)c4n3)c(Cl)n2)CC1] | MS (ESI) m/z 470.9, 473.0 [M + H]⁺; ¹H NMR (300 MHz, CDCl₃) δ 8.73 (s, 1H), 8.38 (s, 1H), 6.97 (s, 1H), 4.45-4.35 (m, 1H), 3.98 (d, J = 12.6 Hz, 2H), 3.67-3.59 (m, 1H), 3.01 (t, J = 12.0 Hz, 2H), 2.88 (s, 3H), 2.40-2.31 (m, 2H), 2.15-2.09 (m, 2H), 1.35-1.28 (m, 2H), 1.18-1.12 (m, 2H). |
| 47 | 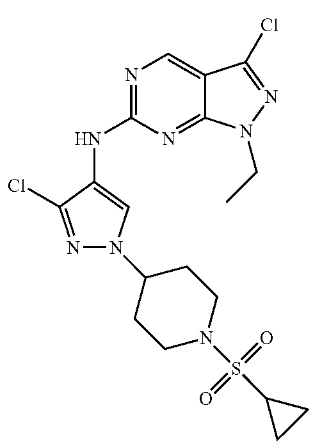 [SMILES: CCn1nc(Cl)c2cnc(Nc3cn(C4CCN(S(=O)(=O)C5CC5)CC4)nc3Cl)nc21] | MS (ESI) m/z 485.1, 487.1 [M + H]⁺; ¹H NMR (300 MHz, CDCl₃) δ 8.75 (s, 1H), 8.30 (s, 1H), 7.01 (s, 1H), 4.43-4.30 (m, 3H), 4.03-3.98 (m, 2H), 3.14-3.06 (m, 2H), 2.37-2.28 (m, 3H), 2.13-2.08 (m, 2H), 1.51-1.48 (m, 3H), 1.24-1.20 (m, 2H), 1.10-1.02 (m, 2H). |

TABLE 5-continued

| Compound No. | Structure | Analysis results (MS, ¹H NMR) |
| --- | --- | --- |
| 48 | 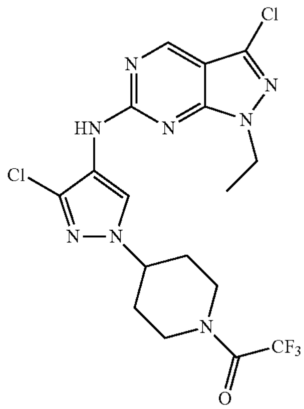 [SMILES: CCn1nc(Cl)c2cnc(Nc3cn(C4CCN(C(=O)C(F)(F)F)CC4)nc3Cl)nc21] | MS (ESI) m/z 476.8, 479.0 [M + H]+;<br>¹H NMR (300 MHz, CDCl₃) δ 8.76 (s, 1H), 8.31 (s, 1H), 6.91 (s, 1H), 4.66-4.53 (m, 2H), 4.35 (q, J = 7.2 Hz, 2H), 4.25-4.18 (m, 2H), 3.44-3.36 (m, 1H), 3.17-3.13 (m, 1H), 2.31-2.16 (m, 4H), 1.51 (t, J = 7.25 Hz, 3H). |
| 49 | 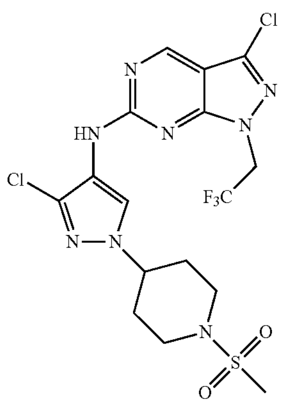 [SMILES: CS(=O)(=O)N1CCC(n2cc(Nc3ncc4c(Cl)nn(CC(F)(F)F)c4n3)c(Cl)n2)CC1] | MS (ESI) m/z 512.8, 514.8 [M + H]+;<br>¹H NMR (300 MHz, CDCl₃) δ 8.80 (s, 1H), 8.22 (s, 1H), 7.02 (s, 1H), 4.84 (q, J = 8.1 Hz), 4.46-4.37 (m, 1H), 4.00-3.94 (m, 2H), 3.06-2.99 (m, 2H), 2.89 (s, 3H), 2.40-2.28 (m, 2H), 2.14-2.10 (m, 2H). |
| 50 | 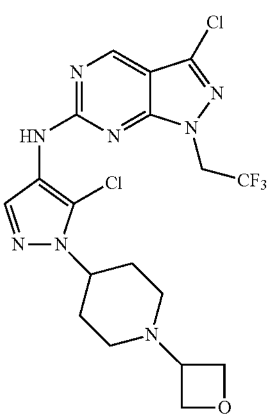 [SMILES: FC(F)(F)Cn1nc(Cl)c2cnc(Nc3cnn(C4CCN(C5COC5)CC4)c3Cl)nc21] | MS (ESI) m/z 490.9, 492.8 [M + H]+;<br>¹H NMR (300 MHz, CDCl₃) δ 8.79 (s, 1H), 8.21 (s, 1H), 7.01 (s, 1H), 4.84 (q, J = 8.1 Hz, 2H), 4.72-4.64 (m, 4H), 4.31-4.22 (m, 1H), 3.60-3.56 (m, 1H), 2.95-2.90 (m, 2H), 2.34-2.25 (m, 2H), 2.09-1.95 (m, 4H). |

TABLE 5-continued

| Compound No. | Structure | Analysis results (MS, ¹H NMR) |
|---|---|---|
| 51 | 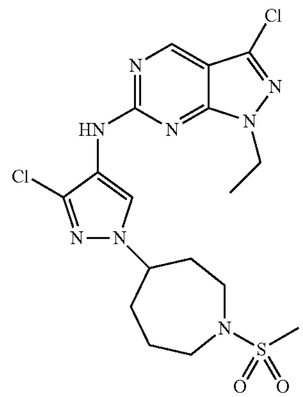 [SMILES: CCn1nc(Cl)c2cnc(Nc3cn(C4CCCN(S(C)(=O)=O)CC4)nc3Cl)nc21] | MS (ESI) m/z 473.2 [M + H]⁺; ¹H NMR (300 MHz, CDCl₃) δ 8.75 (s, 1H), 8.29 (s, 1H), 6.94 (s, 1H), 4.94-4.57 (m, 1H), 4.34 (q, J = 7.5 Hz, 2H), 3.73-3.55 (m, 3H), 3.30-3.22 (m, 1H), 2.88 (s, 3H), 1.50 (t, J = 7.2 Hz, 3H). |
| 52 | 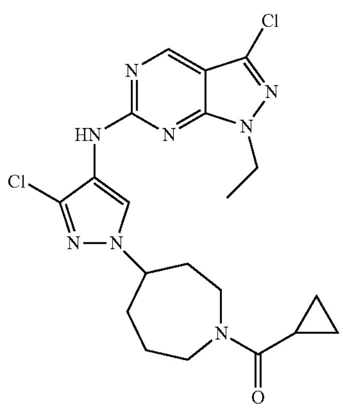 [SMILES: CCn1nc(Cl)c2cnc(Nc3cn(C4CCCN(C(=O)C5CC5)CC4)nc3Cl)nc21] | MS (ESI) m/z 463.2 [M + H]⁺; ¹H NMR (300 MHz, CDCl₃) δ 8.75 (s, 1H), 8.28 (s, 1H), 6.95 (s, 1H), 4.43-4.30 (m, 3H), 3.98-3.62 (m, 5H), 2.28-2.08 (m, 5H), 1.79-1.75 (m, 1H), 1.50 (t, J = 7.2 Hz, 3H), 1.11-1.00 (m, 2H), 0.83-0.79 (m, 2H). |
| 53 | 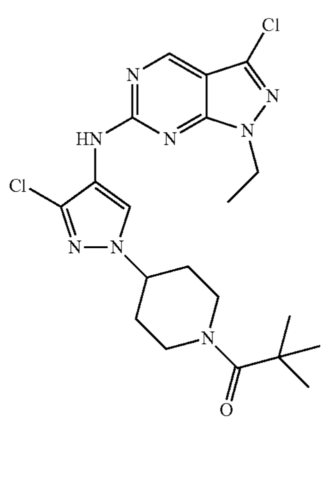 [SMILES: CCn1nc(Cl)c2cnc(Nc3cn(C4CCN(C(=O)C(C)(C)C)CC4)nc3Cl)nc21] | MS (ESI) m/z 464.9, 466.9 [M + H]⁺; ¹H NMR (300 MHz, CDCl₃) δ 8.75 (s, 1H), 8.31 (s, 1H), 6.92 (s, 1H), 4.61 (d, J = 13.5 Hz, 2H), 4.49-4.46 (m, 1H), 4.34 (q, J = 7.2 Hz, 2H), 3.02 (t, J = 11.1 Hz, 2H), 2.18-2.03 (m, 4H), 1.50 (t, J = 7.2 Hz, 3H), 1.34 (s, 9H). |

TABLE 5-continued

| Compound No. | Structure | Analysis results (MS, ¹H NMR) |
|---|---|---|
| 54 | 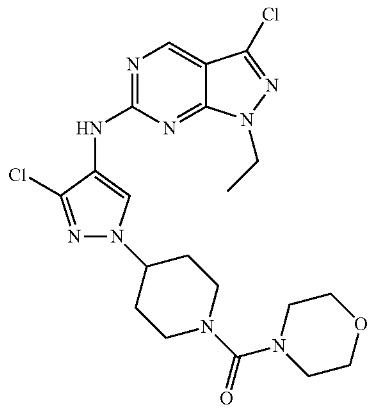 [SMILES: CCn1nc(Cl)c2cnc(Nc3cn(C4CCN(C(=O)N5CCOCC5)CC4)nc3Cl)nc21] | MS (ESI) m/z 394.1, 396.3 [M + H]⁺ |
| 55 | 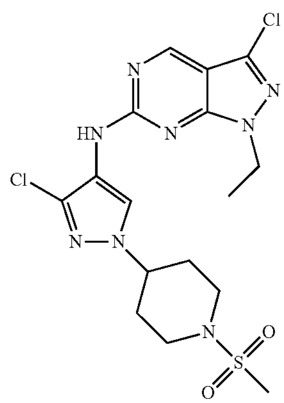 [SMILES: CCn1nc(Cl)c2cnc(Nc3cn(C4CCN(S(C)(=O)=O)CC4)nc3Cl)nc21] | MS (ESI) m/z 458.8 [M + H]⁺; ¹H NMR (300 MHz, CDCl₃) δ 8.76 (s, 1H), 8.31 (s, 1H), 6.94 (s, 1H), 4.43-4.31 (m, 3H), 3.97 (d, J = 12.6, 2H), 3.06-3.27 (m, 2H), 2.88 (s, 3H), 2.40-2.27 (m, 2H), 2.15-2.09 (m, 2H), 1.51 (t, J = 7.2 Hz, 3H). |
| 56 | 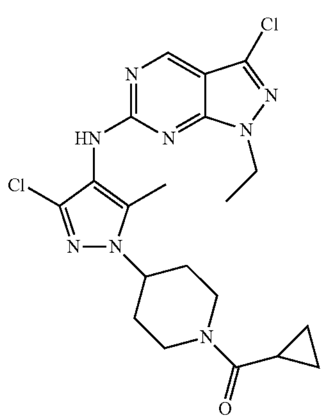 [SMILES: CCn1nc(Cl)c2cnc(Nc3c(Cl)nn(C4CCN(C(=O)C5CC5)CC4)c3C)nc21] | MS (ESI) m/z 462.9, 464.9 [M + H]⁺; ¹H NMR (300 MHz, CDCl₃) δ 8.73 (s, 1H), 4.32-4.17 (m, 3H), 2.27 (s, 3H), 2.14 (s, 3H), 1.82-1.75 (m, 2H), 1.50-1.43 (m, 4H), 1.27 (s, 2H), 1.04-1.03 (m, 2H), 0.82-0.78 (m, 2H). |

TABLE 5-continued

| Compound No. | Structure | Analysis results (MS, ¹H NMR) |
|---|---|---|
| 57 | 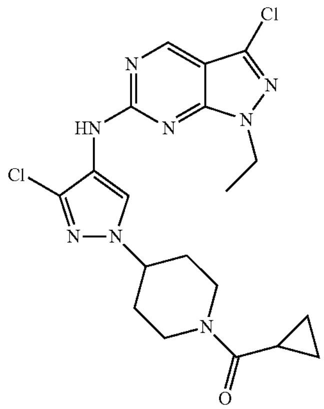 [SMILES: CCn1nc(Cl)c2cnc(Nc3cn(C4CCN(C(=O)C5CC5)CC4)nc3Cl)nc21] | MS (ESI) m/z 499.1, 451.0 [M + H]$^+$;<br>¹H NMR (300 MHz, CDCl$_3$) δ 8.75 (s, 1H), 8.30 (s, 1H), 6.95 (s, 1H), 4.76-4.74 (m, 1H), 4.54-4.52 (m, 2H), 4.34 (q, J = 7.2 Hz, 2H), 3.39-3.32 (m, 2H), 2.26-2.06 (m, 6H), 1.83-1.78 (m, 2H), 1.51 (t, J = 7.2 Hz, 3H), 1.05-1.02 (m, 2H), 0.85-0.82 (m, 2H). |
| 58 | 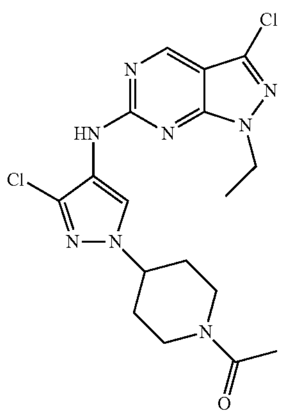 [SMILES: CCn1nc(Cl)c2cnc(Nc3cn(C4CCN(C(C)=O)CC4)nc3Cl)nc21] | MS (ESI) m/z 423.1, 425.2 [M + H]$^+$;<br>¹H NMR (300 MHz, CDCl$_3$) δ 8.74 (s, 1H), 8.28 (s, 1H), 7.01 (s, 1H), 4.78-4.74 (m, 1H), 4.50-4.43 (m, 1H), 4.37-4.30 (m, 2H), 4.04-3.99 (m, 1H), 3.27 (t, J = 12.0 Hz, 1H), 2.80 (t, J = 10.5 Hz, 1H), 2.16 (s, 3H), 2.07-2.01 (m, 4H), 1.50 (t, J = 7.2 Hz, 3H). |
| 59 | 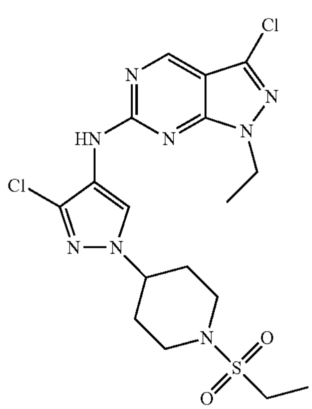 [SMILES: CCn1nc(Cl)c2cnc(Nc3cn(C4CCN(S(=O)(=O)CC)CC4)nc3Cl)nc21] | MS (ESI) m/z 473.1, 475.0 [M + H]$^+$;<br>¹H NMR (300 MHz, CDCl$_3$) δ 8.75 (s, 1H), 8.30 (s, 1H), 6.95 (s, 1H), 4.41-4.30 (m, 3H), 4.03-3.95 (m, 2H), 3.13-3.03 (m, 4H), 2.48-2.21 (m, 2H), 2.18-2.03 (m, 2H), 1.51 (t, J = 7.2 Hz, 3H), 1.42 (t, J = 7.2 Hz, 3H). |

TABLE 5-continued

| Compound No. | Structure | Analysis results (MS, $^1$H NMR) |
|---|---|---|
| 60 | 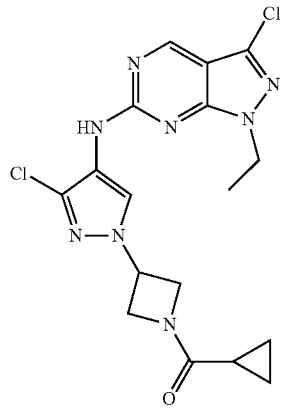 [SMILES: CCn1nc(Cl)c2cnc(Nc3cn(C4CN(C(=O)C5CC5)C4)nc3Cl)nc21] | MS (ESI) m/z 421.3 [M + H]$^+$; $^1$H NMR (300 MHz, CDCl$_3$) δ 8.76 (s, 1H), 8.39 (s, 1H), 6.96 (s, 1H), 5.29 (quintet, J = 6.9 Hz, 1H), 4.97-4.82 (m, 1H), 4.73 (t, J = 7.2 Hz, 2H), 4.48 (t, J = 6.6 Hz, 2H), 4.33 (q, J = 7.2 Hz, 2H), 1.51 (t, J = 7.2 Hz, 3H), 1.04 (d, J = 4.8 Hz, 2H), 0.81 (d, J = 4.8 Hz, 2H). |
| 61 | 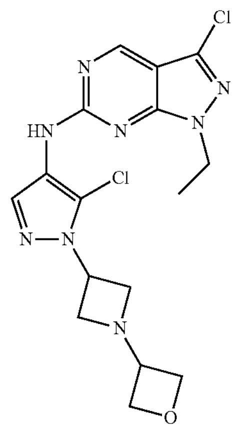 [SMILES: CCn1nc(Cl)c2cnc(Nc3cnn(C4CN(C5COC5)C4)c3Cl)nc21] | MS (ESI) m/z 408.9 [M + H]$^+$; $^1$H NMR (300 MHz, CDCl$_3$) δ 8.75 (s, 1H), 8.35 (s, 1H), 6.96 (s, 1H), 5.16 (quintet, J = 6.9 Hz, 1H), 4.77 (t, J = 6.9 Hz, 2H), 4.65 (t, J = 5.4 Hz, 2H), 4.34 (q, J = 7.2 Hz, 2H), 3.98-3.76 (m, 5H), 1.50 (t, J = 7.2 Hz, 3H), 1.04 (d, J = 4.8 Hz, 2H), 0.81 (d, J = 4.8 Hz, 2H). |
| 62 | 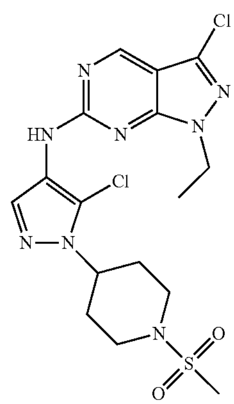 [SMILES: CCn1nc(Cl)c2cnc(Nc3cnn(C4CCN(S(C)(=O)=O)CC4)c3Cl)nc21] | MS (ESI) m/z 459.0, 461.0 [M + H]$^+$; $^1$H NMR (300 MHz, CDCl$_3$) δ 8.78 (s, 1H), 8.18 (s, 1H), 7.10 (s, 1H), 4.36 (q, J = 7.2 Hz, 2H), 4.28-4.21 (m, 2H), 3.96 (d, J = 12.9 Hz, 2H), 2.98 (t, J = 9.0 Hz, 2H), 2.87 (s, 3H), 2.33-2.17 (m, 4H), 1.56-1.55 (m, 3H). |

Evaluation Example: Inhibitory Effect on LRRK2

The inhibitory effect of Compounds 1 to 62 on LRRK2 (leucine-rich repeat kinase 2) in vitro was measured. In the analysis of the results, IC$_{50}$ values were calculated for a quantitative comparison of the in vitro activity.

Test Method

After the compound was dissolved in 100% DMSO at 10 mM, it was serially diluted to the range of 1 μM to 10 μM using biochemical LRRK2 assay buffer (50 mM HEPES (4-(2-hydroxyethyl)-1-piperazineethanesulfonic acid) pH 7.5, 10 mM MgCl$_2$, 1 mM EGTA (1,2-bis(o-aminophenoxy)ethane-N,N,N',N'-tetraacetic acid), 2 mM DTT (dithiothrei-tol), and 0.01% TWEEN-20 (Aldrich)). Purified LRRK2 (CARNA BIOSCIENCES) was added to a black U-bottom 96-well microtiter plate containing 6 μl of the serially diluted compound, followed by incubation at room temperature for 30 minutes. For the kinase reaction, ATP and a substrate solution specific urea-polypeptide (ULIGHT™-poly TK, PerkinElmer) were added. The reaction was carried out at room temperature for 1 hour, and it was detected with an detection solution (brand name: LANCE™) containing EDTA. A LANCE detection solution containing europium-labeled antibody (LRRK2 specific PT66) was added, followed by incubation at room temperature for 50 minutes, to terminate the kinase experiment. The phosphorylated substrate was detected by 665 nm emission measurement. $IC_{50}$ values were calculated by a non-linear regression analysis using a Prism program (PRISM™ software) with reference to the absence of a kinase inhibitor. The results are shown in Table 6 below.

As a comparative assay, a compound LRR2-IN-1, that known to be a reference compound for LRRK2 inhibitor, have also tested an inhibitory activity.

TABLE 6

| Compound No. | $IC_{50}$ (nM) |
|---|---|
| LRRK2-IN-1 | 8.20 |
| 25 | 6.67 |
| 28 | 6.50 |
| 30 | 2.02 |
| 31 | 4.66 |
| 32 | 2.50 |
| 33 | 6.07 |
| 35 | 6.66 |
| 42 | 5.11 |
| 43 | 5.83 |
| 46 | 7.91 |
| 47 | 6.48 |
| 51 | 4.75 |
| 52 | 5.60 |
| 55 | 4.49 |
| 57 | 7.22 |
| 58 | 5.92 |
| 59 | 3.94 |

As shown in Table 6 above, the compounds of the present invention had an inhibitory activity to LRRK2 with an single digit nM $IC_{50}$ values and had superior to those of LRRK2-IN-1. Specifically, six tyrosine kinase panel tests were carried out on Compounds 25, 28, 30, 31, 32, 33, 35, 42, 43, 46, 47, 51, 52, 55, 57, 58, and 59 in order to evaluate the selectivity.

As a result, they selectively showed high inhibitory activity to LRRK2, indicating that the selectivity to the LRRK2 inhibitory activity was excellent.

The invention claimed is:
1. A compound of Formula 1:

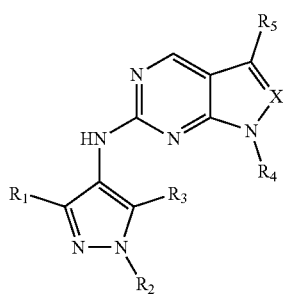

[Formula 1]

or a pharmaceutically acceptable salt or stereoisomer thereof,
wherein:
X is CH or N;
$R_1$ is hydrogen, halogen, $C_{1-4}$ alkyl, $C_{1-4}$ haloalkyl, $OC_{1-4}$ alkyl, or $OC_{1-4}$ haloalkyl;
$R_2$ is $C_{1-6}$ alkyl, $C_{1-6}$ alkylene-$OC_{1-3}$ alkyl, $C_{1-6}$ alkylene-$C_{3-6}$ cycloalkyl, $OC_{1-6}$ alkyl, $C_{3-6}$ cycloalkyl, 4- to 7-membered heterocycloalkyl, or $C_{6-10}$ aryl;
wherein the 4- to 7-membered heterocycloalkyl contains one or more heteroatoms independently selected from the group consisting of nitrogen, oxygen, and sulfur;
wherein the 4- to 7-membered heterocycloalkyl is optionally substituted with one or more substituents independently selected from the group consisting of $C_{1-4}$ alkyl, $C(O)C_{1-4}$ alkyl, $C(O)C_{1-4}$ haloalkyl, $C(O)C_{3-6}$ cycloalkyl, C(O)-(4- to 7-membered heterocycloalkyl), $S(O)_2C_{1-4}$ alkyl, $S(O)_2C_{3-6}$ cycloalkyl, and oxetanyl;
wherein each 4- to 7-membered heterocycloalkyl of each C(O)-(4- to 7-membered heterocycloalkyl) substituent of the 4- to 7-membered heterocycloalkyl is optionally substituted with one or more independently selected $C_{1-4}$ alkyl substituents; and
wherein the $C_{6-10}$ aryl is optionally substituted with one or more independently selected halogen substituents;
$R_3$ is hydrogen, halogen, or $C_{1-4}$ alkyl;
$R_4$ is $C_{1-6}$ alkyl, $C_{1-6}$ haloalkyl, or $C_{3-6}$ cycloalkyl;
wherein the $C_{3-6}$ cycloalkyl is optionally substituted with one or more independently selected halogen substituents; and
$R_5$ is halogen, $C_{1-4}$ alkyl, or $C_{1-4}$ haloalkyl.

2. The compound of claim 1, or a pharmaceutically acceptable salt or stereoisomer thereof, wherein the pharmaceutically acceptable salt is selected from the group consisting of a benzenesulfonate salt, a ethanesulfonate salt, a hydrobromide salt, a hydrochloride salt, a hydroiodide salt, a methanesulfonate salt, a nitrate salt, a sulfate salt, and a toluenesulfonate salt.

3. The compound of claim 1, or a pharmaceutically acceptable salt or stereoisomer thereof, wherein $R_1$ is hydrogen, halogen, $C_{1-4}$ alkyl, $C_{1-4}$ trifluoroalkyl, or $OC_{1-4}$ alkyl.

4. The compound of claim 1, or a pharmaceutically acceptable salt or stereoisomer thereof, wherein $R_2$ is $C_{1-4}$ alkyl, $C_{1-4}$ alkylene-$OC_{1-3}$ alkyl, $C_{1-4}$ alkylene-$C_{3-6}$ cycloalkyl, $OC_{1-4}$ alkyl, $C_{3-6}$ cycloalkyl, 4- to 7-membered heterocycloalkyl, or $C_{6-10}$ aryl;
wherein the 4- to 7-membered heterocycloalkyl contains one or more heteroatoms independently selected from the group consisting of nitrogen, oxygen, and sulfur;
wherein the 4- to 7-membered heterocycloalkyl is optionally substituted with one or more substituents independently selected from the group consisting of $C_{1-4}$ alkyl, $C(O)C_{1-4}$ alkyl, $C(O)C_{1-4}$ trifluoroalkyl, $C(O)C_{3-6}$ cycloalkyl, C(O)-(4- to 7-membered heterocycloalkyl), $S(O)_2C_{1-4}$ alkyl, $S(O)_2C_{3-6}$ cycloalkyl, and oxetanyl;
wherein the C(O)-(4- to 7-membered heterocycloalkyl) substituent of the 4- to 7-membered heterocycloalkyl is optionally substituted with one or more independently selected $C_{1-4}$ alkyl substituents; and
wherein the $C_{6-10}$ aryl is optionally substituted with one or more substituents independently selected from the group consisting of F and Cl.

5. The compound of claim 4, or a pharmaceutically acceptable salt or stereoisomer thereof, wherein $R_2$ is selected from the group consisting of:

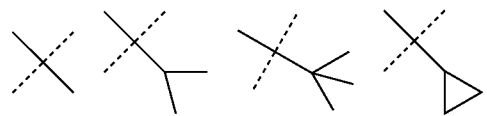

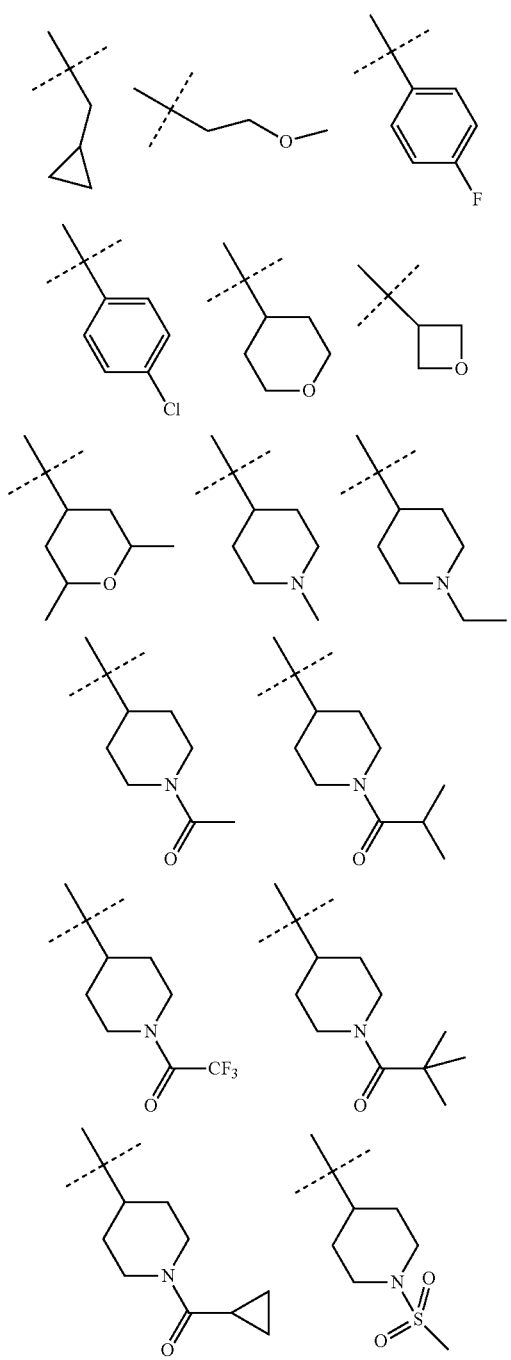
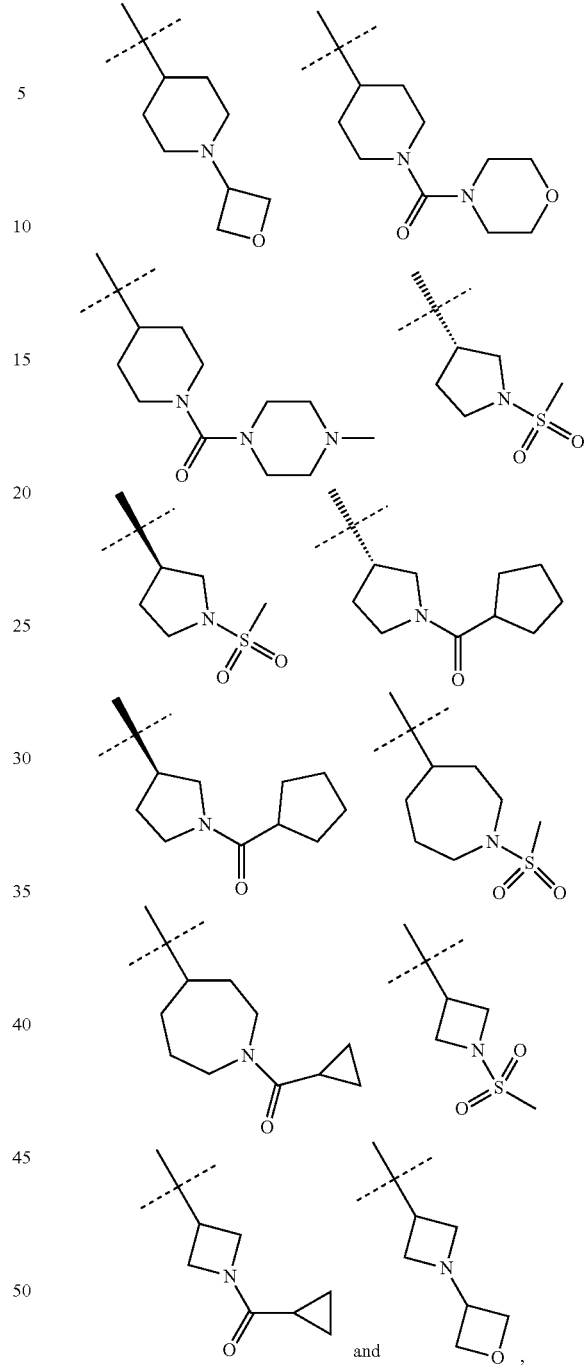

wherein:
---- is the point of attachment to the nitrogen atom of the pyrazolyl ring.

6. The compound of claim 1, or a pharmaceutically acceptable salt or stereoisomer thereof, wherein $R_4$ is $C_{1-4}$ alkyl, $C_{1-4}$ trifluoroalkyl, or $C_{3-6}$ cycloalkyl.

7. The compound of claim 1, or a pharmaceutically acceptable salt or stereoisomer thereof, wherein $R_5$ is halogen, $C_{1-4}$ alkyl, or $C_{1-4}$ trifluoroalkyl.

8. The compound of claim 1, or a stereoisomer thereof, wherein the compound, or stereoisomer thereof, is selected from the group consisting of:

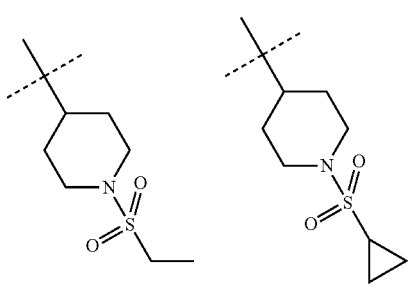

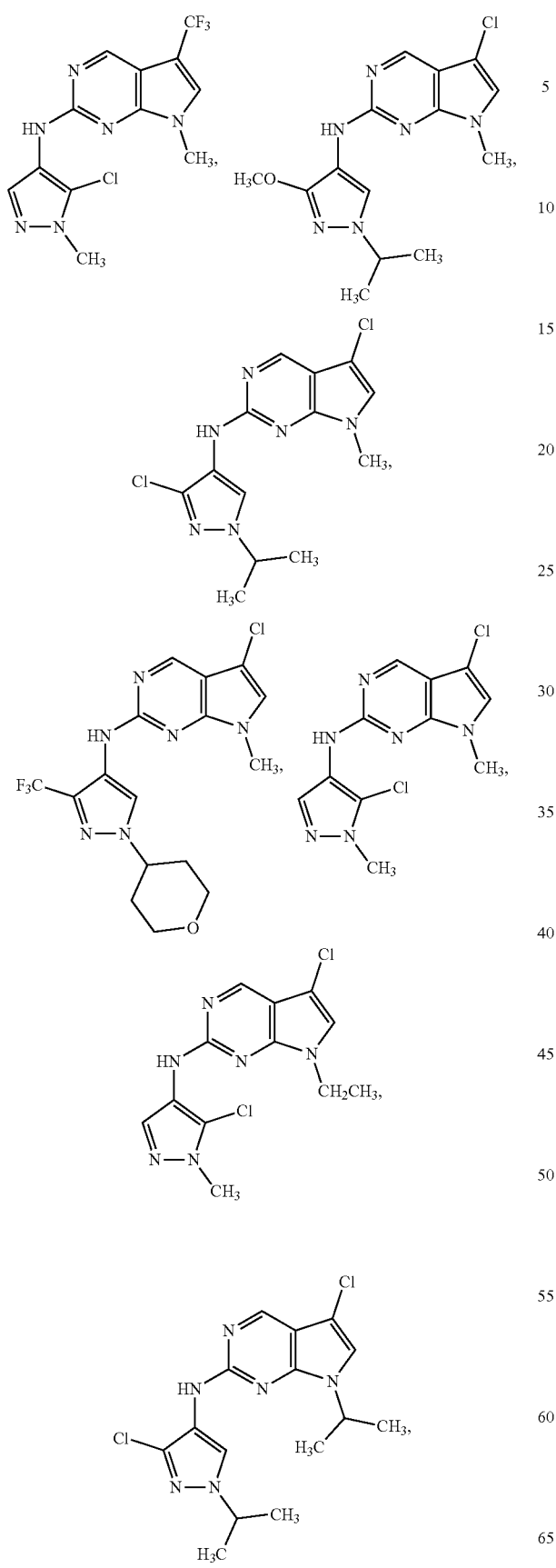
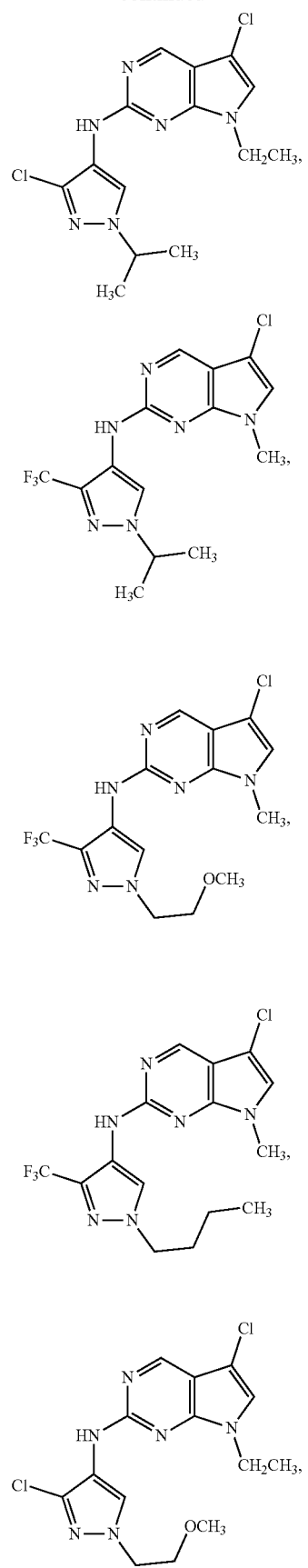

113
-continued
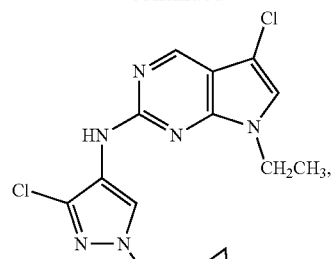
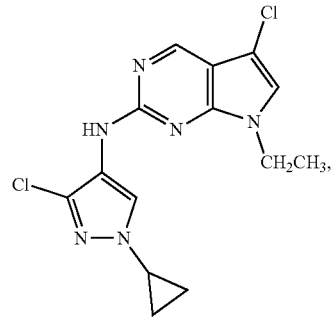
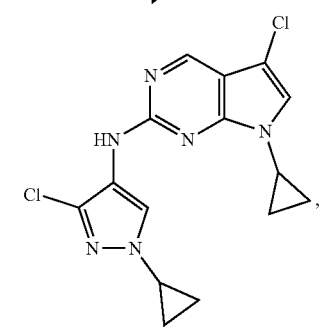
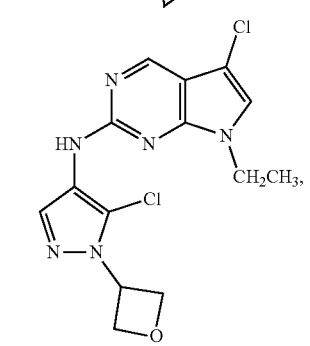
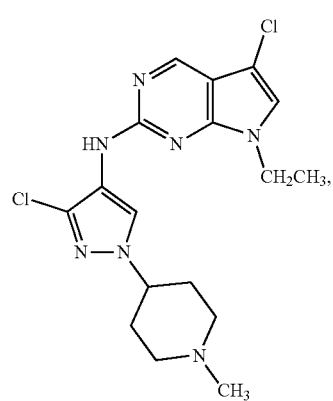
114
-continued
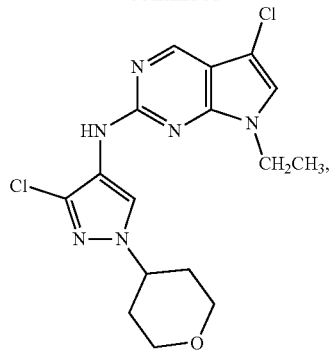 [SMILES: CCn1cc(Cl)c2cnc(Nc3cn(C4CCOCC4)nc3Cl)nc21]
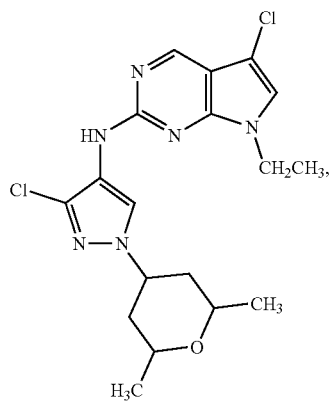
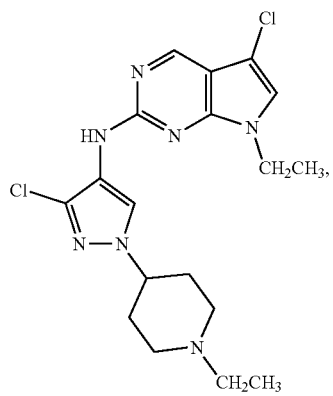
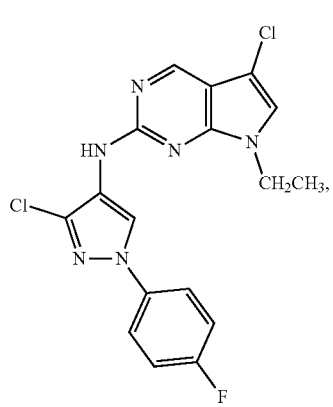

115
-continued
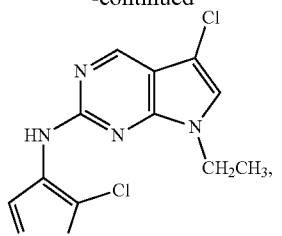
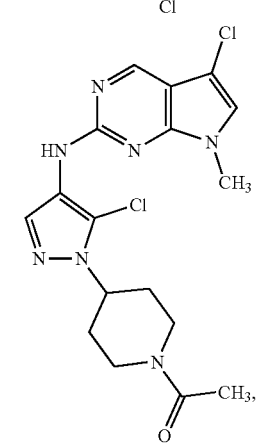
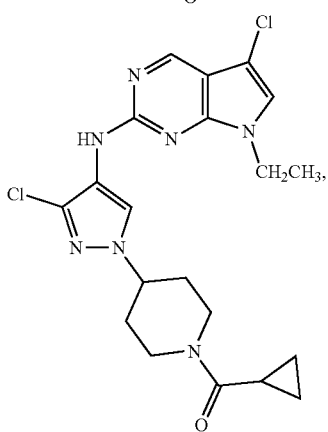
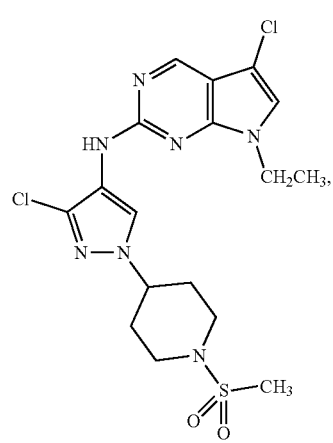
116
-continued
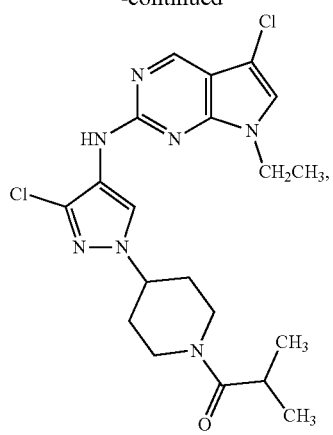
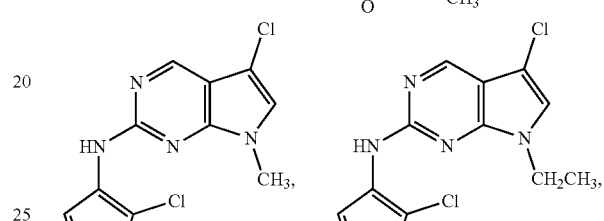
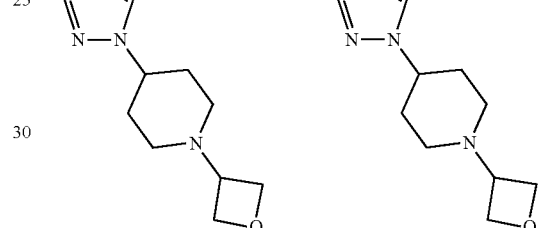
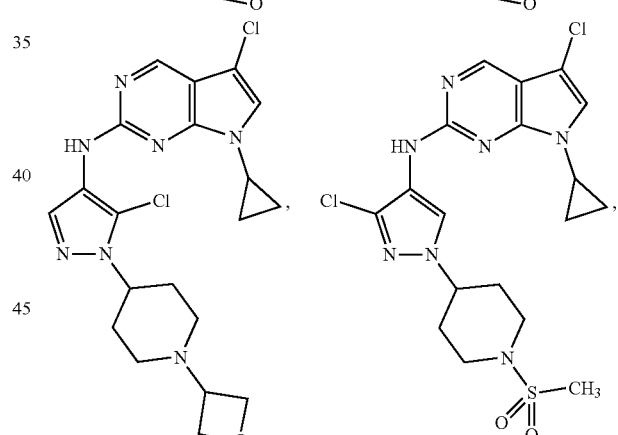
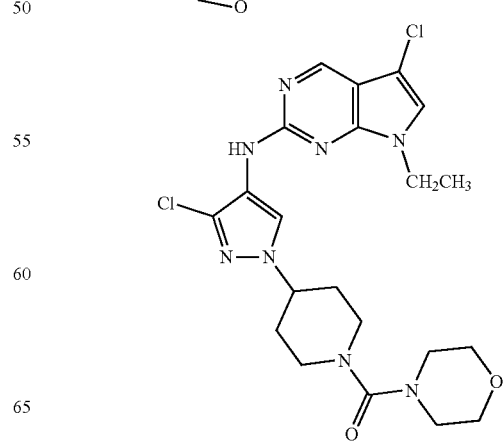

117
-continued
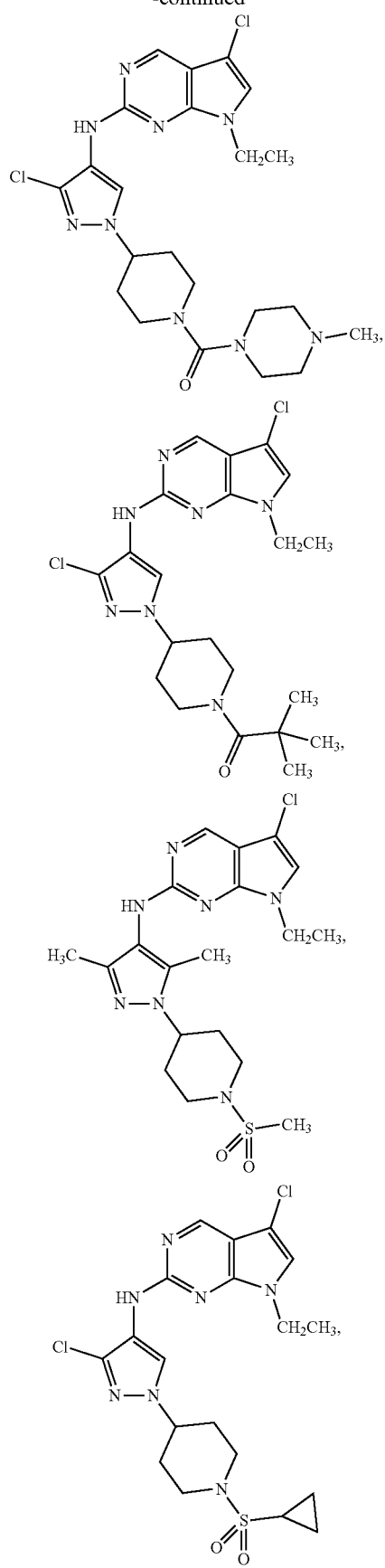
118
-continued
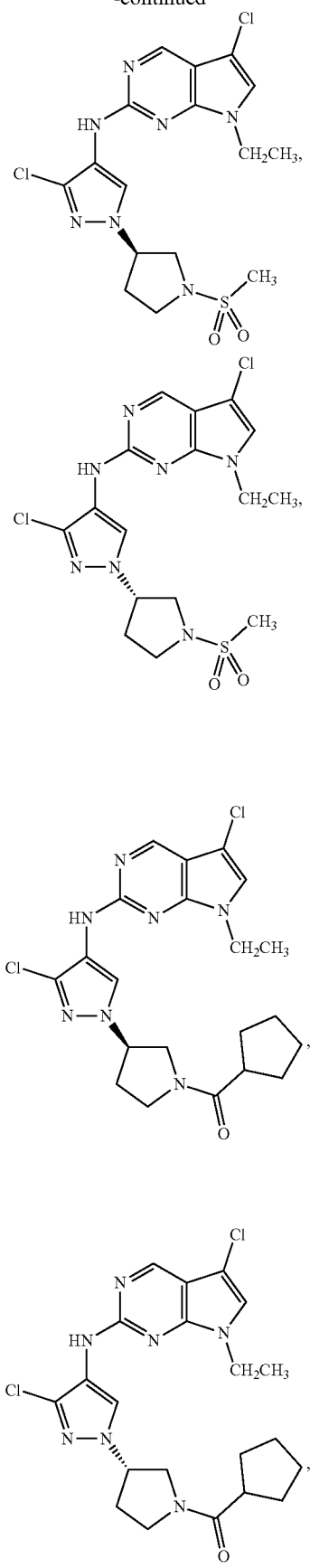

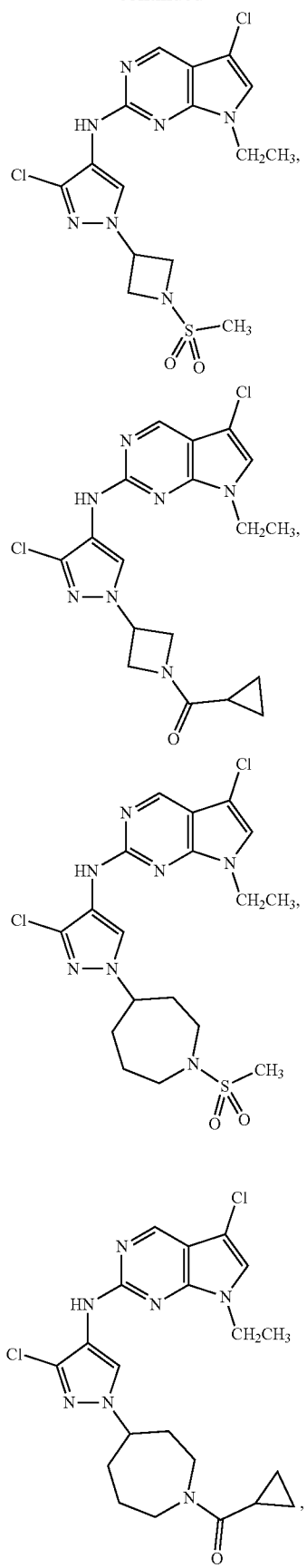
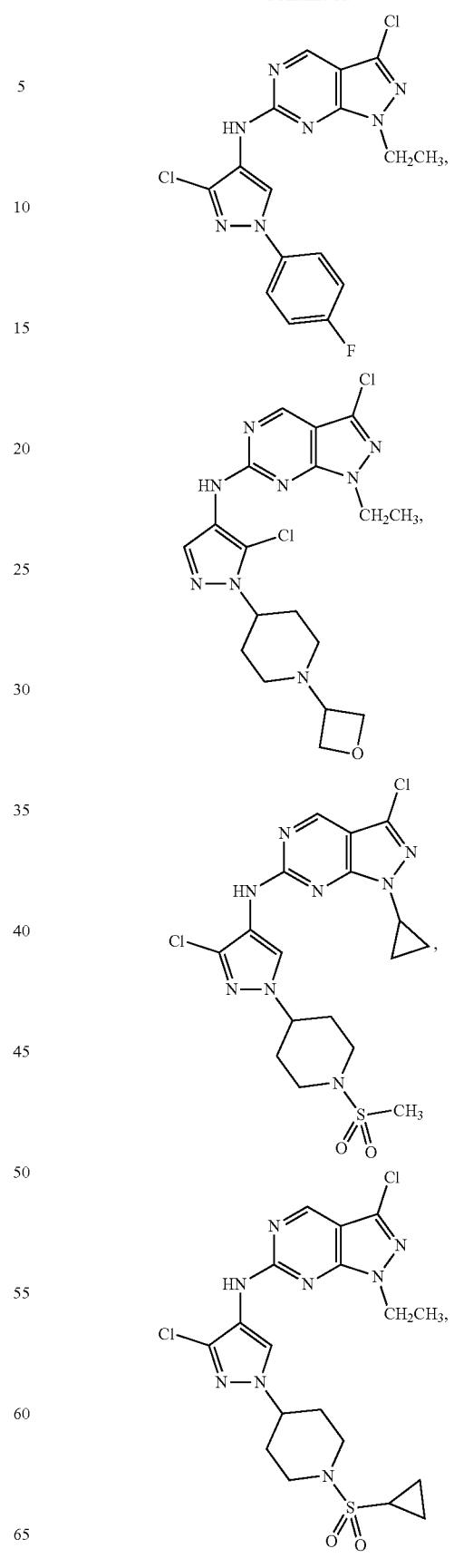

121
-continued
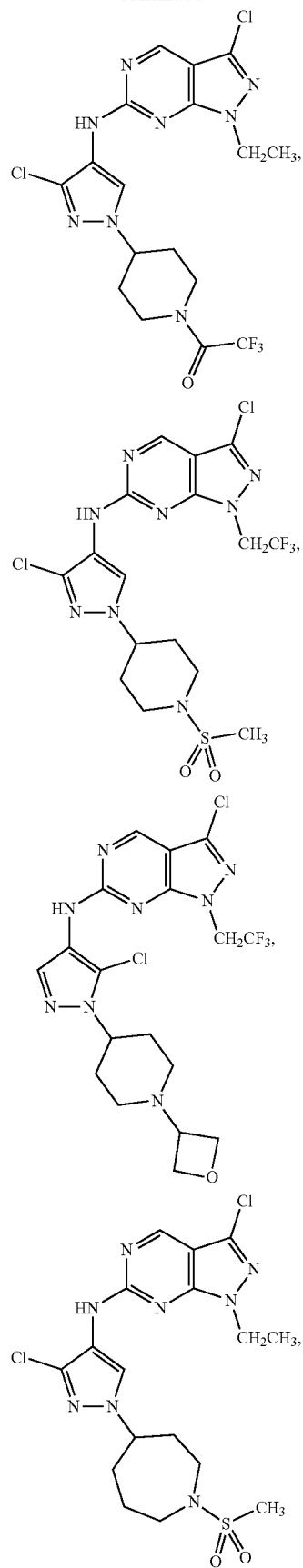
122
-continued
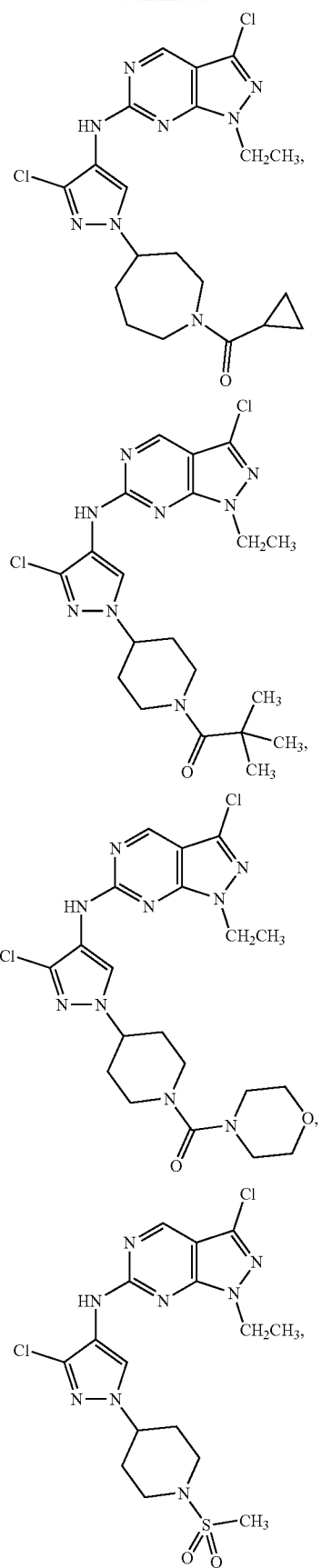

123
-continued

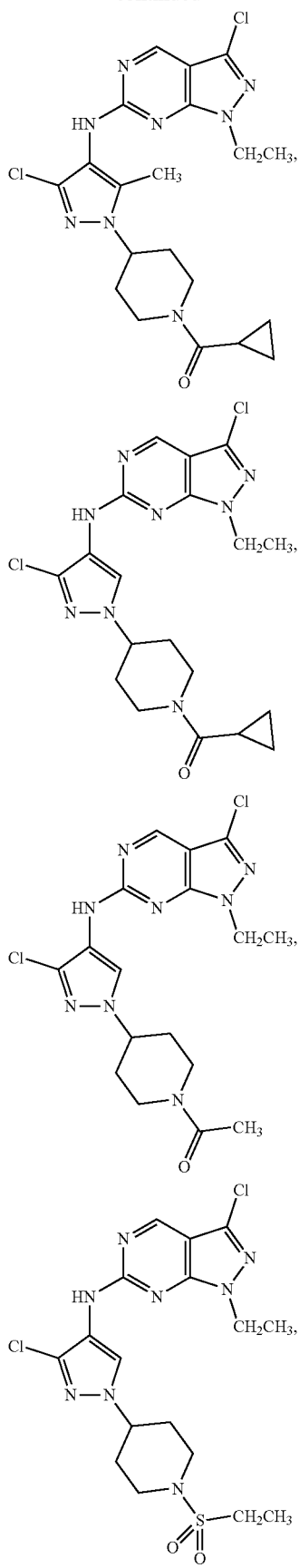

124
-continued

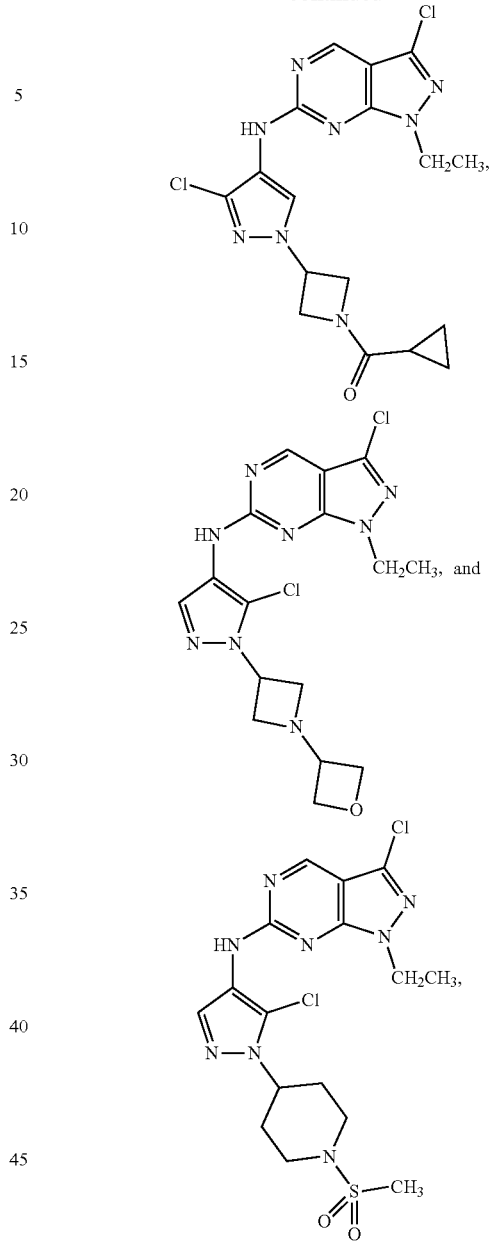

or a pharmaceutically acceptable salt thereof.

9. A pharmaceutical composition comprising at least one pharmaceutically acceptable additive and the compound of claim 1, or a pharmaceutically acceptable salt or stereoisomer thereof, as an active ingredient.

10. A pharmaceutical composition comprising at least one pharmaceutically acceptable additive and the compound of claim 8, or a pharmaceutically acceptable salt or stereoisomer thereof, as an active ingredient.

11. A method for selectively inhibiting leucine rich repeat kinase 2 activity in a subject, wherein the method comprises administering to the subject in need thereof a therapeutically effective amount of the compound of claim 1, or a pharmaceutically acceptable salt or stereoisomer thereof.

12. A method for selectively inhibiting leucine rich repeat kinase 2 activity in a subject, wherein the method comprises administering to the subject in need thereof a therapeutically effective amount of the compound of claim 8, or a pharmaceutically acceptable salt or stereoisomer thereof.

13. A method for treating a degenerative brain disease in a subject, wherein the method comprises administering to the subject in need thereof a therapeutically effective amount of the compound of claim 1, or a pharmaceutically acceptable salt or stereoisomer thereof.

14. The method of claim 13, wherein the degenerative brain disease is associated with leucine rich repeat kinase 2 hyperactivity in the subject.

15. The method of claim 13, wherein the degenerative brain disease is Parkinson's disease.

16. A method for treating a degenerative brain disease in a subject, wherein the method comprises administering to the subject in need thereof a therapeutically effective amount of the compound of claim 8, or a pharmaceutically acceptable salt or stereoisomer thereof.

17. The method of claim 16, wherein the degenerative brain disease is associated with leucine rich repeat kinase 2 hyperactivity in the subject.

18. The method of claim 16, wherein the degenerative brain disease is Parkinson's disease.

\* \* \* \* \*